(12) United States Patent
Nobile et al.

(10) Patent No.: US 12,226,386 B2
(45) Date of Patent: Feb. 18, 2025

(54) COMPOSITIONS AND METHODS FOR TREATING BIOFILMS

(71) Applicant: The Regents of the University of California, Oakland, CA (US)

(72) Inventors: Clarissa J. Nobile, Merced, CA (US); Megha Gulati, Merced, CA (US)

(73) Assignee: The Regents of the University of California, Oakland, CA (US)

( * ) Notice: Subject to any disclaimer, the term of this patent is extended or adjusted under 35 U.S.C. 154(b) by 862 days.

(21) Appl. No.: 17/295,656

(22) PCT Filed: Dec. 3, 2019

(86) PCT No.: PCT/US2019/064165
§ 371 (c)(1),
(2) Date: May 20, 2021

(87) PCT Pub. No.: WO2020/117755
PCT Pub. Date: Jun. 11, 2020

(65) Prior Publication Data
US 2022/0110897 A1    Apr. 14, 2022

Related U.S. Application Data

(60) Provisional application No. 62/774,737, filed on Dec. 3, 2018.

(51) Int. Cl.
*A61K 31/198*    (2006.01)
*A61K 47/10*    (2017.01)
*A61P 31/04*    (2006.01)

(52) U.S. Cl.
CPC ............ *A61K 31/198* (2013.01); *A61K 47/10* (2013.01); *A61P 31/04* (2018.01)

(58) Field of Classification Search
CPC ........ A61K 31/198; A61K 47/10; A61P 31/04
See application file for complete search history.

(56) References Cited

U.S. PATENT DOCUMENTS

| | | | |
|---|---|---|---|
| 3,922,202 A | 11/1975 | Hallada et al. | |
| 4,826,680 A | 5/1989 | Jaeger | |
| 4,871,550 A | 10/1989 | Millman | |
| 5,112,810 A | 5/1992 | Nagai et al. | |
| 5,366,723 A | 11/1994 | Tulok | |
| 5,711,937 A | 1/1998 | Nisiida et al. | |
| 5,811,446 A | 9/1998 | Thomas | |
| 5,872,127 A | 2/1999 | Cincotta et al. | |
| 6,103,748 A | 8/2000 | Bryan | |
| 6,274,612 B1 | 8/2001 | Bryan | |
| 7,906,544 B2 | 3/2011 | Melander et al. | |
| 8,241,611 B2 | 8/2012 | Dashper et al. | |
| 8,420,673 B2 | 4/2013 | Pasteris et al. | |
| 8,425,932 B2 | 4/2013 | Wryer et al. | |
| 8,980,307 B2 | 3/2015 | Harris et al. | |
| 9,370,486 B2 | 6/2016 | Chen | |
| 9,480,669 B2 * | 11/2016 | Bryan | A61K 31/405 |
| 9,549,904 B2 | 1/2017 | Bryan | |
| 9,732,164 B2 | 8/2017 | Baker et al. | |
| 11,382,885 B2 * | 7/2022 | Nobile | A61K 31/661 |
| 11,779,559 B2 * | 10/2023 | Nobile | A61L 29/16 |
| | | | 514/562 |
| 2004/0033959 A1 | 2/2004 | Chen et al. | |
| 2005/0064014 A1 | 3/2005 | Finot et al. | |
| 2011/0046041 A1 | 2/2011 | Neesham-Grenon et al. | |
| 2011/0236453 A1 | 9/2011 | Stensen et al. | |
| 2012/0004157 A1 | 1/2012 | Aksnes | |
| 2012/0315260 A1 | 12/2012 | Ivanova et al. | |
| 2013/0059096 A1 | 3/2013 | Losick et al. | |
| 2013/0071439 A1 | 3/2013 | Losick et al. | |
| 2013/0123319 A1 | 5/2013 | Bryan | |
| 2014/0018438 A1 | 1/2014 | Bryan | |
| 2014/0056951 A1 | 2/2014 | Losick et al. | |
| 2015/0126571 A1 | 1/2015 | Bryan | |
| 2017/0042851 A1 | 2/2017 | Bryan et al. | |
| 2018/0153840 A1 | 6/2018 | Bryan | |
| 2018/0214411 A1 | 8/2018 | Vetter | |
| 2020/0222349 A1 | 7/2020 | Nobile et al. | |
| 2022/0296553 A1 | 9/2022 | Nobile et al. | |
| 2024/0082195 A1 | 3/2024 | Nobile et al. | |

FOREIGN PATENT DOCUMENTS

| | | |
|---|---|---|
| GB | 2 514 863 A | 12/2014 |
| WO | WO-99/65479 A1 | 12/1999 |
| WO | WO-2011/085326 A1 | 7/2011 |
| WO | WO-2011/085326 A9 | 7/2011 |
| WO | WO-2016/112140 A1 | 7/2016 |
| WO | WO-2018/042367 A2 | 3/2018 |

(Continued)

OTHER PUBLICATIONS

Handbook of Pharmaceutical Excipients, Edited by Rowe et al., p. 637, para. 7 (Year: 2009).*
Handbook of Pharmaceutical Excipients (6th Ed) edited by Rowe et al., London: APhA (PhP) Pharmaceutical Press, pp. 637-640, Year: 2009.
Abd, M. et al. (2014). "N-acetylcysteine Inhibits and Eradicates Candida albicans Biofilms," *American J. Infectious Diseases and Microbiology* 2(5):122-130.
Fitzpatrick, F. et al. (Apr. 2005). "Evidence for icaADBC-independent biofilm development mechanism in methicillin-resistant *Staphylococcus aureus* clinical isolates," *J Clin Microbiol* 43(4):1973-1976.
Helms, S. et al. (2006). "Natural Treatment of Chronic Rhinosinusitis," *Alternative Medicine Review* 11(3):196-207.

(Continued)

*Primary Examiner* — Paul V Ward
(74) *Attorney, Agent, or Firm* — Mintz, Levin, Cohn, Ferris, Glovsky and Popeo, P.C.

(57) ABSTRACT

The disclosure provides compositions comprising amino acids, individually and in combination, and methods of making the compositions and methods of using the compositions as pharmaceutically active agents to, inter alia, treat disease in animals, including humans.

18 Claims, 9 Drawing Sheets

(56) References Cited

FOREIGN PATENT DOCUMENTS

| WO | WO-2018/042367 A3 | 3/2018 |
| WO | WO-2018/226987 A1 | 12/2018 |

OTHER PUBLICATIONS

International Search Report mailed on May 6, 2016, for PCT Application No. PCT/US2016/012395, filed Jan. 6, 2016, 4 pages.
International Search Report mailed on Aug. 28, 2018, for PCT Application No. PCT/US2018/036501, filed on Jun. 7, 2018, 4 pages.
International Search Report mailed on Feb. 10, 2020, for PCT Application No. PCT/US2019/064165, filed Dec. 3, 2019, 4 pages.
Percival, S.L. et al. (Jan.-Feb. 2008). "Assessing the effect of an antimicrobial wound dressing on biofilms," *Wound Repair Regen* 16(1):52-57.
Ponikau, J.U. et al. (Sep. 1999). "The diagnosis and incidence of allergic fungal sinusitis," *Mayo Clin Proc* 74(9):877-884.
Rona, Z. Naturally Savvy (2013). pp. 1-13.
Suh, J.D. et al. (Feb. 2010). "Biofilms in chronic rhinosinusitis," *Curr Opin Otolaryngol Head Neck Surg* 18(1):27-31.
Thomas, E.D. et al. (Sep. 12, 1957). "Intravenous Infusion of Bone Marrow in Patients Receiving Radiation and Chemotherapy," *The New England Journal of Medicine* 257(11):491-496.
Kenner, D. (Oct. 2007). Treatment of Infections Without Antibiotics, located at http://www.thenhf.com/old/articles/articles_594/articles_594.htm, 5 pages.
Tong, et al. (Jun. 2014). *PLoS One* 9(6):1-8.
Vale, N. et al. (Sep. 11, 2018). "Amino Acids in the Development of Prodrugs," *Molecules* 223(9):2318.
Written Opinion mailed on May 6, 2016, for PCT Application No. PCT/US2016/012395, filed Jan. 6, 2016, 9 pages.
Written Opinion mailed on Aug. 28, 2018, for PCT Application No. PCT/US2018/036501, filed on Jun. 7, 2018, 15 pages.
Written Opinion mailed on Feb. 10, 2020, for PCT Application No. PCT/US2019/064165, filed Dec. 3, 2019, 9 pages.
Drugs & Medications—Amino Acids-E-lyte-Glycerin IV; http://www.webmd.com/drugs/drug-63311-Amino+Acids-E-lyte-Glycerin+IV_aspx?drugid=63311&drugname=Amino+Acids-E-lyte-Glycerin+IV (2019).

\* cited by examiner

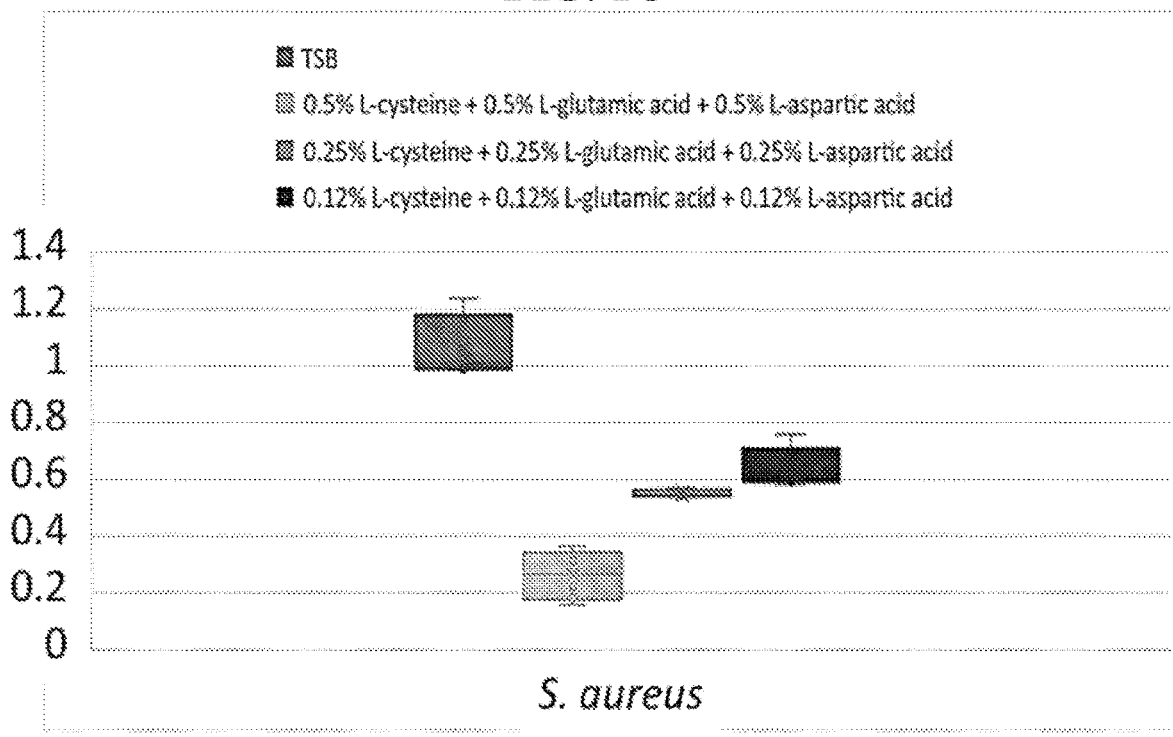
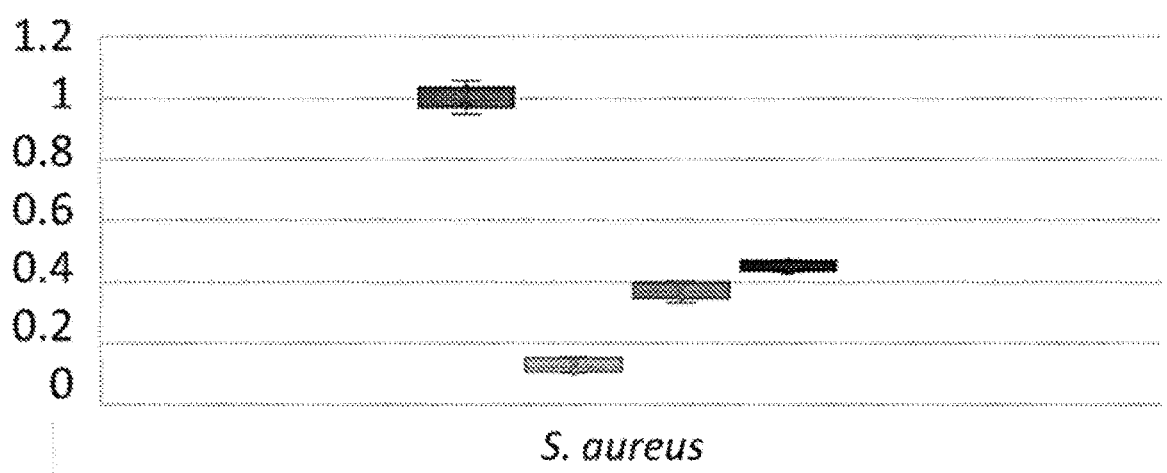

*C. albicans*

S. aureus

COMPOSITIONS AND METHODS FOR TREATING BIOFILMS

CROSS-REFERENCE TO RELATED APPLICATIONS

This application is a Section 371 US National Phase of International Application No. PCT/US2019/064165 filed Dec. 3, 2019, which claims priority to U.S. Application No. 62/774,737 filed Dec. 3, 2018, the disclosure of which is incorporated by reference herein.

STATEMENT REGARDING FEDERALLY SPONSORED RESEARCH OR DEVELOPMENT

This invention was made with government support under Grant No. R35GM124594 awarded by the National Institute of Health. The government has certain rights in the invention.

BACKGROUND

*Candida* spp. is the fourth leading cause of blood stream infections and the second most common cause of urinary tract infections. The success of fungus and bacteria in resisting most known antimicrobial agents can be attributed to their ability to produce biofilms. Microbes attach to surfaces and aggregate in hydrated polymeric matrices to form biofilms. Biofilms protect bacterial and fungal cells from the immune system and from antibiotics and antifungals.

According to the Center for Disease Control, 63% of treated bacterial infections develop biofilms and as such, biofilms are implicated in chronic infections. Most notable of these infections is *Staphylococcus aureus*, especially the methicillin-resistant variety. Furthermore, an estimated 13% of intensive care patients have a fungal infection likely originating from a biofilm.

SUMMARY

Chronic infections of both bacterial and fungal due to biofilms remain largely untreatable. Hence, there is a need for new antibacterial and antifungal agents. The present disclosure provides compounds, salts, compositions and uses thereof in the treatment of bacterial biofilm or fungal biofilms.

In certain aspects, the present disclosure provides a method of inhibiting or disrupting biofilm on a surface, the method comprising contacting the surface with a composition; wherein the composition comprises:
(i) one or more of a compound of formula (I) or a salt thereof;
(ii) one or more of a compound of formula (II) or a salt thereof; or
(iii) two or more of a compound of formula (I) or a salt thereof and a compound of formula (II) or a salt thereof;
wherein the compound of formula (I) is:

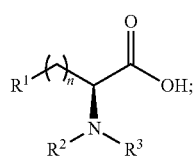

(I)

wherein the compound of formula (II) is:

(II)

wherein:
$R^1$ is —$SR^5$, —$C(O)OR^5$, or —$OP(=O)(OR^5)_2$;
$R^2$ and $R^3$ are hydrogen; or one of $R^2$ and $R^3$ is hydrogen, and the other of $R^2$ and $R^3$ with $R^1$ is taken together with the atoms to which they are attached to form a heterocycle substituted with one or more $R^6$;
$R^4$ is —$OR^5$, —$C(O)OR^5$, or —$OP(=O)(OR^5)_2$;
each $R^5$ is independently hydrogen, $C_{1-6}$ alkyl, $C_{2-6}$ alkenyl, $C_{2-6}$ alkynyl, $C_{3-12}$ carbocycle, or 3- to 12-membered heterocycle; each of which is independently and optionally substituted with one or more substituents selected from the group consisting of halogen, —CN, —$NO_2$, —OH, —$NH_2$, —COOH, and —$OCH_3$;
each $R^6$ is independently halogen, —$NO_2$, —CN, —$OR^5$, —$SR^5$, —$N(R^5)_2$, —$C(O)R^5$, —$C(O)OR^5$, —$OC(O)R^5$, —$OC(O)OR^5$, —$OC(O)N(R^5)_2$, —$NR^5C(O)R^5$, —$C(O)N(R^5)_2$, =O, =S, =$N(R^5)$, $C_{1-10}$ alkyl, $C_{2-10}$ alkenyl, or $C_{2-10}$ alkynyl; each of which is independently and optionally substituted with one or more substituents selected from the group consisting of halogen, —CN, —$NO_2$, —OH, —$NH_2$, —COOH, and —$OCH_3$; and
n and m are independently 0, 1, 2, 3, 4, or 5.

In certain aspects, the present disclosure provides a method of inhibiting or disrupting biofilm, the method comprising contacting a surface with a composition, wherein the composition comprising a compound of formula (I) or (II):

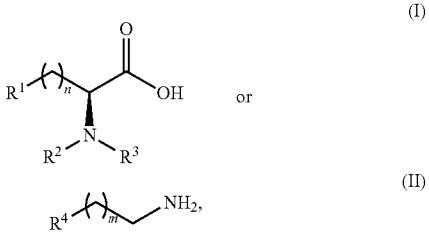

or a salt thereof, wherein: $R^1$ is selected from —$SR^5$, —$C(O)OR^5$, and —$OP(=O)(OR^5)_2$; $R^2$ and $R^3$ is hydrogen or, at least one of $R^2$ and $R^3$ is hydrogen and the other of $R^2$ and $R^3$ with $R^1$ is taken together with the atoms to which they are attached to form a heterocycle substituted with one or more $R^6$; $R^4$ is selected from —$OR^5$, —$C(O)OR^5$, and —$OP(=O)(OR^5)_2$; $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —$NO_2$, —OH, —$NH_2$, —COOH, and —$OCH_3$; $R^6$ is independently selected at each occurrence from halogen, —$NO_2$, —CN, —$OR^5$, —$SR^5$, —$N(R^5)_2$, —$C(O)R^5$, —$C(O)OR^5$, —$OC(O)R^5$, —$OC(O)OR^5$, —$OC(O)N(R^5)_2$, —$NR^5C(O)R^5$, —$C(O)N(R^5)_2$, =O, =S, =$N(R^5)$, $C_{1-10}$ alkyl, $C_{2-10}$ alkenyl, and $C_{2-10}$ alkynyl, each of which is independently optionally substituted at each occurrence with one or more substituents selected from halogen, —CN, —$NO_2$, —OH, —NH$_2$, —COOH, and —OCH$_3$; and n and m are independently selected from 0, 1, 2, 3, 4, or 5.

In certain aspects, the present disclosure provides a method of treating a bacterial or fungal infection in a subject in need thereof, the method comprising administering to the subject a composition comprising:
(i) one or more of a compound of formula (I) or a salt thereof;
(ii) one or more of a compound of formula (II) or a salt thereof; or
(iii) two or more of a compound of formula (I) or a salt thereof and a compound of formula (II) or a salt thereof;

wherein the compound of formula (I) is:

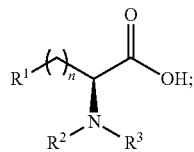
(I)

wherein the compound of formula (II) is:

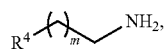
(II)

wherein:
R$^1$ is —SR$^5$, —C(O)R$^5$, —OC(O)R$^5$, —C(O)OR$^5$, —C(O)N(R$^5$)$_2$, —NR$^5$C(O), or —OP(=O)(OR$^5$)$_2$;
R$^2$ and R$^3$ are hydrogen; or one of R$^2$ and R$^3$ is hydrogen, and the other of R$^2$ and R$^3$ with R$^1$ is taken together with the atoms to which they are attached to form a heterocycle substituted with one or more R$^6$;
R$^4$ is —OR$^5$, —N(R$^5$)$_2$, —C(O)OR$^5$, —OC(O)R$^5$, C(O)N(R$^5$)$_2$, —NR$^5$C(O), or —OP(=O)(OR$^5$)$_2$;
each R$^5$ is independently hydrogen, C$_{1-6}$ alkyl, C$_{2-6}$ alkenyl, C$_{2-6}$ alkynyl, C$_{3-12}$ carbocycle, or 3- to 12-membered heterocycle; each of which is independently and optionally substituted with one or more substituents selected from the group consisting of halogen, —CN, —NO$_2$, —OH, —NH$_2$, —COOH, and —OCH$_3$;
each R$^6$ is independently halogen, —NO$_2$, —CN, —OR$^5$, —SR$^5$, —N(R$^5$)$_2$, —C(O)R$^5$, —C(O)OR$^5$, —OC(O)R$^5$, —OC(O)OR$^5$, —OC(O)N(R$^5$)$_2$, —NR$^5$C(O)R$^5$, —C(O)N(R$^5$)$_2$, =O, =S, =N(R$^5$), C$_{1-10}$ alkyl, C$_{2-10}$ alkenyl, or C$_{2-10}$ alkynyl; each of which is independently and optionally substituted at each occurrence with one or more substituents selected from the group consisting of halogen, —CN, —NO$_2$, —OH, —NH$_2$, —COOH, and —OCH$_3$; and n and m are independently 0, 1, 2, 3, 4, or 5.

In certain aspects, the present disclosure provides a method of treating a bacterial or fungal infection, the method comprising administering a composition comprising a compound of formula (I) or (II):

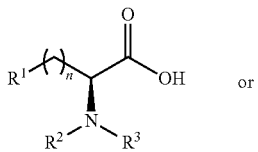
(I)

or

(II)

or a salt thereof, wherein: R$^1$ is selected from —SR$^5$, —C(O)R$^5$, —OC(O)R$^5$, —C(O)OR$^5$, —C(O)N(R$^5$)$_2$, —NR$^5$C(O), and —OP(=O)(OR$^5$)$_2$; R$^2$ and R$^3$ is hydrogen or, at least one of R$^2$ and R$^3$ is hydrogen and the other of R$^2$ and R$^3$ with R$^1$ is taken together with the atoms to which they are attached to form a heterocycle substituted with one or more R$^6$; R$^4$ is selected from —OR$^5$, —N(R$^5$)$_2$, —C(O)OR$^5$, —OC(O)R$^5$, C(O)N(R$^5$)$_2$, —NR$^5$C(O), and —OP(=O)(OR$^5$)$_2$; R$^5$ is independently selected at each occurrence from hydrogen; and C$_{1-6}$ alkyl, C$_{2-6}$ alkenyl, C$_{2-6}$ alkynyl, C$_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$; R$^6$ is independently selected at each occurrence from halogen, —NO$_2$, —CN, —OR$^5$, —SR$^5$, —N(R$^5$)$_2$, —C(O)R$^5$, —C(O)OR$^5$, —OC(O)R$^5$, —OC(O)OR$^5$, —OC(O)N(R$^5$)$_2$, —NR$^5$C(O)R$^5$, —C(O)N(R$^5$)$_2$, =O, =S, =N(R$^5$), C$_{1-10}$ alkyl, C$_{2-10}$ alkenyl, and C$_{2-10}$ alkynyl, each of which is independently optionally substituted at each occurrence with one or more substituents selected from halogen, —CN, —NO$_2$, —OH, —NH$_2$, —COOH, and —OCH$_3$; and n and m are independently selected from 0, 1, 2, 3, 4, or 5.

In embodiments, R$^1$ is selected from —SR$^5$, —C(O)OR$^5$, and —OP(=O)(OR$^5$)$_2$. In embodiments, R$^1$ is —SR$^5$. In embodiments, R$^5$ of R$^1$ is independently selected from hydrogen; and C$_{1-6}$ alkyl which is optionally substituted with halogen, —CN, —NO$_2$, —OH, —NH$_2$, —COOH, and —OCH$_3$. In embodiments, R$^5$ of R$^1$ is hydrogen. In embodiments, R$^5$ is independently selected from hydrogen; and C$_{1-6}$ alkyl which is optionally substituted with halogen, —CN, —NO$_2$, —OH, —NH$_2$, —COOH, and —OCH$_3$. In embodiments, R$^5$ is hydrogen. In embodiments, n is 1. In embodiments, n is 2. In embodiments, R$^5$ of R$^1$ is C$_2$ alkyl substituted with halogen, —CN, —NO$_2$, —OH, —NH$_2$, —COOH, or —OCH$_3$. In embodiments, R$^5$ of R$^1$ is C$_2$ alkyl substituted with —NH$_2$, and —COOH. In embodiments, R$^5$ is C$_2$ alkyl substituted with halogen, —CN, —NO$_2$, —OH, —NH$_2$, —COOH, or —OCH$_3$. In embodiments, R$^5$ is C$_2$ alkyl substituted with —NH$_2$, and —COOH.

In embodiments, R$^1$ is —C(O)OR$^5$. In embodiments, n is 1. In embodiments, n is 2. In embodiments, n is 3. In embodiments, R$^5$ of R$^1$ is independently selected from hydrogen; and C$_{1-6}$ alkyl which is optionally substituted with halogen, —CN, —NO$_2$, —OH, —NH$_2$, —COOH, and —OCH$_3$. In embodiments, R$^5$ of R$^1$ is hydrogen. In embodiments, R$^5$ of R$^1$ is C$_2$ alkyl substituted with halogen, —CN, —NO$_2$, —OH, —NH$_2$, —COOH, or —OCH$_3$. In embodiments, R$^5$ of R$^1$ is C$_2$ alkyl substituted with —NH$_2$, and —COOH. In embodiments, R$^5$ is C$_2$ alkyl substituted with halogen, —CN, —NO$_2$, —OH, —NH$_2$, —COOH, or —OCH$_3$. In embodiments, R$^5$ is C$_2$ alkyl substituted with —NH$_2$, and —COOH.

In embodiments, R$^1$ is —OP(=O)(OR$^5$)$_2$. In embodiments, R$^5$ is independently selected at each occurrence from hydrogen; and C$_{1-6}$ alkyl which is independently optionally substituted by halogen, —CN, —NO$_2$, —OH, —NH$_2$, —COOH, and —OCH$_3$. In embodiments, R$^5$ is independently selected at each occurrence from hydrogen; and C$_{1-6}$ alkyl. In embodiments, R$^5$ is selected at each occurrence from hydrogen. In embodiments, each R$^5$ of R$^1$ is independently selected from hydrogen; and C$_{1-6}$ alkyl which is independently and optionally substituted by one or more substituents selected from halogen, —CN, —NO$_2$, —OH, —NH$_2$, —COOH, and —OCH$_3$. In embodiments, each R$^5$ of R$^1$ is independently selected from hydrogen and C$_{1-6}$ alkyl. In embodiments, each R$^5$ of R$^1$ is hydrogen.

In embodiments, one of R$^2$ and R$^3$ is hydrogen, and the other of R$^2$ and R$^3$ with R$^1$ is taken together with the atoms to which they are attached to form a heterocycle substituted with one or more R$^6$. In embodiments, each R$^6$ is independently selected from halogen, —NO$_2$, —CN, —OR$^5$, —SR$^5$, and —N(R$^5$)$_2$. In embodiments, each R$^6$ is independently selected from halogen, —NO$_2$, —CN, and —OR$^5$. In embodiments, each R$^5$ of R$^6$ is hydrogen.

In embodiments, at least one of R$^2$ and R$^3$ is hydrogen and the other of R$^2$ and R$^3$ with R$^1$ is taken together with the atoms to which they are attached to form a heterocycle substituted with one or more R$^6$. In embodiments, R$^6$ is independently selected at each occurrence from halogen, —NO$_2$, —CN, —OR$^5$, —SR$^5$, —N(R$^5$)$_2$. In embodiments, R$^6$ is independently selected at each occurrence halogen, —NO$_2$, —CN, —OR$^5$. In embodiments, R$^5$ is hydrogen.

In embodiments, R$^4$ is selected from —OR$^5$, —C(O)OR$^5$, and —OP(=O)(OR$^5$)$_2$. In some embodiments, m is 1. In embodiments, n is 1. In embodiments, R$^4$ is —OR$^5$. In embodiments, R$^5$ of R$^4$ is hydrogen. In embodiments, R$^5$ is hydrogen. In embodiments, R$^4$ is —C(O)OR$^5$. In embodiments, R$^5$ is hydrogen. In embodiments, R$^4$ is —OP(=O)(OR$^5$)$_2$. In embodiments, each R$^5$ of R$^4$ is hydrogen.

In embodiments, the composition comprises cysteine, glutamic acid, aspartic acid, beta-alanine, 2-aminoadipic acid, cystathionine, ethanolamine, homocysteine, hydroxyproline, phosphoethanolamine, phosphoserine, salts thereof, or a combination of two or more of the foregoing. In embodiments, the composition comprises cysteine, glutamic acid, aspartic acid, beta-alanine, 2-aminoadipic acid, cystathionine, ethanolamine, homocysteine, hydroxyproline, phosphoethanolamine, phosphoserine, or salts thereof. In embodiments, the composition comprises cysteine or a salt thereof, glutamic acid or a salt thereof, and aspartic acid or a salt thereof. In embodiments, each of cysteine or a salt thereof, glutamic acid or a salt thereof, and aspartic acid or a salt thereof, are at a weight to volume percent from about 0.1% to about 5%. In embodiments, each of cysteine or a salt thereof, glutamic acid or a salt thereof, and aspartic acid or a salt thereof, are at a weight to volume percent from about 0.4% to about 0.6%. In embodiments, each of cysteine or a salt thereof, glutamic acid or a salt thereof, and aspartic acid or a salt thereof, are at a weight to volume percent of about 2%. In embodiments, each of cysteine or a salt thereof, glutamic acid or a salt thereof, and aspartic acid or a salt thereof, are at a weight to volume percent of about 0.5%. In embodiments, each of cysteine or a salt thereof, glutamic acid or a salt thereof, and aspartic acid or a salt thereof, are at a weight to volume percent of about 0.4%. In embodiments, each of cysteine or a salt thereof, glutamic acid or a salt thereof, and aspartic acid or a salt thereof, are at a weight to volume percent of about 0.6%.

In embodiments, the composition further comprises a pharmaceutically acceptable carrier. In embodiments, the pharmaceutically acceptable carrier is saline. In embodiments, the composition further comprises glycerin. In embodiments, the glycerin is at a weight to volume percentage of from about 0.1% to about 5%. In embodiments, the composition is free of alanine, arginine, asparagine, citrulline, glycine, isoleucine, leucine, lysine, methionine, 3-methylhistidine, phenylalanine, ornithine, proline, serine, taurine, threonine, tryptophan, valine, and pharmaceutically acceptable salts thereof. In embodiments, the composition is free of alanine, arginine, asparagine, citrulline, glycine, isoleucine, leucine, lysine, methionine, 3-methylhistidine, phenylalanine, ornithine, proline, serine, taurine, threonine, tryptophan, valine or pharmaceutically acceptable salts thereof.

In certain aspects, the present disclosure provides a composition comprising:
(i) one or more of a compound of formula (I) or a salt thereof;
(ii) one or more of a compound of formula (II) or a salt thereof; or
(iii) two or more of a compound of formula (I) or a salt thereof and a compound of formula (II) or a salt thereof;
wherein the compound of formula (I) is:

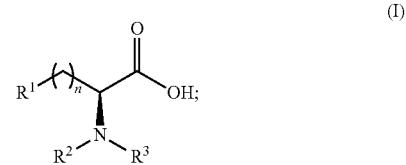

wherein the compound of formula (II) is:

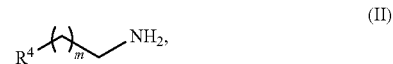

wherein:
R$^1$ is —SR$^5$, —C(O)OR$^5$, or —OP(=O)(OR$^5$)$_2$;
R$^2$ and R$^3$ are hydrogen; or one of R$^2$ and R$^3$ is hydrogen, and the other of R$^2$ and R$^3$ with R$^1$ is taken together with the atoms to which they are attached to form a heterocycle substituted with one or more R$^6$;
R$^4$ is —OR$^5$, —C(O)OR$^5$, or —OP(=O)(OR$^5$)$_2$;
each R$^5$ is independently hydrogen, C$_{1-6}$ alkyl, C$_{2-6}$ alkenyl, C$_{2-6}$ alkynyl, C$_{3-12}$ carbocycle, or 3 to 12 membered heterocycle; each of which is independently and optionally substituted with one or more substituents selected from the group consisting of halogen, —CN, —NO$_2$, —OH, —NH$_2$, —COOH, and —OCH$_3$;
each R$^6$ is independently halogen, —NO$_2$, —CN, —OR$^5$, —SR$^5$, —N(R$^5$)$_2$, —C(O)R$^5$, —C(O)OR$^5$, —OC(O)R$^5$, —OC(O)OR$^5$, —OC(O)N(R$^5$)$_2$, —NR$^5$C(O)R$^5$, —C(O)N(R$^5$)$_2$, =O, =S, =N(R$^5$), C$_{1-10}$ alkyl, C$_{2-10}$ alkenyl, or C$_{2-10}$ alkynyl; each of which is independently and optionally substituted with one or more substituents selected from the group consisting of halogen, —CN, —NO$_2$, —OH, —NH$_2$, —COOH, and —OCH$_3$; and
n and m are independently 0, 1, 2, 3, 4, or 5,
wherein (i), (ii), and (iii) demonstrate 10% or more inhibition in fungal or bacterial biofilm development relative to a comparison amino acid when subjected to a sustained inhibition assay comprising: (a) preparing samples with either the composition or the comparison amino acid in RPMI-1640 medium; (b) homogenizing samples with gentle agitation in the dark at 4° C. for 24 hours; (c) preparing saturated overnight cell cultures by streaking fungal strains on Yeast Peptone Dextrose agar plates; incubating at 30° C. for 48 hours; obtaining a single colony from each fungal strain; inoculating into Yeast Peptone Dextrose broth; and growing for 12 hours at 30° C. shaking at 225 rpm; (d) adding 1 µL of saturated overnight cell culture to 80 µL of samples in a 384-well plate; (e) allowing cells to adhere to the plate for 90 minutes at 37° C. shaking at 350 rpm; (f) washing loosely bound cells once with phosphate buffered saline and 80 µL of RPMI-1640; (g) incubating for a further 24 hours at 37° C. shaking at 350 rpm; (h) aspirating media and measure biofilm by optical density at 600 nm; (i) normalizing measurements to control experiment; (j) calculating inhibition in fungal biofilm development for the samples; and (k) comparing the value in step (j) of the composition with the value in step (j) of the comparison amino acid.

In certain aspects, the present disclosure provides a composition comprising a compound of formula (I) or (II):

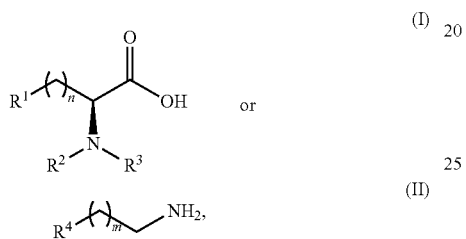

or a salt thereof, wherein: $R^1$ is selected from $-SR^5$, $-C(O)OR^5$, and $-OP(=O)(OR^5)_2$; $R^2$ and $R^3$ is hydrogen or, at least one of $R^2$ and $R^3$ is hydrogen and the other of $R^2$ and $R^3$ with $R^1$ is taken together with the atoms to which they are attached to form a heterocycle substituted with one or more $R^6$; $R^4$ is selected from $-OR^5$, $-C(O)OR^5$, and $-OP(=O)(OR^5)_2$; $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, $-CN$, $-NO_2$, $-OH$, $-NH_2$, $-COOH$, and $-OCH_3$; $R^6$ is independently selected at each occurrence from halogen, $-NO_2$, $-CN$, $-OR^5$, $-SR^5$, $-N(R^5)_2$, $-C(O)R^5$, $-C(O)OR^5$, $-OC(O)R^5$, $-OC(O)OR^5$, $-OC(O)N(R^5)_2$, $-NR^5C(O)R^5$, $-C(O)N(R^5)_2$, $=O$, $=S$, $=N(R^5)$, $C_{1-10}$ alkyl, $C_{2-10}$ alkenyl, and $C_{2-10}$ alkynyl, each of which is independently optionally substituted at each occurrence with one or more substituents selected from halogen, $-CN$, $-NO_2$, $-OH$, $-NH_2$, $-COOH$, and $-OCH_3$; and n and m are independently selected from 0, 1, 2, 3, 4, or 5, wherein the compound of formula (I) or (II) demonstrates 10% or more inhibition in fungal or bacterial biofilm development relative to a comparison amino acid when subjected to a sustained inhibition assay comprising: (a) preparing samples with either the composition or the comparison amino acid in RPMI-1640 medium; (b) homogenizing samples with gentle agitation in the dark at 4° C. for 24 hours; (c) preparing saturated overnight cell cultures by (i) streaking fungal strains on Yeast Peptone Dextrose agar plates; (ii) incubating at 30° C. for 48 hours; (iii) obtaining a single colony from each fungal strain; (iv) inoculating into Yeast Peptone Dextrose broth; and (v) growing for 12 hours at 30° C. shaking at 225 rpm; (e) adding 1 µL of saturated overnight cell culture to 80 µL of samples in a 384-well plate; (f) allowing cells to adhere to the plate for 90 minutes at 37° C. shaking at 350 rpm; (g) washing loosely bound cells once with phosphate buffered saline and 80 µL of RPMI-1640; (h) incubating for a further 24 hours at 37° C. shaking at 350 rpm; (i) aspirating media and measure biofilm by optical density at 600 nm; (j) normalizing measurements to control experiment; (k) calculating inhibition in fungal biofilm development for the samples; and (l) comparing the value in step (j) of the composition with the value in step (j) of the comparison amino acid.

In certain aspects, the present disclosure provides a composition comprising:
(i) one or more of a compound of formula (I) or a salt thereof;
(ii) one or more of a compound of formula (II) or a salt thereof; or
(iii) two or more of a compound of formula (I) or a salt thereof and a compound of formula (II) or a salt thereof;
wherein the compound of formula (I) is:

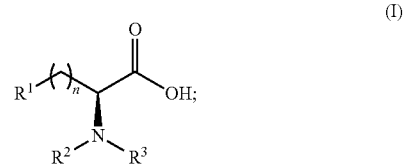

wherein the compound of formula (II) is:

wherein:
$R^1$ is $-SR^5$, $-C(O)OR^5$, or $-OP(=O)(OR^5)_2$;
$R^2$ and $R^3$ are hydrogen; or one of $R^2$ and $R^3$ is hydrogen, and the other of $R^2$ and $R^3$ with $R^1$ is taken together with the atoms to which they are attached to form a heterocycle substituted with one or more $R^6$;
$R^4$ is $-OR^5$, $-C(O)OR^5$, or $-OP(=O)(OR^5)_2$;
each $R^5$ is independently hydrogen, $C_{1-6}$ alkyl, $C_{2-6}$ alkenyl, $C_{2-6}$ alkynyl, $C_{3-12}$ carbocycle and 3- to 12-membered heterocycle; each of which is independently and optionally substituted with one or more substituents selected from the group consisting of halogen, $-CN$, $-NO_2$, $-OH$, $-NH_2$, $-COOH$, and $-OCH_3$;
each $R^6$ is independently halogen, $-NO_2$, $-CN$, $-OR^5$, $-SR^5$, $-N(R^5)_2$, $-C(O)R^5$, $-C(O)OR^5$, $-OC(O)R^5$, $-OC(O)OR^5$, $-OC(O)N(R^5)_2$, $-NR^5C(O)R^5$, $-C(O)N(R^5)_2$, $=O$, $=S$, $=N(R^5)$, $C_{1-10}$ alkyl, $C_{2-10}$ alkenyl, or $C_{2-10}$ alkynyl; each of which is independently and optionally substituted with one or more substituents selected from the group consisting of halogen, $-CN$, $-NO_2$, $-OH$, $-NH_2$, $-COOH$, and $-OCH_3$; and
n and m are independently 0, 1, 2, 3, 4, or 5;
wherein (i), (ii), and (iii) demonstrate 10% or more inhibition in fungal or bacterial biofilm development relative to a comparison amino acid when subjected to a sustained inhibition assay comprising: (a) preparing samples with either the composition or the comparison amino acid in RPMI-1640 medium; (b) homogenizing samples with gentle agitation in the dark at 4° C. for 24 hours; (c) preparing saturated overnight cell cultures by streaking fungal strains on Yeast Peptone Dextrose agar plates; incubating at 30° C. for 48 hours; obtaining a single colony from each fungal strain; inoculating into Yeast Peptone Dextrose broth; and growing for 12 hours at 30° C. shaking at 225 rpm; (d) adding 1 µL of saturated overnight cell culture to 80 µL of samples in a 384-well plate; (e) allowing cells to adhere to the plate for 90 minutes at 37° C. shaking at 350 rpm; (f) washing loosely bound cells once with phosphate buffered saline and 80 µL of RPMI-1640; (g) incubating for a further 24 hours at 37° C. shaking at 350 rpm; (h) aspirating media and measure biofilm by optical density at 600 nm; (i) normalizing measurements to control experiment; (j) calculating inhibition in fungal biofilm development for the samples; and (k) comparing the value in step (j) of the composition with the value in step (j) of the comparison amino acid.

In certain aspects, the present disclosure provides a composition comprising a compound of formula (I) or (II):

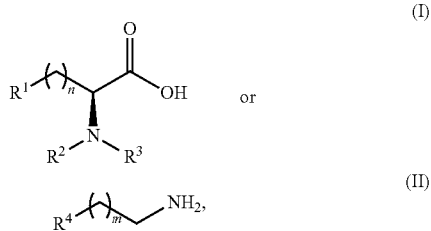

or a salt thereof, wherein: $R^1$ is selected from —$SR^5$, —C(O)$OR^5$, and —OP(=O)($OR^5$)$_2$; $R^2$ and $R^3$ is hydrogen or, at least one of $R^2$ and $R^3$ is hydrogen and the other of $R^2$ and $R^3$ with $R^1$ is taken together with the atoms to which they are attached to form a heterocycle substituted with one or more $R^6$; $R^4$ is selected from —$OR^5$, —C(O)$OR^5$, and —OP(=O)($OR^5$)$_2$; $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —$NO_2$, —OH, —$NH_2$, —COOH, and —$OCH_3$; $R^6$ is independently selected at each occurrence from halogen, —$NO_2$, —CN, —$OR^5$, —$SR^5$, —N($R^5$)$_2$, —C(O)$R^5$, —C(O)$OR^5$, —OC(O)$R^5$, —OC(O)$OR^5$, —OC(O)N($R^5$)$_2$, —$NR^5$C(O)$R^5$, —C(O)N($R^5$)$_2$, =O, =S, =N($R^5$), $C_{1-10}$ alkyl, $C_{2-10}$ alkenyl, and $C_{2-10}$ alkynyl, each of which is independently optionally substituted at each occurrence with one or more substituents selected from halogen, —CN, —$NO_2$, —OH, —$NH_2$, —COOH, and —$OCH_3$; and n and m are independently selected from 0, 1, 2, 3, 4, or 5, wherein the compound of formula (I) or (II) demonstrates 10% or more disruption in fungal or bacterial biofilm relative to a comparison amino acid when subjected to a disruption assay comprising: (a) preparing samples in RPMI 1640 medium; (b) homogenizing samples with gentle agitation in the dark at 4° C. for 24 hours; (c) preparing saturated overnight cell cultures by (i) streaking fungal strains on Yeast Peptone Dextrose agar plates; (ii) incubating at 30° C. for 48 hours; (iii) obtaining a single colony from each fungal strain; (iv) inoculating into Yeast Peptone Dextrose broth; and (v) growing for 12 hours at 30° C. shaking at 225 rpm; (d) adding 1 µL of saturated overnight cell culture to 80 µL of samples in a 384-well plate; (e) allowing cells to adhere to the plate for 90 minutes at 37° C. shaking at 350 rpm; (f) aspirating media from biofilm and add 80 µL more of samples; (g) incubating the plate for a further 24 hours at 37° C. shaking at 350 rpm; (h) aspirating media and measure biofilm by optical density at 600 nm; (i) normalizing measurements to control experiment; (j) calculating disruption in fungal biofilm for the samples; and (k) comparing the value in step j. of the composition with the value in step (j) of the comparison amino acid.

In embodiments, the composition comprises cysteine, glutamic acid, aspartic acid, beta-alanine, 2-aminoadipic acid, cystathionine, ethanolamine, homocysteine, hydroxyproline, phosphoethanolamine, phosphoserine or salts thereof, or a combination of two or more of the foregoing. In embodiments, the composition comprises at least two of cysteine, glutamic acid, aspartic acid, beta-alanine, 2-aminoadipic acid, cystathionine, ethanolamine, homocysteine, hydroxyproline, phosphoethanolamine, phosphoserine or salts thereof. In embodiments, the composition comprises at least two selected from the group consisting of cysteine, glutamic acid, aspartic acid, beta-alanine, 2-aminoadipic acid, cystathionine, ethanolamine, homocysteine, hydroxyproline, phosphoethanolamine, phosphoserine, and salts thereof. In embodiments, the composition is free of alanine, arginine, asparagine, citrulline, glycine, isoleucine, leucine, lysine, methionine, 3-methylhistidine, phenylalanine, ornithine, proline, serine, taurine, threonine, tryptophan, valine, and pharmaceutically acceptable salts thereof. In embodiments, the composition is free of alanine, arginine, asparagine, citrulline, glycine, isoleucine, leucine, lysine, methionine, 3-methylhistidine, phenylalanine, ornithine, proline, serine, taurine, threonine, tryptophan, valine, or pharmaceutically acceptable salts thereof.

In certain aspects, the disclosure provides a composition comprising cysteine or a salt thereof, glutamic acid or a salt thereof, aspartic acid or a salt thereof, and glycerin, wherein the cysteine is at a concentration of about 0.1% to about 5.0%. In embodiments, each of cysteine or a salt thereof, glutamic acid or a salt thereof, and aspartic acid or a salt thereof is at a concentration of about 0.1% to about 5%. In embodiments, each of cysteine or a salt thereof, glutamic acid or a salt thereof, and aspartic acid or a salt thereof is at a concentration of about 0.4% to about 0.6%. In embodiments, each of cysteine or a salt thereof, glutamic acid or a salt thereof, and aspartic acid or a salt thereof is at a concentration of about 2%. In embodiments, each of cysteine or a salt thereof, glutamic acid or a salt thereof, and aspartic acid or a salt thereof is at a concentration of about 0.5%. In embodiments, each of cysteine or a salt thereof, glutamic acid or a salt thereof, and aspartic acid or a salt thereof is at a concentration of about 0.4%. In embodiments, each of cysteine or a salt thereof, glutamic acid or a salt thereof, and aspartic acid or a salt thereof is at a concentration of about 0.6%. In embodiments, each of cysteine or a salt thereof, glutamic acid or a salt thereof, and aspartic acid or a salt thereof is at a concentration of about 0.5%. In embodiments, the composition further comprises at least one of beta-alanine, 2-aminoadipic acid, cystathionine, ethanolamine, homocysteine, hydroxyproline, phosphoethanolamine, phosphoserine, or salts thereof. In embodiments, the composition is essentially free of alanine, arginine, asparagine, citrulline, glycine, isoleucine, leucine, lysine, methionine, 3-methylhistidine, phenylalanine, ornithine, proline, serine, taurine, threonine, tryptophan, valine or pharmaceutically acceptable salts thereof. In embodiments, the composition is essentially free of alanine, arginine, asparagine, citrulline, glycine, isoleucine, leucine, lysine, methionine, 3-methylhistidine, phenylalanine, ornithine, proline, serine, taurine, threonine, tryptophan, valine, and pharmaceutically acceptable salts thereof. In embodiments, the composition is free of alanine, arginine, asparagine, citrulline, glycine, isoleucine, leucine, lysine, methionine, 3-methylhistidine, phenylalanine, ornithine, proline, serine, taurine, threonine, tryptophan, valine, and pharmaceutically acceptable salts thereof.

In certain aspects, the present disclosure provides a composition comprising an amino acid or a salt thereof, wherein the composition is essentially free of alanine, arginine, asparagine, citrulline, glycine, isoleucine, leucine, lysine, methionine, 3-methylhistidine, phenylalanine, ornithine, proline, serine, taurine, threonine, tryptophan, valine or pharmaceutically acceptable salts thereof. In embodiments, the composition is essentially free of alanine, arginine, asparagine, citrulline, glycine, isoleucine, leucine, lysine, methionine, 3-methylhistidine, phenylalanine, ornithine, proline, serine, taurine, threonine, tryptophan, valine, and pharmaceutically acceptable salts thereof. In embodiments, the composition is free of alanine, arginine, asparagine, citrulline, glycine, isoleucine, leucine, lysine, methionine, 3-methylhistidine, phenylalanine, ornithine, proline, serine, taurine, threonine, tryptophan, valine, and pharmaceutically acceptable salts thereof. In embodiments, the composition further comprises a pharmaceutically acceptable carrier. In embodiments, the pharmaceutically acceptable carrier is saline. In embodiments, the glycerin is at a weight to volume percentage of from ab out 0.1% to ab out 5%.

In certain aspects, the present disclosure provides a pharmaceutical composition in the form of an intravenous formulation comprising a composition as described herein. In certain aspects, the present disclosure provides a pharmaceutical composition in the form of a solution comprising a composition as described herein. In certain aspects, the present disclosure provides a pharmaceutical composition in the form of a douche comprising a composition as described herein.

In certain aspects, the present disclosure provides a composition comprising at least two of cysteine, glutamic acid, aspartic acid, beta-alanine, 2-aminoadipic acid, cystathionine, ethanolamine, homocysteine, hydroxyproline, phosphoethanolamine, phosphoserine, or salts thereof, wherein each cysteine, glutamic acid, aspartic acid, beta-alanine, 2-aminoadipic acid, cystathionine, ethanolamine, homocysteine, hydroxyproline, phosphoethanolamine, phosphoserine, or salts thereof is at a weight to volume percent from about 0.1% to about 5% and the composition is in the form of an intravenous formulation, a solution or a douche. In embodiments, the composition comprises at least two selected from the group consisting of cysteine, glutamic acid, aspartic acid, beta-alanine, 2-aminoadipic acid, cystathionine, ethanolamine, homocysteine, hydroxyproline, phosphoethanolamine, phosphoserine, and salts thereof; wherein each of the cysteine, glutamic acid, aspartic acid, beta-alanine, 2-aminoadipic acid, cystathionine, ethanolamine, homocysteine, hydroxyproline, phosphoethanolamine, phosphoserine, and salts thereof is at a weight to volume percent from about 0.1% to about 5% and the composition is in the form of an intravenous formulation, a solution or a douche. In embodiments, the composition further comprises glycerin. In embodiments, the composition comprises cysteine or a salt thereof, glutamic acid or a salt thereof, and aspartic acid or a salt thereof. In embodiments, each of cysteine or a salt thereof, glutamic acid or a salt thereof, and aspartic acid or a salt thereof are at a weight to volume percent of about 0.4%. In embodiments, each of cysteine or a salt thereof, glutamic acid or a salt thereof, and aspartic acid or a salt thereof are at a weight to volume percent of about 0.5%. In embodiments, each of cysteine or a salt thereof, glutamic acid or a salt thereof, and aspartic acid or a salt thereof are at a weight to volume percent of about 0.6%.

In embodiments, the composition is in the form of an intravenous formulation. In embodiments, the composition is in the form of a solution. In embodiments, the composition is in the form of a douche.

BRIEF DESCRIPTION OF THE DRAWINGS

The novel features of the disclosure are set forth with particularity in the appended claims. A better understanding of the features and advantages of the disclosure will be obtained by reference to the following detailed description that sets forth illustrative embodiments, in which the principles of the disclosure are utilized, and the accompanying drawings of which:

FIGS. 1A-1D show that a composition comprising cysteine, glutamic acid and aspartic acid may inhibit and disrupt biofilm formation in *C. albicans* and *S. aureus*. FIG. 1A shows sustained inhibition in *C. albicans* and FIG. 1B shows biofilm disruption in *C. albicans*. FIG. 1C shows sustained inhibition in *S. aureus* and FIG. 1D shows biofilm disruption in *S. aureus*.

FIG. 3A shows reduction of cell adherence in *C. albicans* by compositions of the disclosure. FIG. 3B shows inducement of cell death in *C. albicans* and *S. aureus* biofilms by compositions of the disclosure.

FIG. 5A shows inhibition and disruption of biofilm formation in *Candida* spp. FIG. 5B shows inhibition and disruption of biofilm formation in bacterial species.

DETAILED DESCRIPTION

Figure 1A:
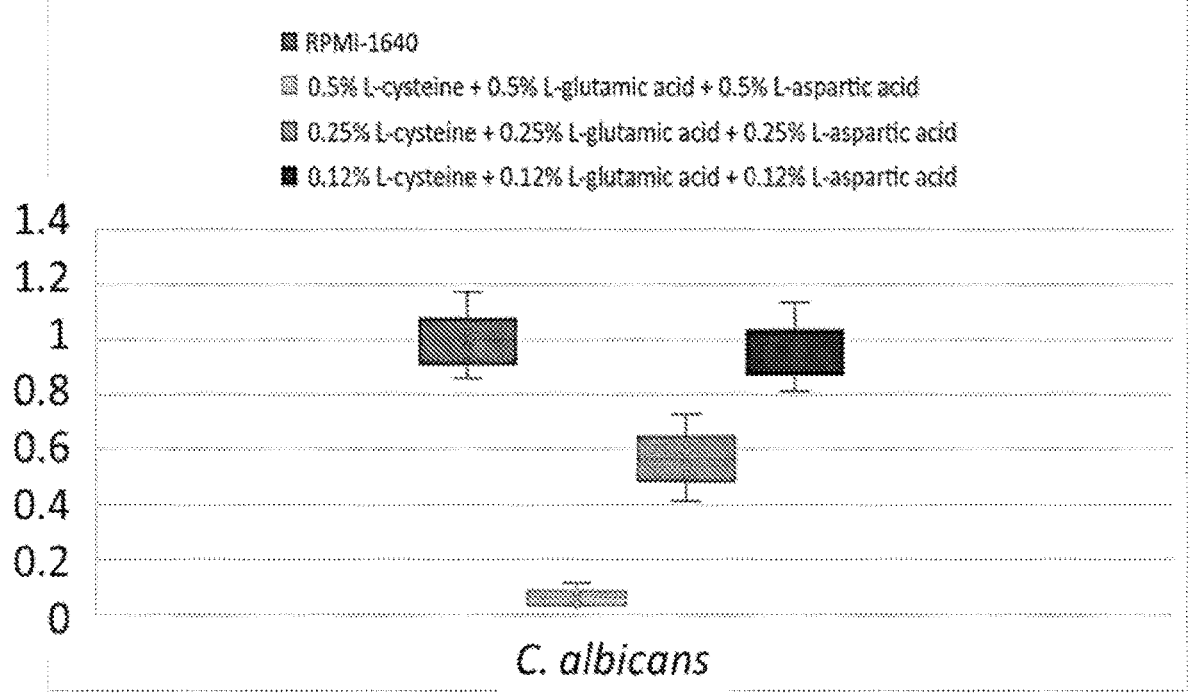

Over the last two decades, there has been a fundamental shift in how microbial growth is viewed. The classical perception that microbial species exist as free-floating planktonic cells has changed as research established that most microbial species exist in biofilms that may include a single species or multiple species (polymicrobial biofilms).

Biofilms are a community of cells adhered to a surface and often enclosed by an extracellular matrix. The protected mode of growth allows microbial cells to survive in hostile environments and makes them highly resistant to host defenses and antimicrobial drugs. The formation of these biofilms and their increased resistance may be the source of persistent and chronic microbial infections. The NIH estimates that 80% of infections are caused by pathogenic biofilms. Biofilms can form on form on both biotic (such as skin and mucosal surfaces) and abiotic surfaces (such as catheters and implanted medical devices).

The prevalence of these biofilms has major clinical implications, for instance, over half of the five million central venous catheters placed each year will develop a biofilm infection, despite the advances in clinical approaches. There are over 2 million nosocomial (hospital-acquired infections a year (~10% of American hospital patients) and 60-70% of these are associated with implanted medical devices, resulting in more than $5 billion in added medical cost per annum. Thus biofilm infections pose a significant medical burden, are expensive to combat and difficult to eradicate.

The most prevalent biofilm forming fungal pathogen is *Candida albicans*. *C. albicans* is a normal member of the human microbiome and can asymptomatically colonize several niches in the body. However in immunocompromised individuals, it can cause a host of infections ranging from superficial mucosal infections to disseminated bloodstream infections. The latter is associated with a high mortality rate of up to 70%.

In addition to the morbidity and mortality associated with systemic candidiasis, localized infections are a significant health issue. Approximately 70% of women experience vaginal infections caused by *Candida* spp., 20% of these women suffer from recurrent infections and of these latter recurrent infections, and about half of the patients have four or more episodes per year.

The success of *Candida albicans* as a human pathogen is a result of their diverse armamentarium of virulence factors. *C. albicans* colonizes mucosal surfaces, such as the gastrointestinal tract (isolated from over half of the oral cavities of healthy adults) and vaginal epithelium. *Candida* virulence is due to its ability to form biofilms, switch between different forms, and produce filaments in response to environmental conditions. *Candida* biofilm formation has important clinical repercussions because of their increased resistance to antifungal therapy and the ability of cells within biofilms to withstand host immune defenses, resulting in treatment failure and the need to remove catheters and other biological materials.

In several biofilm related infections, *C. albicans* is often co-isolated with the bacterial pathogen *Staphylococcus aureus*. Additionally, *S. aureus* is the leading bacterial cause of nosocomial infections. *S. aureus* can asymptomatically colonize nasal passages and studies indicate that there is a strong causal relationship between *S. aureus* nasal carriage and increased incidence of infections. *S. aureus* can cause acute infections, such as bacteremia and skin abscesses and chronic infections that persist on host tissues and are difficult to combat. Methicillin-resistant *S. aureus* has emerged as a significant threat in both hospital and community settings and due to limited treatment options, MRSA infections are associated with a high mortality rate of up to 50%.

Both *C. albicans* and MRSA can form strong biofilms on implanted medical devices, especially those used to administer fluids and nutrient such as intravascular or urinary catheter and endotracheal tubes. Surgically placed medical devices such as prosthetic heart valves, cardiac pacemakers and joint replacements are the most common places for biofilm formation and result in chronic infections. Additionally, non-device related abiotic surfaces such as acrylic dentures and contact lenses can also be a host to polymicrobial biofilms. In all cases, these biofilms display an increased resistance to physical stress, antifungals and antibiotics, often requiring a second surgery to remove and replace a device, when present on surgically placed devices. This is an added cost to patient's health, already suffering from the biofilm infection, and also results in increased medical costs to the healthcare system. Thus, there is an urgent need to seek new antimicrobial agents that can be used against both bacterial and fungal biofilm infections.

Virulence factors of both fungal and bacterial infections create an environment conducive to formation of biofilms. There are no effective treatments for either fungal or bacterial biofilms that can treat or prevent the formation of biofilms within a subject, or on an implanted device in a patient or within a catheter that is in fluid communication with a subject.

Definitions

Unless otherwise defined, all technical and scientific terms used herein have the same meaning as commonly understood by one of ordinary skill in the art. Methods and materials are described herein; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Various terms relating to the methods and other aspects of the disclosure are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein refers to a measurable value meant to encompass variations of ±20%, ±10%, ±5%, ±1%, ±0.5%, ±0.4%, ±0.3%, ±0.2%, ±0.1%, ±0.09%, ±0.08%, ±0.07%, ±0.06%, ±0.05%, ±0.04%, ±0.03%, ±0.02% or ±0.01% from the specified value "Alkyl" refers to a straight or branched hydrocarbon chain radical consisting solely of carbon and hydrogen atoms, containing no unsaturation, and preferably having from one to ten carbon atoms (i.e., $C_1$-$C_{10}$ alkyl). In embodiments, an alkyl comprises one to eight carbon atoms (i.e., $C_1$-$C_8$ alkyl). In embodiments, an alkyl comprises one to five carbon atoms (i.e., $C_1$-$C_8$ alkyl). In embodiments, an alkyl comprises one to four carbon atoms (i.e., $C_1$-$C_4$ alkyl). In embodiments, an alkyl comprises one to three carbon atoms (i.e., $C_1$-$C_3$ alkyl). In embodiments, an alkyl comprises one to two carbon atoms (i.e., $C_1$-$C_2$ alkyl). In embodiments, an alkyl comprises one carbon atom (i.e., $C_1$ alkyl). In embodiments, an alkyl comprises five to ten carbon atoms (i.e., $C_5$-$C_{10}$ alkyl). In embodiments, an alkyl comprises five to eight carbon atoms (i.e., $C_5$-$C_8$ alkyl). In embodiments, an alkyl comprises two to five carbon atoms (i.e., $C_2$-$C_5$ alkyl). In embodiments, an alkyl comprises three to five carbon atoms (i.e., $C_3$-$C_5$ alkyl). In embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (isobutyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more substituents such as those substituents described herein.

"Alkenyl" refers to a straight or branched hydrocarbon chain radical group consisting solely of carbon and hydrogen atoms, containing at least one carbon-carbon double bond, and preferably having from two to 10 carbon atoms (i.e., $C_2$-$C_{10}$ alkenyl). In embodiments, an alkenyl comprises two to eight carbon atoms (i.e., $C_2$-$C_8$ alkenyl). In embodiments, an alkenyl comprises two to six carbon atoms (i.e., $C_2$-$C_6$ alkenyl). The alkenyl may be attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to a straight or branched hydrocarbon chain radical group consisting solely of carbon and hydrogen atoms, containing at least one carbon-carbon triple bond, and preferably having from two to ten carbon atoms (i.e., $C_2$-$C_{10}$ alkynyl). In embodiments, an alkynyl comprises two to eight carbon atoms (i.e., $C_2$-$C_8$ alkynyl). In embodiments, an alkynyl comprises two to six carbon atoms (i.e., $C_2$-$C_6$ alkynyl). In embodiments, an alkynyl comprises two to four carbon atoms (i.e., $C_2$-$C_4$ alkynyl). The alkynyl may be attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents such as those substituents described herein.

The term "$C_{x-y}$" when used in conjunction with a chemical moiety, such as alkyl, alkenyl, or alkynyl is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain. The terms "$C_{x-y}$ alkenyl" and "$C_{x-y}$ alkynyl" refer to substituted or unsubstituted unsaturated aliphatic groups analogous in length and possible substitution to the alkyls described above, but that contain at least one double or triple bond respectively.

"Carbocycle" refers to saturated, unsaturated or aromatic rings in which each atom of the ring is carbon. Carbocycle may be monocyclic or polycyclic and may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In embodiments, the carbocycle is an aryl. In embodiments, the carbocycle is a cycloalkyl. In embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising carbon atoms and one or more heteroatoms in the ring. Exemplary heteroatoms include N, O, Si, P, B, and S atoms. Heterocycle may be monocyclic or polycyclic and may include 3- to 10-membered halogen monocyclic rings, 6- to 12-membered bicyclic rings, and 6- to 12-membered bridged rings. For a polycyclic heterocycle, at least one ring of the polycycle includes a heteroatom in the ring. Each ring of a bicyclic heterocycle may be selected from saturated, unsaturated, and aromatic rings. In embodiments, the heterocycle is a heteroaryl. In embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene. Unless stated otherwise specifically in the specification, a heterocycle is optionally substituted by one or more substituents such as those substituents described herein.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$_b$—OR$_a$, —R$_b$—OC(O)—R$_a$, —R$_b$—OC(O)—OR$_a$, —R$_b$—OC(O)—N(R$_a$)$_2$, —R$_b$—N(R$_a$)$_2$, —R$_b$—C(O)R$_a$, —R$_b$—C(O)OR$_a$, —R$_b$—C(O)N(R$_a$)$_2$, —R$_b$—O—R$_c$—C(O)N(R$_a$)$_2$, —R$_b$—N(R$_a$)C(O)OR$_a$, —R$_b$—N(R$_a$)C(O)R$_a$, —R$_b$—N(R$_a$)S(O)$_t$R$_a$ (where t is 1 or 2), —R$_b$—S(O)$_t$R$_a$ (where t is 1 or 2), —R$_b$—S(O)$_t$OR$_a$ (where t is 1 or 2), and —R$_b$—S(O)$_t$N(R$_a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$_b$—OR$_a$, —R$_b$—OC(O)—R$_a$, —R$_b$—OC(O)—OR$_a$, —R$_b$—OC(O)—N(R$_a$)$_2$, —R$_b$—N(R$_a$)$_2$, —R$_b$—C(O)R$_a$, —R$_b$—C(O)OR$_a$, —R$_b$—C(O)N(R$_a$)$_2$, —R$_b$—O—R$_c$—C(O)N(R$_a$)$_2$, —R$_b$—N(R$_a$)C(O)OR$_a$, —R$_b$—N(R$_a$)C(O)R$_a$, —R$_b$—N(R$_a$)S(O)$_t$R$_a$ (where t is 1 or 2), —R$_b$—S(O)$_t$R$_a$ (where t is 1 or 2), —R$_b$—S(O)$_t$OR$_a$ (where t is 1 or 2) and —R$_b$—S(O)$_t$N(R$_a$)$_2$ (where t is 1 or 2); wherein each R$_a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$_a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$_b$—OR$_a$, —R$_b$—OC(O)—R$_a$, —R$_b$—OC(O)—OR$_a$, —R$_b$—OC(O)—N(R$_a$)$_2$, —R$_b$—N(R$_a$)$_2$, —R$_b$—C(O)R$_a$, —R$_b$—C(O)OR$_a$, —R$_b$—C(O)N(R$_a$)$_2$, —R$_b$—O—R$_c$—C(O)N(R$_a$)$_2$, —R$_b$—N(R$_a$)C(O)OR$_a$, —R$_b$—N(R$_a$)C(O)R$_a$, —R$_b$—N(R$_a$)S(O)$_t$R$_a$ (where t is 1 or 2), —$R_b$—S(O)$_t$$R_a$ (where t is 1 or 2), —$R_b$—S(O)$_t$O$R_a$ (where t is 1 or 2) and —$R_b$—S(O)$_t$N($R_a$)$_2$ (where t is 1 or 2); and wherein each $R_b$ is independently selected from a direct bond or a straight or branched alkylene, alkenylene, or alkynylene chain, and each Reis a straight or branched alkylene, alkenylene or alkynylene chain.

The compounds disclosed herein, in embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). When the compounds described herein can form tautomers, and unless specified otherwise, all tautomeric forms are also intended to be included. The term "geometric isomer" refers to E or Z geometric isomers (e.g., cis or trans) of an alkene double bond.

A "tautomer" refers to a molecule wherein a proton shift from one atom of a molecule to another atom of the same molecule is possible. The compounds presented herein, in embodiments, exist as tautomers. In circumstances where tautomerization is possible, a chemical equilibrium of the tautomers will exist. Unless otherwise stated, chemical structures depicted herein are intended to include structures which are different tautomers of the structures depicted. For example, the chemical structure depicted with an enol moiety also includes the keto tautomer form of the enol moiety. The exact ratio of the tautomers depends on several factors, including physical state, temperature, solvent, and pH. Some examples of tautomeric equilibrium include:

deuteration can improve the metabolic stability and or efficacy, thus increasing the duration of action of drugs.

The compounds of the present disclosure optionally contain unnatural proportions of atomic isotopes at one or more atoms that constitute such compounds. For example, the compounds may be labeled with isotopes, such as deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds, whether radioactive or not, are encompassed within the scope.

The term "active state" refers to the conformation or set of conformations of a polypeptide or amino acid that allows functional domain or domains of the polypeptide or amino acid to associate or disassociate with another compound, macromolecule, or ligand. In embodiments, the association or disassociation of the polypeptide or amino acid with another compound, macromolecule, or ligand may propagate or inhibit a biologic signal propagated by the bacterial species or fungal species colonized or growing on a surface and/or in a subject.

The term "administering" or "administration" and the like, refers to providing a compound, salt or composition described herein to a subject in need of treatment. Preferably the subject is a mammal, such as a human. Administration of a compound, salt or composition described herein may be in conjunction with another active ingredient. When a compound, salt or composition described herein is administered in conjunction with another active ingredient, the compound, salt or composition and the other active ingredient may be administered simultaneously in the same composition, simultaneously in different dosage forms or sequentially or at different times. When a compound, salt or

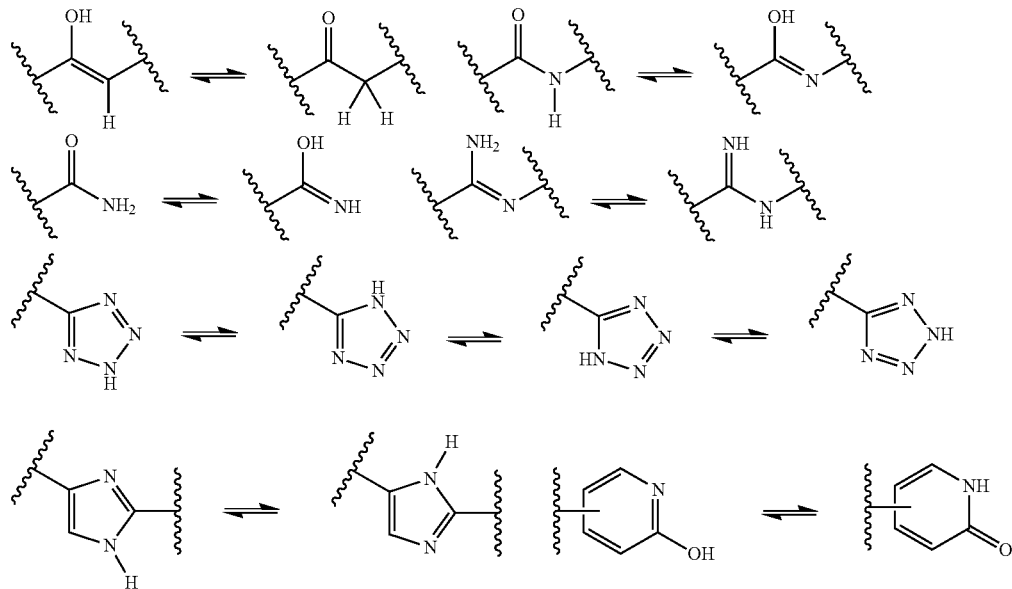

The compounds disclosed herein, in embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, composition described herein and another active ingredient are administered at the same time, they may be administered as a single composition or as separate compositions. When a compound, salt or composition described herein is administered in conjunction with another active ingredient, these may be administered as a single combination or in multiple combinations. For example, when administered intravenously, a compound, salt or composition describe herein may be dissolved or suspended in a commonly used intravenous fluids and administered by infusion, and then the other active ingredient may be dissolved or suspended in a commonly used intravenous fluid and administered by infusion. Conversely, the other active ingredient may be dissolved or suspended in a commonly used intravenous fluid and administered by infusion, and then a compound, salt or composition described herein may be dissolved or suspended in a commonly used intravenous fluid and administered by infusion. Alternatively, a compound, salt or composition described herein and another active ingredient may be dissolved or suspended in a commonly used intravenous fluid and administered by infusion.

The term "amino acid" refers to a molecule containing both an amino group and a carboxyl group bound to a carbon which is designated an α-carbon. "Amino acid" also refers to or includes, without limitation, both the D- and L-isomers of the naturally-occurring amino acids, as well as non-naturally occurring amino acids prepared by organic synthesis or other metabolic routes. A single "amino acid" may have multiple sidechains moieties, as available per an extended aliphatic or aromatic backbone scaffold. An "amino acid" also refers to a molecule with non-natural side chains. Unless the context specifically indicates otherwise, the term "amino acid", as used herein, is intended to include amino acid analogs. These include, but are not limited to L-isomers, combinations of L-isomers with other non-natural amino acids, D-isomers of any naturally occurring non-bonded amino acid or salts thereof, an amino acid modified with non-natural chemical substituents on its side chain and/or amino terminus and/or carboxy terminus, and isomers or optical isomers of natural amino acids.

As used herein, the term "derived from" in the context of the relationship between a chemical structure and a related chemical structure describes a chemical structure that may be homologous to or structurally similar to the related chemical structure. For instance, norleucine is an amino acid derived from leucine because it comprises a chemical formula substantively based upon the chemical formula of leucine.

As used herein "therapeutically effective amount" refers to an amount of a compound, material, or composition, as described herein effective to achieve a particular biological result such as, but not limited to, biological results disclosed, described, or exemplified herein. Such results may include, but are not limited to, the effective reduction of signs and symptoms associated with any bacterial or fungal infection of the disease states mentioned herein, as determined by any means suitable in the art. Such results may include, but are not limited to, the effective disruption of bacterial biofilm growth or maintenance, the effective disruption of fungal biofilm growth or maintenance, or the reduction of clinically relevant numbers of bacterial or fungal cells at or proximate to the surface of an implanted or non-implanted medical device or surface intended to be sterile. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be determined by those of skill in the art using optimization techniques and the skilled and informed judgment of the practitioner. A therapeutically effective amount of a compound, salt or composition described herein may provide partial or complete cure or resolution of signs and symptoms associated with the bacterial or fungal infections of a subject being treated as compared to the signs and symptoms or infection of a subject infected by the bacterial or fungal species disclosed herein who is untreated. A therapeutically effective dose of the compound, salt or composition described herein may provide a sustained biochemical or biological effect and/or an increased resistance to bacterial or fungal infection or biofilm formation when administered to a subject as compared to the same subject were it left untreated.

The term "non-bonded" amino acid encompasses a single amino acid or pharmaceutically acceptable salt thereof with a free amino or carboxy group not covalently bound to another molecule or chemical substance. Examples of a non-bonded amino acid are, but are not limited to, a naturally occurring amino acid or a non-naturally occurring amino acid in a solid dosage form or liquid dosage form that is not covalently bound to a molecule or chemical substance, a naturally occurring amino acid or a non-naturally occurring amino acid complexed with a buffer, salt or other small chemical compound, but not integrated within a polypeptide, a naturally occurring amino acid or non-naturally occurring amino acid bound to a chemical group or substituent that when administered to a surface or a subject and exposed to a pharmacologically active substance (environmentally available or physiologically available in a subject) is cleaved to form the free naturally occurring amino acid or non-naturally occurring amino acid. "Non-bonded" forms of the amino acids described herein include those prodrug forms that may or may not have a cleavable substituent that, under therapeutically effective conditions, cleaved from the amino acid or amino acids in the composition.

A "non-natural side chain" is a modified or synthetic chain of atoms joined by a covalent bond to the α-carbon atom, β-carbon atom, or γ-carbon atom which does not make up the backbone of the polypeptide chain of amino acids. The natural side chain, or R group, of alanine is a methyl group. In embodiments, the non-natural side chain of the composition is a methyl group in which one or more of the hydrogen atoms is replaced by a deuterium atom.

The term "polypeptide" encompasses two or more naturally or non-naturally-occurring amino acids joined by a covalent bond (e.g., an amide bond). Polypeptides as described herein include full-length proteins (e.g., fully processed pro-proteins or full-length synthetic polypeptides) as well as shorter amino acid sequences (e.g., fragments of naturally-occurring proteins or synthetic polypeptide fragments) that comprise or are free of carbohydrate modifications.

The term "salt" refers to acidic salts formed with inorganic and/or organic acids, as well as basic salts formed with inorganic and/or organic bases. Such acid addition salts will be pharmaceutically acceptable although salts of non-pharmaceutically acceptable acids may be of utility in the preparation and purification of the compound in question. Salts of the embodiments include those formed from hydrochloric, hydrobromic, sulphuric, phosphoric, citric, tartaric, lactic, pyruvic, acetic, succinic, fumaric, maleic, methane-sulphonic, benzenesulphonic, nitric and benzoic acids.

In embodiments, salts described herein may be formed by reacting the free base, or a salt, enantiomer or racemate thereof, with one or more equivalents of the appropriate acid. In embodiments, pharmaceutically acceptable salts refer to salts having at least one basic group or at least one basic radical. In embodiments, pharmaceutically acceptable salts comprise a free amino group, a free guanidino group, a pyrazinyl radical, or a pyridyl radical that forms acid addition salts. In embodiments, the pharmaceutically acceptable salts refer to salts which are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In embodiments, the salts may be those that are physiologically tolerated by a patient. Salts described herein can be in their anhydrous form or in hydrated crystalline form (i.e., complexed or crystallized with one or more molecules of water).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier is "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "soluble" or "water soluble" refers to solubility that is higher than 1/100,000 (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is 1/10,000 (mg/ml) or less. Water soluble or soluble substances include, for example, polyethylene glycol. In embodiments, the modified or natural amino acid may be bound by polyethylene glycol to better solubilize the composition comprising the peptide or the amino acids. In embodiments, the solubility of a modified or natural amino acid may be influenced by excipients. Such excipients may be selected from the group consisting of dimethyl acetamide, povidone, poloxamer, and bovine serum albumin.

The term "subject" is used throughout the specification to describe an animal to whom treatment with is provided or administered to. For treatment of those conditions, such as a human being, the term "patient" may be interchangeably used. In embodiments, the term "patient" refers to human patients. In embodiments, the subject may be a mammal. In embodiments, the subject may be a non-mammalian animal. In embodiments, the subject is a domesticated mammal such as a canine, equine, feline, porcine, bovine, murine, caprine, ovine, or other domesticated mammal. In embodiments, the subject is a human.

As used herein, the term "oral transmucosal delivery" (OTD) refers to the delivery of a pharmaceutical agent across a mucous membrane in the oral cavity, pharyngeal cavity, or esophagus, and may be contrasted, for example, with traditional oral delivery, in which absorption of the drug occurs in the intestines. Accordingly, routes of administration in which the pharmaceutical agent is absorbed through the buccal, sublingual, gingival, pharyngeal, and/or esophageal mucosa are all encompassed within "oral transmucosal delivery," as that term is used herein. Oral transmucosal delivery involves the administration of an oral transmucosal solid dosage form to the oral cavity of a patient, which is held in the oral cavity and dissolved, thereby releasing the pharmaceutical agent for oral transmucosal delivery.

The term "surface" is used throughout the specification to describe an area of a device, apparatus, or system upon which fungal biofilm or bacterial biofilm may grow. In embodiments, the device is a catheter. In embodiments, the device is implanted in a subject. In embodiments, the device is selected from the group consisting of a catheter, a valve, a prosthesis, ventricular assist devices, pulmonary devices, and ventilators (e.g. CPAP).

The terms "treating" and "to treat," mean to alleviate signs and/or symptoms, eliminate the causation either on a temporary or permanent basis, or to prevent or slow the appearance of symptoms. The term "treatment" includes alleviation, elimination of causation (temporary or permanent) of, or prevention of signs and/or symptoms and disorders associated with any condition, such as a fungal infection, bacterial infection, or either of those types of infections comprising microorganisms in the form of a biofilm. The treatment may be a pre-treatment (as a preventative treatment) and/or treatment at the onset of signs and/or symptoms.

Compounds and Compositions

The present disclosure provides compounds and salts thereof for the treatment of bacterial or fungal biofilms. In embodiments, the compounds of the disclosure, and salts thereof, disrupt the formation of bacterial or fungal biofilms. In embodiments, the compounds of the disclosure, and salts thereof, inhibit the formation of bacterial or fungal biofilms. Compounds of the disclosure, and salts thereof may be used in the formulations, methods and combination therapies described herein. In embodiments, compounds and salts of the disclosure are used in the treatment of bacterial or fungal infections.

In embodiments, the compound of the disclosure, or salt thereof demonstrates inhibition of fungal or bacterial biofilms greater than a comparison amino acid. For example, the compound of the disclosure, or salt thereof, demonstrates 10% or more, 20% or more, 30% or more, 40% or more, 50% or more, 60% or more, 70% or more, from 10% to 80%, from 10% to 70%, from 10% to 60%, or from 10% to 50% greater disruption of fungal or bacterial biofilms greater than a comparison amino acid.

In embodiments, the compound of the disclosure, or salts thereof, demonstrates disruption of fungal or bacterial biofilms greater than a comparison amino acid. For example, the compound of the disclosure, or salt thereof, demonstrates 10% or more, 20% or more, 30% or more, 40% or more, 50% or more, 60% or more, 70% or more, from 10% to 80%, from 10% to 70%, from 10% to 60%, or from 10% to 50% greater disruption of fungal or bacterial biofilms greater than a comparison amino acid.

In embodiments, a compound of the disclosure is represented by Formula (I) or Formula

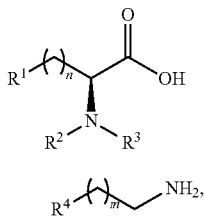

or a salt of any one thereof, wherein: $R^1$ is selected from —$SR^5$, —C(O)$OR^5$, and —OP(=O)($OR^5$)$_2$; $R^2$ and $R^3$ is hydrogen or, at least one of $R^2$ and $R^3$ is hydrogen and the other of $R^2$ and $R^3$ with $R^1$ is taken together with the atoms to which they are attached to form a heterocycle substituted with one or more $R^6$; $R^4$ is selected from —$OR^5$, —C(O)$OR^5$, and —OP(=O)($OR^5$)$_2$; $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$; $R^6$ is independently selected at each occurrence from halogen, —NO$_2$, —CN, —$OR^5$, —$SR^5$, —N($R^5$)$_2$, —C(O)$R^5$, —C(O)$OR^5$, —OC(O)$R^5$, —OC(O)$OR^5$, —OC(O)N($R^5$)$_2$, —$NR^5$C(O)$R^5$, —C(O)N($R^5$)$_2$, =O, =S, =N($R^5$), $C_{1-10}$ alkyl, $C_{2-10}$ alkenyl, and $C_{2-10}$ alkynyl, each of which is independently optionally substituted at each occurrence with one or more substituents selected from halogen, —CN, —NO$_2$, —OH, —NH$_2$, —COOH, and —OCH$_3$; and n and m are independently selected from 0, 1, 2, 3, 4, or 5.

For a compound or salt of Formula (I), $R^1$ may be selected from —$SR^5$, —C(O)$OR^5$, and —OP(=O)($OR^5$)$_2$. For a compound or salt of Formula (I), $R^1$ may be —$SR^5$. For a compound or salt of Formula (I), when $R^1$ is —$SR^5$, then $R^5$ is selected from hydrogen; and $C_{1-6}$ alkyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt of Formula (I), when $R^1$ is —$SR^5$, then $R^5$ is selected from hydrogen; and $C_{1-6}$ alkyl which is optionally substituted at each occurrence by halogen, —CN, —NO$_2$, —OH, —NH$_2$, —COOH, and —OCH$_3$.

For a compound or salt of Formula (I), $R^1$ may be —SH. For a compound or salt of Formula (I), $R^1$ may be selected from:

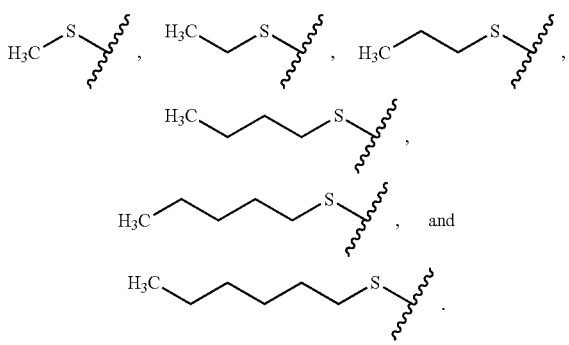

For a compound or salt of Formula (I), $R^1$ may be selected from:

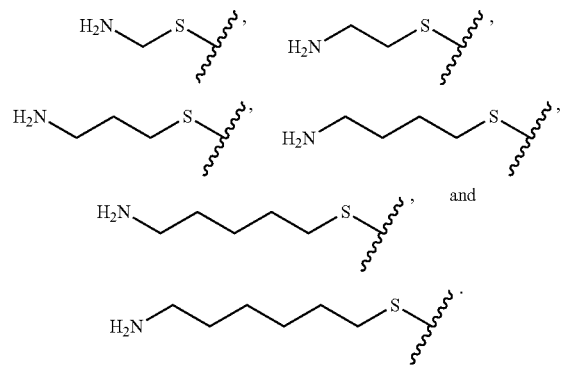

For a compound or salt of Formula (I), $R^1$ may be selected from:

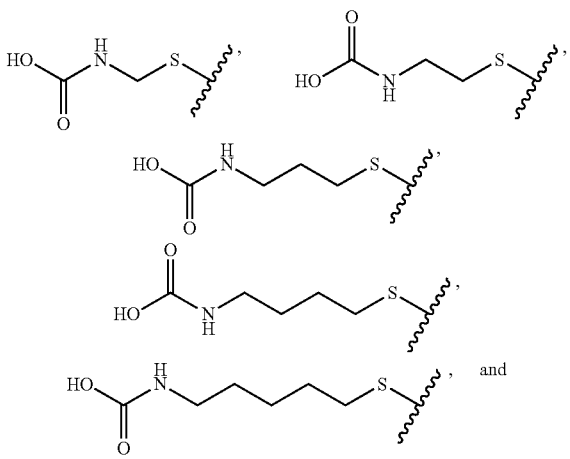

-continued

HO-C(O)-NH-(CH2)6-S-~~~

For a compound or salt of Formula (I), $R^1$ may be —C(O)OR$^5$. For a compound or salt of Formula (I), when $R^1$ is —C(O)OR$^5$, then $R^5$ is selected from hydrogen; and $C_{1-6}$ alkyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt of Formula (I), when $R^1$ is —C(O)OR$^5$, then $R^5$ is selected from hydrogen; and $C_{1-6}$ alkyl which is optionally substituted at each occurrence by halogen, —CN, —NO$_2$, —OH, —NH$_2$, —COOH, and —OCH$_3$. For a compound or salt of Formula (I), when $R^1$ is —C(O)OR$^5$, then $R^5$ is selected from hydrogen; and $C_{1-6}$ alkyl which is substituted at each occurrence by halogen, —CN, —NO$_2$, —OH, —NH$_2$, —COOH, and —OCH$_3$. For a compound or salt of Formula (I), when $R^1$ is —C(O)OR$^5$, then $R^5$ is selected from hydrogen; and $C_{1-6}$ alkyl. For a compound or salt of Formula (I), $R^1$ may be C(O)OH.

For a compound or salt of Formula (I), $R^1$ may be —OP(=O)(OR$^5$)$_2$. For a compound or salt of Formula (I), when $R^1$ is —OP(=O)(OR$^5$)$_2$, then $R^5$ is selected from hydrogen; and $C_{1-6}$ alkyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt of Formula (I), when $R^1$ is —OP(=O)(OR$^5$)$_2$, then $R^5$ is selected from hydrogen; and $C_{1-6}$ alkyl which is optionally substituted at each occurrence by halogen, —CN, —NO$_2$, —OH, —NH$_2$, —COOH, and —OCH$_3$. For a compound or salt of Formula (I), when $R^1$ is —OP(=O)(OR$^5$)$_2$, then $R^5$ is selected from hydrogen; and $C_{1-6}$ alkyl which is substituted at each occurrence by halogen, —CN, —NO$_2$, —OH, —NH$_2$, —COOH, and —OCH$_3$. For a compound or salt of Formula (I), when $R^1$ is —OP(=O)(OR$^5$)$_2$, then $R^5$ is selected from hydrogen; and $C_{1-6}$ alkyl. For a compound or salt of Formula (I), $R^1$ may be —OP(=O)(OH)$_2$.

For a compound or salt of Formula (I), at least one of $R^2$ and $R^3$ may be hydrogen and the other of $R^2$ and $R^3$ with $R^1$ may be taken together with the atoms to which they are attached to form a heterocycle substituted with one or more $R^6$. For a compound or salt of Formula (I), at least one of $R^2$ and $R^3$ may be hydrogen and the other of $R^2$ and $R^3$ with $R^1$ may be taken together with the atoms to which they are attached to form a 5-membered heterocycle substituted with one or more $R^6$. For a compound or salt of Formula (I), at least one of $R^2$ and $R^3$ may be hydrogen and the other of $R^2$ and $R^3$ with $R^1$ may be taken together with the atoms to which they are attached to form a 6-membered heterocycle substituted with one or more $R^6$. For a compound or salt of Formula (I), at least one of $R^2$ and $R^3$ may be hydrogen and the other of $R^2$ and $R^3$ with $R^1$ may be taken together with the atoms to which they are attached to form a 7-membered heterocycle substituted with one or more $R^6$.

For a compound or salt of Formula (I), when at least one of $R^2$ and $R^3$ is hydrogen and the other of $R^2$ and $R^3$ with $R^1$ is taken together with the atoms to which they are attached to form a heterocycle substituted with one or more $R^6$, $R^6$ may be independently selected at each occurrence from halogen, —NO$_2$, —CN, —OR$^5$, —SR$^5$, —N(R$^5$)$_2$. For a compound or salt of Formula (I), when at least one of $R^2$ and $R^3$ is hydrogen and the other of $R^2$ and $R^3$ with $R^1$ is taken together with the atoms to which they are attached to form a heterocycle substituted with one or more $R^6$, $R^6$ may be independently selected at each occurrence from halogen and —OR$^5$. For a compound or salt of Formula (I), when at least one of $R^2$ and $R^3$ is hydrogen and the other of $R^2$ and $R^3$ with $R^1$ is taken together with the atoms to which they are attached to form a heterocycle substituted with one or more $R^6$, $R^6$ may be —OR$^5$ at each occurrence. In embodiments, when $R^6$ is —OR$^5$, then $R^5$ is independently selected at each occurrence from hydrogen; and $C_{1-6}$ alkyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. In embodiments, when $R^6$ is —OR$^5$, then $R^5$ is independently selected at each occurrence from hydrogen; and $C_{1-6}$ alkyl which is optionally substituted at each occurrence by halogen, —CN, —NO$_2$, —OH, —NH$_2$, —COOH, and —OCH$_3$. In embodiments, when $R^6$ is —OR$^5$, then $R^5$ is independently selected at each occurrence from hydrogen; and $C_{1-6}$ alkyl which is substituted at each occurrence by halogen, —CN, —NO$_2$, —OH, —NH$_2$, —COOH, and —OCH$_3$. In embodiments, when $R^6$ is —OR$^5$, then $R^5$ is independently selected at each occurrence from hydrogen and $C_{1-6}$ alkyl. In embodiments, when $R^6$ is —OR$^5$, then $R^5$ is hydrogen at each occurrence.

For a compound or salt of Formula (II), $R^4$ may be selected from —OR$^5$, —C(O)OR$^5$, and —OP(=O)(OR$^5$)$_2$. For a compound or salt of Formula (II), $R^4$ may be OR$^5$. For a compound or salt for Formula (II), when $R^4$ is OR$^5$, $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt for Formula (II), when $R^4$ is OR$^5$, $R^5$ is independently selected at each occurrence from hydrogen; and $C_{1-6}$ alkyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt for Formula (II), when $R^4$ is OR$^5$, $R^5$ is independently selected at each occurrence from hydrogen; and $C_{1-6}$ alkyl is optionally substituted at each occurrence by halogen, —CN, —NO$_2$, —OH, —NH$_2$, —COOH, and —OCH$_3$. For a compound or salt for Formula (II), when $R^4$ is OR$^5$, $R^5$ is independently selected at each occurrence from hydrogen; and $C_{1-6}$ alkyl is substituted at each occurrence by halogen, —CN, —NO$_2$, —OH, —NH$_2$, —COOH, and —OCH$_3$. For a compound or salt for Formula (II), when $R^4$ is OR$^5$, $R^5$ is independently selected at each occurrence from hydrogen; and $C_{1-6}$ alkyl. For a compound or salt for Formula (II), when $R^4$ is OR$^5$, $R^5$ is hydrogen at each occurrence.

For a compound or salt of Formula (II), $R^4$ may be —C(O)OR$^5$. For a compound or salt of Formula (II), when $R^4$ is —C(O)OR$^5$, $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt of Formula (II), when $R^4$ is —C(O)OR$^5$, $R^5$ is independently selected at each occurrence from hydrogen; and $C_{1-6}$ alkyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt of Formula (II), when R$^4$ is —C(O)OR$^5$, R$^5$ is independently selected at each occurrence from hydrogen; and C$_{1-6}$ alkyl is optionally substituted at each occurrence by halogen, —CN, —NO$_2$, —OH, —NH$_2$, —COOH, and —OCH$_3$. For a compound or salt of Formula (II), when R$^4$ is —C(O)OR$^5$, R$^5$ is independently selected at each occurrence from hydrogen; and C$_{1-6}$ alkyl is substituted at each occurrence by halogen, —CN, —NO$_2$, —OH, —NH$_2$, —COOH, and —OCH$_3$. For a compound or salt of Formula (II), when R$^4$ is —C(O)OR$^5$, R$^5$ is independently selected at each occurrence from hydrogen; and C$_{1-6}$ alkyl. For a compound or salt of Formula (II), when R$^4$ is —C(O)OR$^5$, R$^5$ is hydrogen.

For a compound or salt of Formula (II), R$^4$ may be —OP(=O)(OR$^5$)$_2$. For a compound or salt of Formula (II), when R$^4$ is —OP(=O)(OR$^5$)$_2$, R$^5$ is independently selected at each occurrence from hydrogen; and C$_{1-6}$ alkyl, C$_{2-6}$ alkenyl, C$_{2-6}$ alkynyl, C$_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt of Formula (II), when R$^4$ is —OP(=O)(OR$^5$)$_2$, R$^5$ is independently selected at each occurrence from hydrogen; and C$_{1-6}$ alkyl, C$_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$. For a compound or salt of Formula (II), when R$^4$ is —OP(=O)(OR$^5$)$_2$, R$^5$ is independently selected at each occurrence from hydrogen; and C$_{1-6}$ alkyl is optionally substituted at each occurrence by halogen, —CN, —NO$_2$, —OH, —NH$_2$, —COOH, and —OCH$_3$. For a compound or salt of Formula (II), when R$^4$ is —OP(=O)(OR$^5$)$_2$, R$^5$ is independently selected at each occurrence from hydrogen; and C$_{1-6}$ alkyl is substituted at each occurrence by halogen, —CN, —NO$_2$, —OH, —NH$_2$, —COOH, and —OCH$_3$. For a compound or salt of Formula (II), when R$^4$ is —OP(=O)(OR$^5$)$_2$, R$^5$ is independently selected at each occurrence from hydrogen; and C$_{1-6}$ alkyl. For a compound or salt of Formula (II), when R$^4$ is —OP(=O)(OR$^5$)$_2$, R$^5$ is hydrogen.

In embodiments, n is 0. In embodiments, n is 1. In embodiments, n is 2. In embodiments, n is 3. In embodiments, n is 4. In embodiments, n is 5.

In embodiments, m is 0. In embodiments, m is 1. In embodiments, m is 2. In embodiments, m is 3. In embodiments, m is 4. In embodiments, m is 5.

In embodiments, a compound of the disclosure is represented by Formula (I) or Formula (II):

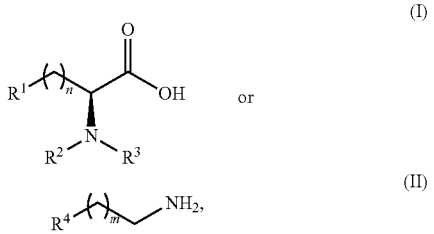

or a salt of any one thereof, wherein: R$^1$ is selected from —SR$^5$, —C(O)OR$^5$, and —OP(=O)(OR$^5$)$_2$; R$^2$ and R$^3$ is hydrogen or, at least one of R$^2$ and R$^3$ is hydrogen and the other of R$^2$ and R$^3$ with R$^1$ taken together with the atoms to which they are attached to form a heterocycle substituted with one or more R$^6$; R$^4$ is selected from —OR$^5$, —C(O)OR$^5$, and —OP(=O)(OR$^5$)$_2$; R$^5$ is independently selected at each occurrence from hydrogen; and C$_{1-6}$ alkyl, which is independently optionally substituted at each occurrence by halogen, —CN, —NO$_2$, —OH, —NH$_2$, —COOH, and —OCH$_3$; R$^6$ is independently selected at each occurrence from halogen, —NO$_2$, —CN, —OR$^5$, C$_{1-10}$ alkyl, C$_{2-10}$ alkenyl, and C$_{2-10}$ alkynyl, each of which is independently optionally substituted at each occurrence with one or more substituents selected from halogen, —CN, —NO$_2$, —OH, —NH$_2$, —COOH, and —OCH$_3$; and n and m are independently selected from 0, 1, 2, 3, 4, or 5.

In embodiments, a compound of the disclosure is represented by Formula (I) or Formula (II):

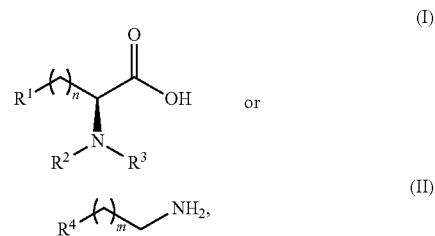

or a salt of any one thereof, wherein: R$^1$ is selected from —SR$^5$, —C(O)OR$^5$, and —OP(=O)(OR$^5$)$_2$; R$^2$ and R$^3$ is hydrogen or, at least one of R$^2$ and R$^3$ is hydrogen and the other of R$^2$ and R$^3$ with R$^1$ taken together with the atoms to which they are attached to form a heterocycle substituted with one or more R$^6$; R$^4$ is selected from —OR$^5$, —C(O)OR$^5$, and —OP(=O)(OR$^5$)$_2$; R$^5$ is independently selected at each occurrence from hydrogen; and C$_{1-6}$ alkyl, which is independently optionally substituted at each occurrence by halogen, —CN, —NO$_2$, —OH, —NH$_2$, —COOH, and —OCH$_3$; R$^6$ is independently selected at each occurrence from halogen, —NO$_2$, —CN, or —OR$^5$; and n and m are independently selected from 0, 1, 2, 3, 4, or 5.

In embodiments, the compound or salt of Formula (I) or (II) is a non-alpha amino acid. For example, in the structures of the compounds or salt of Formula (I) or (II), the amine group is displaced further from the carboxylic acid end of the amino acid molecule. In embodiments, the compound or salt of Formula (I) or (II) is a beta-amino acid which have the amino group bonded to the second carbon away. In embodiments, the compound or salt of Formula (I) or (II) is a gamma-amino acid which have the amine group bonded to the third carbon away. Examples of non-alpha amino acids include but are not limited to beta-alanine.

In embodiments, the compound or salt of Formula (I) or (II) is a D-amino acid. Examples of D-amino acids include but are not limited to D-alanine and D-glutamate. In embodiments, the compound or salt of Formula (I) or (II) is a homo-amino acid. For example, in a homo amino acid, a methylene group is added to the alpha-carbon of the amino acid. In embodiments, the compound or salt of Formula (I) or (II) are beta-homo-amino acids. For example, beta-homo-amino acids are analogs of standard amino acids in which the carbon skeleton has been lengthened by the insertion of one carbon atom immediately after the acid group. In embodiments, the compounds described herein are N-methyl amino acids. For example, N-methyl amino acids carry a methyl group at the nitrogen instead of a proton.

Pharmaceutical Compositions

The disclosure relates to pharmaceutical compositions comprising a compound or salt of Formula (I) or (II) for the treatment of fungal and bacterial infections comprising one or a plurality of microorganisms in the form of a biofilm. In embodiments, the pharmaceutical compositions comprise (i) one or more of a compound of formula (I) or a salt thereof; (ii) one or more of a compound of formula (II) or a salt thereof; or (iii) two or more of a compound of formula (I) or a salt thereof and a compound of formula (II) or a salt thereof.

In embodiments, the pharmaceutical compositions are free of the non-bonded amino acids: alanine, arginine, asparagine, citrulline, glycine, isoleucine, leucine, methionine, lysine, 3-methylhistadine, phenylalanine, ornithine, proline, serine, and taurine, threonine, tryptophan, and/or valine. In embodiments, the pharmaceutical compositions are free of the non-bonded L-amino acids: alanine, arginine, asparagine, citrulline, glycine, isoleucine, leucine, methionine, lysine, 3-methylhistadine, phenylalanine, ornithine, proline, serine, and taurine, threonine, tryptophan, and/or valine. In embodiments, the pharmaceutical compositions are free of the non-bonded D-amino acids: alanine, arginine, asparagine, citrulline, glycine, isoleucine, leucine, methionine, lysine, 3-methylhistadine, phenylalanine, ornithine, proline, serine, and taurine, threonine, tryptophan, and/or valine. In embodiments, the pharmaceutical compositions are free of the non-bonded D-amino acids or non-bonded L-amino acids: alanine, arginine, asparagine, citrulline, glycine, isoleucine, leucine, methionine, lysine, 3-methylhistadine, phenylalanine, ornithine, proline, serine, and taurine, threonine, tryptophan, and/or valine.

In embodiments, the disclosure provides a composition comprising a compound or salt of Formula (I) or (II). In embodiments, the pharmaceutical compositions comprise (i) one or more of a compound of formula (I) or a salt thereof; (ii) one or more of a compound of formula (II) or a salt thereof; or (iii) two or more of a compound of formula (I) or a salt thereof and a compound of formula (II) or a salt thereof.

In embodiments, the present disclosure provides a composition comprising an amino acid or a salt thereof, wherein the composition is essentially free of alanine, arginine, asparagine, citrulline, glycine, isoleucine, leucine, lysine, methionine, 3-methylhistidine, phenylalanine, ornithine, proline, serine, taurine, threonine, tryptophan, valine or pharmaceutically acceptable salts thereof. In embodiments, the composition further comprises a pharmaceutically acceptable carrier. In embodiments, the pharmaceutically acceptable carrier is saline. In embodiments, the composition further comprises glycerin. In embodiments, the glycerin is at a weight to volume percentage of from about 0.1% to about 5%.

In embodiments, the present disclosure provides a composition comprising at least two of cysteine, glutamic acid, aspartic acid, beta-alanine, 2-aminoadipic acid, cystathionine, ethanolamine, homocysteine, hydroxyproline, phosphoethanolamine, phosphoserine, or salts thereof, wherein each cysteine, glutamic acid, aspartic acid, beta-alanine, 2-aminoadipic acid, cystathionine, ethanolamine, homocysteine, hydroxyproline, phosphoethanolamine, phosphoserine, or salts thereof is at a weight to volume percent from about 0.1% to about 5% and the composition is in the form of an intravenous formulation, a solution or a douche. In embodiments, the composition comprises at least two selected from the group consisting of cysteine, glutamic acid, aspartic acid, beta-alanine, 2-aminoadipic acid, cystathionine, ethanolamine, homocysteine, hydroxyproline, phosphoethanolamine, phosphoserine, and salts thereof; wherein each of the cysteine, glutamic acid, aspartic acid, beta-alanine, 2-aminoadipic acid, cystathionine, ethanolamine, homocysteine, hydroxyproline, phosphoethanolamine, phosphoserine, and salts thereof is at a weight to volume percent from about 0.1% to about 5% and the composition is in the form of an intravenous formulation, a solution or a douche.

In embodiments, the composition further comprises glycerin. In embodiments, the composition comprises cysteine or a salt thereof, glutamic acid or a salt thereof, and aspartic acid or a salt thereof. In embodiments, each of cysteine or a salt thereof, glutamic acid or a salt thereof, and aspartic acid or a salt thereof are at a weight to volume percent of about 0.4%. In embodiments, each of cysteine or a salt thereof, glutamic acid or a salt thereof, and aspartic acid or a salt thereof are at a weight to volume percent of about 0.5%. In embodiments, each of cysteine or a salt thereof, glutamic acid or a salt thereof, and aspartic acid or a salt thereof are at a weight to volume percent of about 0.6%.

The present disclosure provides a pharmaceutical composition comprising a compound or salt of Formula (I) or (II) in a therapeutically effective amount. In embodiments, the pharmaceutical compositions comprise (i) one or more of a compound of formula (I) or a salt thereof; (ii) one or more of a compound of formula (II) or a salt thereof; or (iii) two or more of a compound of formula (I) or a salt thereof and a compound of formula (II) or a salt thereof. In embodiments, the compound or salt of Formula (I) or (II) may be in a liquid dosage form but dissolved at a concentration of from about 0.1% to about 10% weight per volume. In embodiments, the compound or salt of Formula (I) or (II) may be in a liquid dosage form but dissolved at a concentration of from about 0.1% to about 10% weight per volume, wherein the composition is free of a non-bonded amino acids from Tables 2 and 3 at a concentration of about 0.01%, 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, 1.0% or more. In embodiments, the dissolved concentration is about 0.5% weight per volume of solution. In embodiments, the dosage form is free of any one or plurality of non-bonded amino acids disclosed in Tables 2 and 3. In embodiments, the dosage form is free of any one or plurality of non-bonded amino acids identified as an amino acid having a neutral effect in forming or disrupting a bacterial and/or fungal biofilm in Tables 2 and 3. In embodiments, the dosage form is free of any one or plurality of non-bonded amino acids identified as an amino acid encouraging the formation of a biofilm in Tables 2 and 3. In embodiments, the dosage form is free of any one or plurality of non-bonded amino acids identified in Tables 2 and 3 as an amino acid that positively contributes to the inhibition of bacterial and/or fungal biofilm formation or maintenance. For example, pharmaceutical compositions comprising a compound or salt of Formula (I) or (II) may comprise from about 0.1% to about 5.0% weight to volume of any one non-bonded amino acid in columns 1 or 2 from Tables 2 and 3 but also be free of any other non-bonded amino acid in columns 1 or 2 from Tables 2 and 3. In embodiments, any of the compositions disclosed herein may comprise any one or plurality of amino acids or slats thereof identified as Neutral in Tables 4 and 5.

The disclosure relates to pharmaceutical compositions comprising a first non-bonded amino acid explicitly not comprising or being free of a second, third, fourth or more non-bonded amino acid, where addition of second, third, fourth or more non-bonded amino acid may have a deleterious effect on inhibition of biofilm formation or maintenance. In embodiments, to be "free of" the non-bonded amino acid in the composition may refer to free of an amount sufficient to cause a deleterious effect on the inhibition of biofilm formation or maintenance, such that addition of that amount encourages formation of or stability of a bacterial or fungal biofilm, or, in the case of "neutral effect" does not have an effect on either destroying or encouraging formation of the bacterial or fungal biofilms. In embodiments, to be "free of" a particular amino acid means that the composition or pharmaceutical composition disclosed herein is free of a percentage weight to volume of one or a plurality of non-bonded amino acids or salts thereof equal to no greater than about 0.01%, 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, or about 1.0%. It is understood that the term "free of" in embodiments is meant to mean that the non-bonded amino acid is absent in the composition, in trace amounts or at a concentration that would not affect the biological effect of an effective amount of one or more amino acids that have a disruptive or inhibitory effect on the bacterial and/or fungal biofilm formation or maintenance. In embodiments, to be "free of" a particular amino acid means that the composition or pharmaceutical composition disclosed herein is free of a particular percentage weight to volume of one or a plurality of non-bonded amino acids or salts thereof identified in Tables 4 and 5. For instance if the composition of pharmaceutical composition comprises a first non-bonded amino acid and is "free of" the second or more non-bonded amino acids, the embodiments include the composition or pharmaceutical composition disclosed herein wherein the second or more non-bonded amino acid is not present at an independently discrete concentration or range, such as about 0.01%, 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, or about 1.0% for the second a non-bonded amino acid and any other discrete concentration or percentage in respect to any third, fourth, fifth or more amino acid. In embodiments, the composition or pharmaceutical composition is free of one or a plurality of non-bonded amino acids at a concentration of X nM, wherein X is any positive integer from about 1 to about 10,000. Any range of from about 1 to about any positive integer to about 10,000 is contemplated by the embodiment.

In embodiments, the pharmaceutical composition comprises a compound or salt of Formula (I) or (II) from about 0.1% to about 0.39% in weight to volume of solution. In embodiments, the pharmaceutical composition comprises a compound or salt of Formula (I) or (II) from about 0.41% to about 5.0% in weight to volume of solution. In embodiments, the pharmaceutical composition comprises a compound or salt of Formula (I) or (II) from about 0.1% to about 0.39% in weight to volume of solution and another compound or salt of Formula (I) or (II) from about 0.41% to about 5.0% in weight to volume of solution. In embodiments, the pharmaceutical composition comprises a compound or salt of Formula (I) or (II) from about 0.49% to about 0.51% in weight to volume of solution.

In embodiments, the composition comprises non-bonded beta-alanine, or a pharmaceutically acceptable salt thereof, at a weight to volume percent from about 0.1% to about 5.0%; non-bonded 2-aminoadipic acid, or a pharmaceutically acceptable salt thereof, at a weight to volume percent from about 0.1% to about 5.0%; non-bonded aspartic acid, or a pharmaceutically acceptable salt thereof, at a weight to volume percent from about 0.1% to about 5.0%; non-bonded cystathionine (0.2%), or a pharmaceutically acceptable salt thereof, at a weight to volume percent from about 0.1% to about 5.0%; non-bonded cysteine, or a pharmaceutically acceptable salt thereof, at a weight to volume percent from about 0.1% to about 5.0%; non-bonded ethanolamine, or a pharmaceutically acceptable salt thereof, at a weight to volume percent from about 0.1% to about 5.0%; non-bonded glutamic acid, or a pharmaceutically acceptable salt thereof, at a weight to volume percent from about 0.1% to about 5.0%, non-bonded homocysteine, or a pharmaceutically acceptable salt thereof, at a weight to volume percent from about 0.1% to about 5.0%; non-bonded hydroxyproline, or a pharmaceutically acceptable salt thereof, at a weight to volume percent from about 0.1% to about 5.0%; non-bonded phosphoethanolamine, or a pharmaceutically acceptable salt thereof, at a weight to volume percent from about 0.1% to about 5.0%; non-bonded phosphoserine, or a pharmaceutically acceptable salt thereof, at a weight to volume percent from about 0.1% to about 5.0%.

In embodiments, the pharmaceutical compositions or formulations of the disclosure comprise one or a plurality of compounds of the disclosure. In embodiments, the pharmaceutical compositions or formulations of the disclosure are free of one or a plurality of non-bonded alanine, non-bonded arginine, non-bonded asparagine, non-bonded valine, non-bonded citrulline, non-bonded glycine, non-bonded isoleucine, non-bonded leucine, non-bonded lysine, non-bonded methionine, non-bonded 3-methylhistidine, non-bonded phenylalanine, non-bonded ornithine, non-bonded proline, non-bonded serine, non-bonded taurine, non-bonded threonine, non-bonded tryptophan, non-bonded valine.

The pharmaceutical composition comprising a compound or salt of Formula (I) or (II) may be formulated for the therapeutic or prophylactic treatment of diseases, such as bacterial infections or fungal infections or for treatment of bacterial cells and/or fungal cells that are in a biofilm state. In embodiments, the pharmaceutical composition comprising a compound or salt of Formula (I) or (II) is formulated for administration intravenously, topically, irrigation of wounds either as wound dressing or in sterile solution, intradermally, intramucosally, subcutaneously, sublingually, orally, intravaginally, intramuscularly, intracavemously, intraocularly, intranasally, into a sinus, intrarectally, gastro-intestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, swish and swallow treatment of oral candidiasis, transmucosal, or transdermal delivery.

In embodiments, the pharmaceutical composition comprising a compound or salt of Formula (I) or (II) is prepared in accordance with standard procedures and are administered at dosages that are selected to reduce, prevent or eliminate biofilm formation or maintenance (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

In embodiments, the pharmaceutical composition comprises a compound or salt of Formula (I) or (II) with one or more nontoxic, pharmaceutically-acceptable carriers and/or diluents and/or adjuvants and/or excipients. Non-limiting examples of carriers and/or diluents and/or adjuvants and/or excipients include corn starch or gelatin, lactose, sucrose, microcrystalline cellulose, kaolin, mannitol, dicalcium phosphate, sodium chloride, alginic acid croscarmellose sodium, microcrystalline cellulose, corn starch, sodium starch glycolate and alginic acid.

In embodiments, the disclosure provides a composition in the form of an intravenous formulation. In embodiments, the disclosure provides a composition in the form of a solution. In embodiments, the disclosure provides a composition in the form of a douche.

Dosage forms may comprise tablet binders, lubricants and or flavoring agents. Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that may be used include magnesium stearate or other metallic stearates, stearic acid, silicone fluid, talc, waxes, oils and colloidal silica. Flavoring agents such as peppermint, oil of wintergreen, cherry flavoring or the like may also be used. It may also be desirable to add a coloring agent to make the dosage form more aesthetic in appearance or to help identify the product.

For oral or parenteral administration, the composition comprising a compound or salt of Formula (I) or (II) may be mixed with pharmaceutical carriers and excipients and used in the form of tablets, capsules, elixirs, suspensions, syrups, wafers and the like. The composition comprising a compound or salt of Formula (I) or (II) may contain from about 0.1% to about 99% by weight of the active compound, such as from about 10% to about 30%. In embodiments, the compositions are free of cysteine or a salt thereof at 0.4% weight to volume in a liquid solution. In embodiments, the compositions are free of aspartic acid at 0.4% weight or a salt thereof to volume in a liquid solution. In embodiments, the compositions are free of glutamic acid or a salt at 0.4% weight to volume in a liquid solution. In embodiments, the compositions are free of an amino acid or salts thereof at a concentration of about 0.4 grams per ounce of solution.

For oral use, solid formulations such as tablets and capsules may be useful. Sustained release or enterically coated preparations may also be devised. For pediatric and geriatric applications, one embodiment provides suspensions, syrups and chewable tablets. For oral administration, the pharmaceutical compositions comprising a compound or salt of Formula (I) or (II) may be in the form of, for example, a tablet, capsule, suspension or liquid.

The pharmaceutical compositions comprising compound or salt of Formula (I) or (II) may be made in the form of a dosage unit containing a therapeutically effective amount of the compound or salt of Formula (I) or (II). Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations may contain conventional additives such as suspending agents, emulsifying agents, non-aqueous agents, preservatives, coloring agents and flavoring agents. Non-limiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition comprising a compound or salt of Formula (I) or (II) may be dissolved or suspended in any of the commonly used intravenous fluids and administered by infusion. Intravenous fluids include, but are not limited, physiological saline or Ringer's solution. Intravenous administration may be accomplished by using, without limitation, syringe, minipump or intravenous line.

Pharmaceutical compositions comprising compound or salt of Formula (I) or (II) for parenteral injection may further comprise pharmaceutically-acceptable aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity may be maintained, for example, by the use of coating materials such as lecithin, by the maintenance of the required particle size in the case of dispersions, and by the use of surfactants. The compositions may include various buffers.

In embodiments, the composition comprising a compound or salt of Formula (I) or (II) also contain adjuvants such as preservatives, wetting agents, emulsifying agents, and dispersing agents. These compositions may also contain taggants or other anti-counterfeiting agents. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms may be made by forming microencapsulating matrices of a compound or salt of Formula (I) or (II) in biodegradable polymers such as polylactide-polyglycolide. Depending upon the ratio of the compound or salt of Formula (I) or (II) to polymer and the nature of the particular polymer employed, the rate of release may be controlled. Examples of other biodegradable polymers include poly(orthoesters) and poly(anhydrides). Depot injectable formulations may also be prepared by entrapping the compound or salt of Formula (I) or (II) in liposomes or microemulsions, which may be compatible with body tissues.

The injectable formulations may be sterilized, for example, by filtration through a bacterial-retaining filter, or by incorporating sterilizing agents in the form of sterile solid compositions, which can be dissolved or dispersed in sterile water or other sterile injectable medium just prior to use or storage.

Solid dosage forms for oral administration may include capsules, tablets, pills, powders, and granules. Such forms may include forms that dissolve or disintegrate quickly in the oral environment. In such solid dosage forms, the compound or salt of Formula (I) or (II) may be mixed with at least one inert, pharmaceutically-acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropyl methyl cellulose, hydroxypropyl cellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof; and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, may be prepared with coatings and shells such as functional and aesthetic enteric coatings and other coatings. They may optionally contain opacifying agents and colorants. They may also be in a form capable of controlled or sustained release. Examples of embedding compositions that may be used for such purposes include polymeric substances and waxes.

The pharmaceutical composition comprising a compound or salt of Formula (I) or (II) may be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. Nos. 4,452,775, 5,039,660, and 3,854,480, the disclosure of which are incorporated here by reference in their entireties.

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug may the depend upon its rate of dissolution, which in turn, may depend upon crystal size and crystalline form. Alternatively, delayed absorption of a parenterally administered drug form may be accomplished by dissolving or suspending the drug in an oil vehicle.

For intramuscular preparations, a sterile formulation of a compound or salt of Formula (I) or (II) may be dissolved and administered in a pharmaceutical diluent such as Water-for-Injection (WFI), physiological saline or about 5% glucose or about 3% glycerol. A suitable insoluble form of the compound or salt of Formula (I) or (II) may be prepared and administered as a suspension in an aqueous base or a pharmaceutically acceptable oil base, e.g., an ester of a long chain fatty acid such as ethyl oleate.

A dose of an intravenous, intramuscular, or parental formulation of a compound or salt of Formula (I) or (II) or a pharmaceutical composition comprising a compound or salt of Formula (I) or (II) may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use, a compound or salt of Formula (I) or (II) or a pharmaceutical composition comprising a compound or salt of Formula (I) or (II) may be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compound, salt or pharmaceutical composition may be presented in liquid or semi-liquid form formulated in hydrophobic or hydrophilic bases as ointments, creams, lotions, paints or powders. For rectal and vaginal administration, the compound salt or pharmaceutical composition may be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the compound, salt or pharmaceutical composition may be in powder form for reconstitution in the appropriate pharmaceutically acceptable carrier at the time of delivery. In another embodiment, the unit dosage form of a compound or salt of Formula (I) or (II) may be a solution o in a suitable diluent, in sterile hermetically sealed ampoules or sterile syringes. The concentration of the compound or salt of Formula (I) or (II) in the unit dosage may vary, e.g. from about 1 percent to about 50 percent, depending on the compound or salt used and its solubility and the dose desired by the physician. If the composition comprising a compound or salt of Formula (I) or (II) contains dosage units, each dosage unit can contain from about 1 to about 500 mg of the active material. For adult human treatment, the dosage employed can range from about 5 mg to about 10 g, per day, depending on the route and frequency of administration.

The pharmaceutical compositions comprising a compound or salt of Formula (I) or (II) may be placed in a pharmaceutically acceptable carrier and are delivered to a recipient subject (e.g., a human) in accordance with known methods of drug delivery.

Exemplary procedures for delivering an active ingredient are described in U.S. Pat. Nos. 6,468,967; 6,852,689; and 5,041,567, and in PCT patent application number EP94/02552 (publication no. WO 95/05384), the disclosures of which are incorporated by reference in their entireties. In one embodiment, a compound or salt of Formula (I) or (II) or a pharmaceutical composition comprising a compound or salt of Formula (I) or (II) is administered orally, rectally or via injection e.g. intravenous, intramuscular or subcutaneous. In another embodiment, a compound or salt of Formula (I) or (II) or a pharmaceutical composition comprising a compound or salt of Formula (I) or (II) is administered orally, rectally or via injection e.g. intravenous, intramuscular or subcutaneous to treat an infection caused by β-lactamase producing bacteria.

Suitable pharmaceutically acceptable carriers may be magnesium carbonate, magnesium stearate, talc, lactose, sugar, pectin, dextrin, starch, tragacanth, methyl cellulose, sodium carboxymethyl cellulose, a low-melting wax, cocoa butter, and the like. Salts include, but are not limited to, pharmaceutically acceptable salts. Examples of pharmaceutically acceptable salts include: acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and benzathine. In embodiments, pharmaceutical compositions comprise pharmaceutically acceptable salts such as hydrochlorides, sulfates and bitartrates. The hydrochloride and sulfate salts are particularly preferred.

A lubricant can be used in a tablet formulation to prevent the tablet and punches from sticking in the die. The lubricants include, but are not limited to, such slippery solids as talc, magnesium and calcium stearate, stearic acid and hydrogenated vegetable oils.

Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation.

Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use. Preparations may also contain mucosal enhancers.

In embodiments, the oral transmucosal solid dosage further comprises a permeation enhancer. In embodiments, the permeation enhancer is chosen from: a bile salt, sodium dodecyl sulfate, dimethyl sulfoxide, sodium lauryl sulfate, a derivative of a saturated or an unsaturated fatty acid, a surfactant, a bile salt analog, and a derivative of a bile salt. In embodiments the oral transmucosal dosage form is chosen from: a chewing gum, a patch, a lozenge, a lozenge-on-a-handle, a tablet, a troche, a pastille, a sachet, a sublingual tablet, and a rapid disintegrating tablet. In embodiments, the oral transmucosal solid dosage form of wherein the composition further comprises at least one flavoring agent, artificial coloring, sweetener, lubricating agent, disintegration agent, lubricating agent, diluent, base, or buffering agent. In embodiments, the oral transmucosal solid dosage form further comprises a sustained release agent. The disclosure is directed to an oral transmucosal solid dosage form comprising from wherein the concentration of analog is from about 0.01% to about 90% of the dry matter weight of the composition.

Solid dosage forms such as lozenges and tablets may also be used for oral delivery of pharmaceuticals. For example, nitroglycerin sublingual tablets are designed to deliver small amounts of the potent nitroglycerin, which is almost immediately dissolved and absorbed. On the other hand, most lozenges or tablets are typically designed to dissolve in the mouth over a period of at least several minutes which allows extended dissolution of the lozenge and absorption of the drug. Administration of lozenges or sublingual tablets generally utilize an "open" delivery system, in which the drug delivery conditions are influenced by the conditions of the surrounding environment, such as rate of saliva secretion, pH of the saliva, or other conditions beyond the control of the formulation. A lozenge-on-a-handle (similar to a lollipop) is another dosage form suitable for transmucosal drug delivery. In addition to being non-invasive and providing a particularly easy method of delivery, the lozenge-on-a-handle (or lozenge with an integrated oral transmucosal applicator) dosage form allows a patient or caregiver to move the dosage form in and out of the mouth to titrate the dose. This practice is called dose-to-effect, in which a patient or caregiver controls the administration of the dose until the expected therapeutic effect is achieved. This is particularly important for certain signs and/or symptoms, such as pain, nausea, motion sickness, and premedication prior to anesthesia because each patient needs a different amount of medication to treat these signs and/or symptoms. For these types of treatments, the patient is the only one who knows how much medication is enough. Once the appropriate amount of drug is delivered, the patient or caregiver can remove the lozenge-on-a-handle, thus, stopping delivery of the drug. This feature is especially important for particularly potent drugs, which may present a significant advantage of terminating drug administration once the desired effect is achieved.

When the solid dosage form dissolves in the oral cavity, some of the saliva containing the pharmaceutical agent may be swallowed, and a portion of the drug may ultimately be absorbed from the intestines.

The compositions described herein may be administered in a sustained release composition, such as those described in, for example, U.S. Pat. Nos. 5,672,659 and 5,595,760, and herein incorporated by reference in their entireties. The use of immediate or sustained release compositions depends on the type of condition being treated.

The pharmaceutical composition comprising a compound or salt of Formula (I) or (II) may be in a dosage amount in an effective amount to induce death or disruption of biofilms of bacterial or fungal cells. The pharmaceutical composition comprising a compound or salt of Formula (I) or (II) may be in an effective amount to reduce the growth rate or inhibiting the formation of a biofilm of a bacterial or fungal species. The pharmaceutical composition comprising a compound or salt of Formula (I) or (II) may be in a dosage amount for an effective amount to reduce or eliminate the signs and/or symptoms of a bacterial or fungal infection in a subject.

The dose of the pharmaceutical composition comprising a compound or salt of Formula (I) or (II) may vary. The dose of the composition may be once per day. In embodiments, multiple doses may be administered to the subject daily. In embodiments, the total dosage is administered in at least two application periods. In embodiments, the period can be an hour, a day, a month, a year, a week, or a two-week period. In embodiments, the total dosage is administered in two or more separate application periods, or separate doses. In embodiments, the methods of administering the pharmaceutical composition comprising a compound or salt of Formula (I) or (II) comprises administration periods of once an hour, once every two hours, once every 6 hours, once every 12 hours or once a day. In embodiments, the methods of administering the pharmaceutical composition comprising a compound or salt of Formula (I) or (II) comprise administration periods of twice an hour or more frequently depending upon the severity of the infection of contamination or to prevent toxic side-effects from destruction of the pathogen.

In embodiments, subjects can be administered the composition in which the composition is provided in a daily dose range of about 0.0001 mg/kg to about 5000 mg/kg of the weight of the subject. The dose administered to the subject can also be measured in terms of total amount of amino acid administered per day. In embodiments, a subject is administered from about 0.001 to about 3000 milligrams of a compound or salt of Formula (I) or (II) per day. In embodiments, a subject is administered up to about 2000 milligrams of a compound or salt of Formula (I) or (II) per day. In embodiments, a subject is administered up to about 1800 milligrams of a compound or salt of Formula (I) or (II) per day. In embodiments, a subject is administered up to about 1600 milligrams of a compound or salt of Formula (I) or (II) per day. In embodiments, a subject is administered up to about 1400 milligrams of a compound or salt of Formula (I) or (II) per day. In embodiments, a subject is administered up to about 1200 milligrams of a compound or salt of Formula (I) or (II) per day. In embodiments, a subject is administered up to about 1000 milligrams of a compound or salt of Formula (I) or (II) per day. In embodiments, a subject is administered up to about 800 milligrams of a compound or salt of Formula (I) or (II) per day. In embodiments, a subject is administered from about 0.001 milligrams to about 700 milligrams of a compound or salt of Formula (I) or (II) per dose. In embodiments, a subject is administered up to about 700 milligrams of a compound or salt of Formula (I) or (II) per dose. In embodiments, a subject is administered up to about 600 milligrams of a compound or salt of Formula (I) or (II) per dose. In embodiments, a subject is administered up to about 500 milligrams of a compound or salt of Formula (I) or (II) per dose. In embodiments, a subject is administered up to about 400 milligrams of a compound or salt of Formula (I) or (II) per dose. In embodiments, a subject is administered up to about 300 milligrams of a compound or salt of Formula (I) or (II) per dose. In embodiments, a subject is administered up to about 200 milligrams of a compound or salt of Formula (I) or (II) per dose. In embodiments, a subject is administered up to about 100 milligrams of a compound or salt of Formula (I) or (II) per dose. In embodiments, a subject is administered up to about 50 milligrams of a compound or salt of Formula (I) or (II) per dose.

In embodiments, subjects can be administered the composition comprising a compound or salt of Formula (I) or (II) which is administered in a daily dose range of about 0.0001 mg/kg to about 5000 mg/kg of the weight of the subject. In embodiments, the composition comprising a compound or salt of Formula (I) or (II) is administered in a daily dosage of up about 450 mg/kg of the weight of the subject. In embodiments, the composition comprising a compound or salt of Formula (I) or (II) is administered in a daily dosage of up about 400 mg/kg of the weight of the subject. In embodiments, the composition comprising a compound or salt of Formula (I) or (II) is administered in a daily dosage of up about 350 mg/kg of the weight of the subject. In embodiments, the composition comprising a compound or salt of Formula (I) or (II) is administered in a daily dosage of up about 300 mg/kg of the weight of the subject. In embodiments, the composition comprising a compound or salt of Formula (I) or (II) is administered in a daily dosage of up about 250 mg/kg of the weight of the subject. In embodiments, the composition comprising a compound or salt of Formula (I) or (II) is administered in a daily dosage of up about 200 mg/kg of the weight of the subject. In embodiments, the composition comprising a compound or salt of Formula (I) or (II) is administered in a daily dosage of up about 150 mg/kg of the weight of the subject. In embodiments, the composition comprising a compound or salt of Formula (I) or (II) is administered in a daily dosage of up about 100 mg/kg of the weight of the subject. In embodiments, the composition comprising a compound or salt of Formula (I) or (II) is administered in a daily dosage of up about 50 mg/kg of the weight of the subject. In embodiments, the composition comprising a compound or salt of Formula (I) or (II) is administered in a daily dosage of up about 25 mg/kg of the weight of the subject.

In embodiments, the composition comprising a compound or salt of Formula (I) or (II) is administered in a daily dosage of up about 10 mg/kg of the weight of the subject. In embodiments, the composition comprising a compound or salt of Formula (I) or (II) is administered in a daily dosage of up about 5 mg/kg of the weight of the subject. In embodiments, the composition comprising a compound or salt of Formula (I) or (II) is administered in a daily dosage of up about 1 mg/kg of the weight of the subject. In embodiments, the composition comprising is administered in a daily dosage of up about 0.1 mg/kg of the weight of the subject. In embodiments, the composition comprising a compound or salt of Formula (I) or (II) is administered in a daily dosage of up about 0.01 mg/kg of the weight of the subject. In embodiments, the composition comprising a compound or salt of Formula (I) or (II) is administered in a daily dosage of up about 0.001 mg/kg of the weight of the subject. The dose administered to the subject can also be measured in terms of total amount of amino acid or amino acid composition administered per day.

In embodiments, a subject in need thereof is administered from about 1 ng to about 500 µg of a compound or salt of Formula (I) or (II) per day. In embodiments, a subject in need thereof is administered from about 1 ng to about 10 ng of a compound or salt of Formula (I) or (II) per day. In embodiments, a subject in need thereof is administered from about 10 ng to about 20 ng of a compound or salt of Formula (I) or (II) per day. In embodiments, a subject in need thereof is administered from about 10 ng to about 100 ng of a compound or salt of Formula (I) or (II) per day. In embodiments, a subject in need thereof is administered from about 100 ng to about 200 ng of a compound or salt of Formula (I) or (II) per day. In embodiments, a subject in need thereof is administered from about 200 ng to about 300 ng of a compound or salt of Formula (I) or (II) per day. In embodiments, a subject in need thereof is administered from about 300 ng to about 400 ng of a compound or salt of Formula (I) or (II) per day. In embodiments, a subject in need thereof is administered from about 400 ng to about 500 ng of a compound or salt of Formula (I) or (II) per day. In embodiments, a subject in need thereof is administered from about 500 ng to about 600 ng of a compound or salt of Formula (I) or (II) per day. In embodiments, a subject in need thereof is administered from about 600 ng to about 700 ng of a compound or salt of Formula (I) or (II) per day. In embodiments, a subject in need thereof is administered from about 800 ng to about 900 ng of a compound or salt of Formula (I) or (II) per day. In embodiments, a subject in need thereof is administered from about 900 ng to about 1 µg of a compound or salt of Formula (I) or (II) per day. In embodiments, a subject in need thereof is administered from about 1 µg to about 100 µg of a compound or salt of Formula (I) or (II) per day. In embodiments, a subject in need thereof is administered from about 100 μg to about 200 μg of a compound or salt of Formula (I) or (II) per day. In embodiments, a subject in need thereof is administered from about 200 μg to about 300 μg of a compound or salt of Formula (I) or (II) per day. In embodiments, a subject in need thereof is administered from about 300 μg to about 400 μg of a compound or salt of Formula (I) or (II) per day. In embodiments, a subject in need thereof is administered from about 400 μg to about 500 μg of a compound or salt of Formula (I) or (II) per day. In embodiments, a subject in need thereof is administered from about 500 μg to about 10 mg of a compound or salt of Formula (I) or (II) per day. In embodiments, a subject in need thereof is administered from about 600 μg to about 700 μg of a compound or salt of Formula (I) or (II) per day. In embodiments, a subject in need thereof is administered from about 800 μg to about 900 μg of a compound or salt of Formula (I) or (II) per day. In embodiments, a subject in need thereof is administered from about 900 μg to about 1 mg of a compound or salt of Formula (I) or (II) per day.

In embodiments, a subject in need thereof is administered from about 0.0001 to about 3000 milligrams of a compound or salt of Formula (I) or (II) per day. In embodiments, a subject is administered up to about 2000 milligrams of a compound or salt of Formula (I) or (II) per day. In embodiments, a subject is administered up to about 1800 milligrams of a compound or salt of Formula (I) or (II) per day. In embodiments, a subject is administered up to about 1600 milligrams of a compound or salt of Formula (I) or (II) per day. In embodiments, a subject is administered up to about 1400 milligrams of a compound or salt of Formula (I) or (II) per day. In embodiments, a subject is administered up to about 1200 milligrams of a compound or salt of Formula (I) or (II) per day. In embodiments, a subject is administered up to about 1000 milligrams of a compound or salt of Formula (I) or (II) per day. In embodiments, a subject is administered up to about 800 milligrams of a compound or salt of Formula (I) or (II) per day. In embodiments, a subject is administered from about 0.0001 milligrams to about 700 milligrams of a compound or salt of Formula (I) or (II) per dose. In embodiments, a subject is administered up to about 700 milligrams of a compound or salt of Formula (I) or (II) per dose. In embodiments, a subject is administered up to about 600 milligrams of a compound or salt of Formula (I) or (II) per dose. In embodiments, a subject is administered up to about 500 milligrams of a compound or salt of Formula (I) or (II) per dose. In embodiments, a subject is administered up to about 400 milligrams of a compound or salt of Formula (I) or (II) per dose. In embodiments, a subject is administered up to about 300 milligrams of a compound or salt of Formula (I) or (II) per dose. In embodiments, a subject is administered up to about 200 milligrams of a compound or salt of Formula (I) or (II) per dose. In embodiments, a subject is administered up to about 100 milligrams of a compound or salt of Formula (I) or (II) per dose. In embodiments, a subject is administered up to about 50 milligrams of a compound or salt of Formula (I) or (II) per dose. In embodiments, a subject is administered up to about 25 milligrams of a compound or salt of Formula (I) or (II) per dose. In embodiments, a subject is administered up to about 15 milligrams of a compound or salt of Formula (I) or (II) per dose.

In embodiments, a subject is administered up to about 10 milligrams of a compound or salt of Formula (I) or (II) per dose. In embodiments, a subject is administered up to about 5 milligrams of a compound or salt of Formula (I) or (II) per dose. In embodiments, a subject is administered up to about 1 milligram of A compound or salt of Formula (I) or (II) per dose. In embodiments, a subject is administered up to about 0.1 milligrams of a compound or salt of Formula (I) or (II) per dose. In embodiments, a subject is administered up to about 0.001 milligrams of a compound or salt of Formula (I) or (II) per dose.

In embodiments, the compound or salt of Formula (I) or (II) is at a concentration of about 0.9 grams per ounce of solution. In embodiments, the compound or salt of Formula (I) or (II) is at a concentration of about 0.8 grams per ounce of solution. In embodiments, the compound or salt of Formula (I) or (II) is at a concentration of about 0.7 grams per ounce of solution. In embodiments, the compound or salt of Formula (I) or (II) is at a concentration of about 0.6 grams per ounce of solution. In embodiments, the compound or salt of Formula (I) or (II) is at a concentration of about 0.5 grams per ounce of solution. In embodiments, the compound or salt of Formula (I) or (II) is at a concentration of about 0.4 grams per ounce of solution. In embodiments, the compound or salt of Formula (I) or (II) is at a concentration of about 0.3 grams per ounce of solution. In embodiments, the compound or salt of Formula (I) or (II) is at a concentration of about 0.2 grams per ounce of solution. In embodiments, the compound or salt of Formula (I) or (II) is at a concentration of about 0.1 grams per ounce of solution. In embodiments, the compound or salt of Formula (I) or (II) is at a concentration of about 0.01 grams per ounce of solution. In embodiments, the compound or salt of Formula (I) or (II) is at a concentration of about 0.001 grams per ounce of solution prepared. In embodiments, the compound or salt of Formula (I) or (II) is at a concentration of about 0.0001 grams per ounce of solution prepared. In embodiments, the compound or salt of Formula (I) or (II) is at a concentration of about 0.00001 grams per ounce of solution prepared. In embodiments, the compound or salt of Formula (I) or (II) is at a concentration of about 0.000001 grams per ounce of solution prepared.

Dosage may be measured in terms of mass amount of compound per liter of liquid formulation prepared. The concentration of a compound in the dose may be increased or decreased depending upon the strength of biological activity desired to treat or prevent any above-mentioned disorder associated with the treatment of subjects in need thereof. For instance, one embodiment may include up to 0.00001 grams of a compound or salt of Formula (I) or (II) per 100 mL of liquid formulation and up to about 10 grams of a compound or salt of Formula (I) or (II) per 100 mL of liquid formulation.

In embodiments, the compound or salt of Formula (I) or (II) have a dosage measured by percent of 100 mL of volume of liquid. In embodiments, the compound or salt of Formula (I) or (II) has a concentration of from about 0.41% to about 0.59% per 100 mL of total volume or per liter of total volume. In embodiments, the compound or salt of Formula (I) or (II) has a concentration of from about 0.42% to about 0.5% per 100 mL of total volume or per liter of total volume. In embodiments, the compound or salt of Formula (I) or (II) has a concentration of from about 0.43% to about 0.5% per 100 mL of total volume or per liter of total volume. In embodiments, the compound or salt of Formula (I) or (II) has a concentration of from about 0.44% to about 0.5% per 100 mL of total volume or per liter of total volume. In embodiments, the compound or salt of Formula (I) or (II) has a concentration of from about 0.45% to about 0.5% per 100 mL of total volume or per liter of total volume. In embodiments, the compound or salt of Formula (I) or (II) has a concentration of from about 0.46% to about 0.5% per 100 mL of total volume or per liter of total volume. In embodiments, the compound or salt of Formula (I) or (II) has a concentration of from about 0.47% to about 0.5% per 100 mL of total volume or per liter of total volume. In embodiments, the compound or salt of Formula (I) or (II) has a concentration of from about 0.48% to about 0.5% per 100 mL of total volume or per liter of total volume. In embodiments, the compound or salt of Formula (I) or (II) has a concentration of from about 0.49% to about 0.5% per 100 mL of total volume or per liter of total volume. In embodiments, the compound or salt of Formula (I) or (II) has a concentration of from about 0.50% to about 6.0% per 100 mL of total volume or per liter of total volume. In embodiments, the compound or salt of Formula (I) or (II) has a concentration of from about 0.50% to about 1.0% per 100 mL of total volume or per liter of total volume. In embodiments, the compound or salt of Formula (I) or (II) has a concentration of from about 0.50% to about 0.51% per 100 mL of total volume or per liter of total volume.

In embodiments, the compound or salt of Formula (I) or (II) has a concentration of from about 0.50% to about 0.52% per 100 mL of total volume or per liter of total volume. In embodiments, the compound or salt of Formula (I) or (II) has a concentration of from about 0.50% to about 0.53% per 100 mL of total volume or per liter of total volume. In embodiments, the compound or salt of Formula (I) or (II) has a concentration of from about 0.50% to about 0.54% per 100 mL of total volume or per liter of total volume.

In embodiments, the compound or salt of Formula (I) or (II) has a concentration of from about 0.50% to about 0.55% per 100 mL of total volume or per liter of total volume. In embodiments, the compound or salt of Formula (I) or (II) has a concentration of from about 0.50% to about 0.56% per 100 mL of total volume or per liter of total volume. In embodiments, the compound or salt of Formula (I) or (II) has a concentration of from about 0.50% to about 0.57% per 100 mL of total volume or per liter of total volume. In embodiments, the compound or salt of Formula (I) or (II) has a concentration of from about 0.50% to about 0.58% per 100 mL of total volume or per liter of total volume. In embodiments, the compound or salt of Formula (I) or (II) has a concentration of from about 0.50% to about 0.59% per 100 mL of total volume or per liter of total volume.

In one aspect, the present disclosure provides a composition comprising: (a) non-bonded beta-alanine, or a pharmaceutically acceptable salt thereof, at a weight to volume percent from about 0.1% to about 5.0%; (b) non-bonded 2-aminoadipic acid, or a pharmaceutically acceptable salt thereof, at a weight to volume percent from about 0.1% to about 5.0%; (c) non-bonded aspartic acid, or a pharmaceutically acceptable salt thereof, at a weight to volume percent from about 0.1% to about 5.0%; (d) non-bonded cystathionine (0.2%), or a pharmaceutically acceptable salt thereof, at a weight to volume percent from about 0.1% to about 5.0%; (e) non-bonded cysteine, or a pharmaceutically acceptable salt thereof, at a weight to volume percent from about 0.1% to about 5.0%; (f) non-bonded ethanolamine, or a pharmaceutically acceptable salt thereof, at a weight to volume percent from about 0.1% to about 5.0%; (g) non-bonded glutamic acid, or a pharmaceutically acceptable salt thereof, at a weight to volume percent from about 0.1% to about 5.0%, (h) non-bonded homocysteine, or a pharmaceutically acceptable salt thereof, at a weight to volume percent from about 0.1% to about 5.0%; (i) non-bonded hydroxyproline, or a pharmaceutically acceptable salt thereof, at a weight to volume percent from about 0.1% to about 5.0%; (j) non-bonded phosphoethanolamine, or a pharmaceutically acceptable salt thereof, at a weight to volume percent from about 0.1% to about 5.0%; (j) non-bonded phosphoserine, or a pharmaceutically acceptable salt thereof, at a weight to volume percent from about 0.1% to about 5.0%; or (k) a combination of two or more of (a), (b), (c), (d), (e), (f), (g), (h), (i), and (j).

In one aspect, the present disclosure provides a composition comprising: (a) non-bonded beta-alanine or a pharmaceutically acceptable salt thereof; (b) non-bonded 2-aminoadipic acid or a pharmaceutically acceptable salt thereof; (c) non-bonded aspartic acid or a pharmaceutically acceptable salt thereof; (d) non-bonded cystathionine or a pharmaceutically acceptable salt thereof; (e) non-bonded cysteine or a pharmaceutically acceptable salt thereof; (f) non-bonded ethanolamine or a pharmaceutically acceptable salt thereof; (g) non-bonded glutamic acid or a pharmaceutically acceptable salt thereof; (h) non-bonded homocysteine or a pharmaceutically acceptable salt thereof; (i) non-bonded hydroxyproline or a pharmaceutically acceptable salt thereof; (j) non-bonded phosphoethanolamine or a pharmaceutically acceptable salt thereof; (j) non-bonded phosphoserine or a pharmaceutically acceptable salt thereof; or (k) a combination of two or more of (a), (b), (c), (d), (e), (f), (g), (h), (i), and (j).

In embodiments, the composition comprises (c). In embodiments, the composition comprises (e). In embodiments, the composition comprises (g). In embodiments, the composition comprises (c) and (e). In embodiments, the composition comprises (c) and (g). In embodiments, the composition comprises (e) and (g). In embodiments, the composition comprises (c), (e), and (g).

In embodiments, (c) is at a weight to volume percent of about 0.4% to about 0.6%; (e) is at a weight to volume percent of about 0.4% to about 0.6%; and (g) is at a weight to volume percent of about 0.4% to about 0.6%. In embodiments, (c) is L-aspartic acid; (e) is L-cysteine; and (g) is L-glutamic acid. In embodiments, (c) is L-aspartic acid at a weight to volume percent of about 0.5%; (e) is L-cysteine at a weight to volume percent of about 0.5%; and (g) is L-glutamic acid at a weight to volume percent of about 0.5%. In embodiments, (c) is L-aspartic acid at a weight to volume percent of about 0.4%; (e) is L-cysteine at a weight to volume percent of about 0.4%; and (g) is L-glutamic acid at a weight to volume percent of about 0.4%. In embodiments, (c) is L-aspartic acid at a weight to volume percent of about 2%; (e) is L-cysteine at a weight to volume percent of about 2%; and (g) is L-glutamic acid at a weight to volume percent of about 2%.

In embodiments, the composition comprises (a), (b), (c), (d), (e), (f), (g), (h), (i), and (j). In embodiments, the composition comprises two of (a), (b), (c), (d), (e), (f), (g), (h), (i), and (j). In embodiments, the composition comprises three of (a), (b), (c), (d), (e), (f), (g), (h), (i), and (j). In embodiments, the composition comprises four of (a), (b), (c), (d), (e), (f), (g), (h), (i), and (j). In embodiments, the composition comprises five of (a), (b), (c), (d), (e), (f), (g), (h), (i), and (j). In embodiments, the composition comprises six of (a), (b), (c), (d), (e), (f), (g), (h), (i), and (j). In embodiments, the composition comprises seven of (a), (b), (c), (d), (e), (f), (g), (h), (i), and (j). In embodiments, the composition comprises eight of (a), (b), (c), (d), (e), (f), (g), (h), (i), and (j). In embodiments, the composition comprises nine of (a), (b), (c), (d), (e), (f), (g), (h), (i), and (j).

In embodiments, the composition is free of non-bonded tyrosine or a salt thereof. In embodiments, the composition is free of non-bonded phenylalanine or a pharmaceutically acceptable salt thereof, at a weight percent from about 0.5% to about 4.0%. In embodiments, the composition is free of non-bonded valine or a pharmaceutically acceptable salt thereof at a weight percent from about 0.5% to about 4.0%. In embodiments, the composition is free of non-bonded arginine, or a pharmaceutically acceptable salt thereof, at a weight percent from about 0.5% to about 4.0%. In embodiments, the composition is free of non-bonded methionine, or a pharmaceutically acceptable salt thereof, at a weight percent from about 0.5% to about 4.0%. In embodiments, the composition is free of non-bonded serine, or a pharmaceutically acceptable salt thereof, at a weight percent from about 0.5% to about 4.0%. In embodiments, the composition is free of non-bonded threonine, or a pharmaceutically acceptable salt thereof, at a weight percent from about 0.5% to about 4.0%. In embodiments, the composition is free of non-bonded leucine, or a pharmaceutically acceptable salt thereof, at a weight percent from about 0.5% to about 4.0%. In embodiments, the composition is free of non-bonded isoleucine, or a pharmaceutically acceptable salt thereof, at a weight percent from about 0.5% to about 4.0%. In embodiments, the composition is free of non-bonded citrulline, or a pharmaceutically acceptable salt thereof, at a weight percent from about 0.5% to about 4.0%. In embodiments, the composition is free of non-bonded alanine, or a pharmaceutically acceptable salt thereof, at a weight percent from about 0.5% to about 4.0%. In embodiments, the composition is free of non-bonded asparagine, or a pharmaceutically acceptable salt thereof, at a weight percent from about 0.5% to about 4.0%. In embodiments, the composition is free of non-bonded glycine, or a pharmaceutically acceptable salt thereof, at a weight percent from about 0.5% to about 4.0%. In embodiments, the composition is free of non-bonded taurine, or a pharmaceutically acceptable salt thereof, at a weight percent from about 0.5% to about 4.0%. In embodiments, the composition is free of non-bonded tryptophan, or a pharmaceutically acceptable salt thereof, at a weight percent from about 0.5% to about 4.0%. In embodiments, the composition is free of non-bonded cystathione, or a pharmaceutically acceptable salt thereof, at a weight percent from about 0.5% to about 4.0%. In embodiments, the composition is free of non-bonded 1-methylhistidine, or a pharmaceutically acceptable salt thereof, at a weight percent from about 0.5% to about 4.0%. In embodiments, the composition is free of non-bonded 2 aminobutyric acid, or a pharmaceutically acceptable salt thereof, at a weight percent from about 0.5% to about 4.0%. In embodiments, the composition is free of non-bonded glutamine, or a pharmaceutically acceptable salt thereof, at a weight percent from about 0.5% to about 4.0%. In embodiments, the composition is free of non-bonded histidine, or a pharmaceutically acceptable salt thereof, at a weight percent from about 0.5% to about 4.0%. In embodiments, the composition is free of non-bonded ornithine, or a pharmaceutically acceptable salt thereof, at a weight percent from about 0.5% to about 4.0%. In embodiments, the composition is free of non-bonded lysine, or a pharmaceutically acceptable salt thereof, at a weight percent from about 0.5% to about 4.0%.

In embodiments, the composition is free of one or more of: non-bonded alanine or salt thereof, non-bonded arginine or a salt thereof, non-bonded asparagine or a salt thereof, non-bonded citrulline or a salt thereof, non-bonded glycine or a salt thereof, non-bonded isoleucine or a salt thereof, non-bonded leucine or a salt thereof, non-bonded lysine or a salt thereof, non-bonded methionine or a salt thereof, non-bonded 3-methylhistidine or a salt thereof, non-bonded phenylalanine or a salt thereof, non-bonded ornithine or a salt thereof, non-bonded proline or a salt thereof, non-bonded serine or a salt thereof, non-bonded taurine or a salt thereof, non-bonded threonine or a salt thereof, non-bonded tryptophan or a salt thereof, and non-bonded valine or a salt thereof.

In one aspect, the disclosure provides a pharmaceutical composition comprising the composition described herein and a pharmaceutically acceptable carrier. In embodiments, the pharmaceutically acceptable carrier is sterile saline.

In one aspect, the disclosure provides a composition comprising about 0.5% L-cysteine, about 0.5% L-glutamic acid, and about 0.5% L-aspartic acid. In one aspect, the disclosure provides a composition comprising about 0.4% L-cysteine, about 0.4% L-glutamic acid, and about 0.4% L-aspartic acid. In one aspect, the disclosure provides a composition comprising about 0.3% L-cysteine, about 0.3% L-glutamic acid, and about 0.3% L-aspartic acid. In one aspect, the disclosure provides a composition comprising about 0.2% L-cysteine, about 0.2% L-glutamic acid, and about 0.2% L-aspartic acid. In one aspect, the disclosure provides a composition comprising about 0.1% L-cysteine, about 0.1% L-glutamic acid, and about 0.1% L-aspartic acid. In one aspect, the disclosure provides a composition comprising about 0.6% L-cysteine, about 0.6% L-glutamic acid, and about 0.6% L-aspartic acid. In one aspect, the disclosure provides a composition comprising about 0.7% L-cysteine, about 0.7% L-glutamic acid, and about 0.7% L-aspartic acid. In one aspect, the disclosure provides a composition comprising about 0.8% L-cysteine, about 0.8% L-glutamic acid, and about 0.8% L-aspartic acid. In one aspect, the disclosure provides a composition comprising about 0.9% L-cysteine, about 0.9% L-glutamic acid, and about 0.9% L-aspartic acid. In one aspect, the disclosure provides a composition comprising about 1% L-cysteine, about 1% L-glutamic acid, and about 1% L-aspartic acid. In one aspect, the disclosure provides a composition comprising from about 0.49% to about 0.51% L-cysteine, from about 0.49% to about 0.51% L-glutamic acid, and from about 0.49% to about 0.51% L-aspartic acid. In one aspect, the disclosure provides a composition comprising from about 0.48% to about 0.52% L-cysteine, from about 0.48% to about 0.52% L-glutamic acid, and from about 0.48% to about 0.52% L-aspartic acid. In one aspect, the disclosure provides a composition comprising from about 0.47% to about 0.53% L-cysteine, from about 0.47% to about 0.53% L-glutamic acid, and from about 0.47% to about 0.53% L-aspartic acid. In one aspect, the disclosure provides a composition comprising from about 0.46% to about 0.54% L-cysteine, from about 0.46% to about 0.54% L-glutamic acid, and from about 0.46% to about 0.54% L-aspartic acid. In one aspect, the disclosure provides a composition comprising from about 0.45% to about 0.55% L-cysteine, from about 0.45% to about 0.55% L-glutamic acid, and from about 0.45% to about 0.55% L-aspartic acid. In one aspect, the disclosure provides a composition comprising from about 0.44% to about 0.56% L-cysteine, from about 0.44% to about 0.56% L-glutamic acid, and from about 0.44% to about 0.56% L-aspartic acid. In one aspect, the disclosure provides a composition comprising from about 0.43% to about 0.57% L-cysteine, from about 0.43% to about 0.57% L-glutamic acid, and from about 0.43% to about 0.57% L-aspartic acid. In one aspect, the disclosure provides a composition comprising from about 0.42% to about 0.58% L-cysteine, from about 0.42% to about 0.58% L-glutamic acid, and from about 0.42% to about 0.58% L-aspartic acid. In one aspect, the disclosure provides a composition comprising from about 0.41% to about 0.59% L-cysteine, from about 0.41% to about 0.59% L-glutamic acid, and from about 0.41% to about 0.59% L-aspartic acid. In one aspect, the disclosure provides a composition comprising from about 0.4% to about 0.6% L-cysteine, from about 0.4% to about 0.6% L-glutamic acid, and from about 0.4% to about 0.6% L-aspartic acid. In one aspect, the disclosure provides a composition comprising from about 0.35% to about 0.65% L-cysteine, from about 0.35% to about 0.65% L-glutamic acid, and from about 0.35% to about 0.65% L-aspartic acid. In one aspect, the disclosure provides a composition comprising from about 0.3% to about 0.7% L-cysteine, from about 0.3% to about 0.7% L-glutamic acid, and from about 0.3% to about 0.7% L-aspartic acid. In one aspect, the disclosure provides a composition comprising from about 0.25% to about 0.75% L-cysteine, from about 0.25% to about 0.75% L-glutamic acid, and from about 0.25% to about 0.75% L-aspartic acid. In one aspect, the disclosure provides a composition comprising from about 0.2% to about 0.8% L-cysteine, from about 0.2% to about 0.8% L-glutamic acid, and from about 0.2% to about 0.8% L-aspartic acid. In one aspect, the disclosure provides a composition comprising from about 0.15% to about 0.85% L-cysteine, from about 0.15% to about 0.85% L-glutamic acid, and from about 0.15% to about 0.85% L-aspartic acid. In one aspect, the disclosure provides a composition comprising from about 0.1% to about 0.9% L-cysteine, from about 1% to about 0.9% L-glutamic acid, and from about 0.1% to about 0.9% L-aspartic acid. In one aspect, the disclosure provides a composition comprising from about 0.1% to about 1% L-cysteine, from about 0.1% to about 1% L-glutamic acid, and from about 0.1% to about 1% L-aspartic acid. In one aspect, the disclosure provides In one aspect, the disclosure provides a pharmaceutical composition comprising the composition described herein and a pharmaceutically acceptable carrier. In embodiments, the pharmaceutically acceptable carrier is sterile saline.

In one aspect, the disclosure provides a composition comprising about 0.5% L-cysteine, about 0.5% L-glutamic acid, and about 0.5% L-aspartic acid. In one aspect, the disclosure provides a composition comprising about 0.4% L-cysteine, about 0.4% L-glutamic acid, and about 0.4% L-aspartic acid. In one aspect, the disclosure provides a composition comprising about 0.2% L-cysteine, about 0.2% L-glutamic acid, and about 0.2% L-aspartic acid.

In one aspect, the disclosure provides a composition comprising: (a) non-bonded beta-alanine, or a pharmaceutically acceptable salt thereof, at a weight to volume percent from about 0.1% to about 5.0%; (b) non-bonded 2-aminoadipic acid, or a pharmaceutically acceptable salt thereof, at a weight to volume percent from about 0.1% to about 5.0%; (c) non-bonded aspartic acid, or a pharmaceutically acceptable salt thereof, at a weight to volume percent from about 0.1% to about 5.0%; (d) non-bonded cystathionine (0.2%), or a pharmaceutically acceptable salt thereof, at a weight to volume percent from about 0.1% to about 5.0%; (e) non-bonded cysteine, or a pharmaceutically acceptable salt thereof, at a weight to volume percent from about 0.1% to about 5.0%; (f) non-bonded ethanolamine, or a pharmaceutically acceptable salt thereof, at a weight to volume percent from about 0.1% to about 5.0%; (g) non-bonded glutamic acid, or a pharmaceutically acceptable salt thereof, at a weight to volume percent from about 0.1% to about 5.0%; (h) non-bonded homocysteine, or a pharmaceutically acceptable salt thereof, at a weight to volume percent from about 0.1% to about 5.0%; (i) non-bonded hydroxyproline, or a pharmaceutically acceptable salt thereof, at a weight to volume percent from about 0.1% to about 5.0%; (j) non-bonded phosphoethanolamine, or a pharmaceutically acceptable salt thereof, at a weight to volume percent from about 0.1% to about 5.0%; (j) non-bonded phosphoserine, or a pharmaceutically acceptable salt thereof, at a weight to volume percent from about 0.1% to about 5.0%; or (k) a combination of two or more of (a), (b), (c), (d), (e), (f), (g), (h), (i), and (j).

In one aspect, the disclosure provides a composition comprising: (a) non-bonded beta-alanine or a pharmaceutically acceptable salt thereof; (b) non-bonded 2-aminoadipic acid or a pharmaceutically acceptable salt thereof; (c) non-bonded aspartic acid or a pharmaceutically acceptable salt thereof; (d) non-bonded cystathionine or a pharmaceutically acceptable salt thereof; (e) non-bonded cysteine or a pharmaceutically acceptable salt thereof; (f) non-bonded ethanolamine or a pharmaceutically acceptable salt thereof; (g) non-bonded glutamic acid or a pharmaceutically acceptable salt thereof; (h) non-bonded homocysteine or a pharmaceutically acceptable salt thereof; (i) non-bonded hydroxyproline or a pharmaceutically acceptable salt thereof; (j) non-bonded phosphoethanolamine or a pharmaceutically acceptable salt thereof; (j) non-bonded phosphoserine or a pharmaceutically acceptable salt thereof; or (k) a combination of two or more of (a), (b), (c), (d), (e), (f), (g), (h), (i), and (j).

In embodiments, the composition comprises (c). In embodiments, the composition comprises (e). In embodiments, the composition comprises (g). In embodiments, the composition comprises (c) and (e). In embodiments, the composition comprises (c) and (g). In embodiments, the composition comprises (e) and (g). In embodiments, the composition comprises (c), (e), and (g).

In embodiments, (c) is at a weight to volume percent of about 0.4% to about 0.6%; (e) is at a weight to volume percent of about 0.4% to about 0.6%; and (g) is at a weight to volume percent of about 0.4% to about 0.6%. In embodiments, (c) is L-aspartic acid; (e) is L-cysteine; and (g) is L-glutamic acid.

In embodiments, (c) is L-aspartic acid at a weight to volume percent of about 0.5%; (e) is L-cysteine at a weight to volume percent of about 0.5%; and (g) is L-glutamic acid at a weight to volume percent of about 0.5%. In embodiments, (c) is L-aspartic acid at a weight to volume percent of about 0.4%; (e) is L-cysteine at a weight to volume percent of about 0.4%; and (g) is L-glutamic acid at a weight to volume percent of about 0.4%. In embodiments, (c) is L-aspartic acid at a weight to volume percent of about 2%; (e) is L-cysteine at a weight to volume percent of about 2%; and (g) is L-glutamic acid at a weight to volume percent of about 2%.

In embodiments, the composition comprises (a), (b), (c), (d), (e), (f), (g), (h), (i), and (j). In embodiments, the composition comprises two of (a), (b), (c), (d), (e), (f), (g), (h), (i), and (j). In embodiments, the composition comprises three of (a), (b), (c), (d), (e), (f), (g), (h), (i), and (j). In embodiments, the composition comprises four of (a), (b), (c), (d), (e), (f), (g), (h), (i), and (j). In embodiments, the composition comprises five of (a), (b), (c), (d), (e), (f), (g), (h), (i), and (j). In embodiments, the composition comprises six of (a), (b), (c), (d), (e), (f), (g), (h), (i), and (j). In embodiments, the composition comprises seven of (a), (b), (c), (d), (e), (f), (g), (h), (i), and (j). In embodiments, the composition comprises eight of (a), (b), (c), (d), (e), (f), (g), (h), (i), and (j). IN embodiments, the composition comprises nine of (a), (b), (c), (d), (e), (f), (g), (h), (i), and (j).

In embodiments, the composition is free of non-bonded tyrosine or a salt thereof. In embodiments, the composition is free of non-bonded phenylalanine or a pharmaceutically acceptable salt thereof, at a weight percent from about 0.5% to about 4.0%. In embodiments, the composition is free of non-bonded valine or a pharmaceutically acceptable salt thereof at a weight percent from about 0.5% to about 4.0%. In embodiments, the composition is free of non-bonded arginine, or a pharmaceutically acceptable salt thereof, at a weight percent from about 0.5% to about 4.0%. In embodiments, the composition is free of non-bonded methionine, or a pharmaceutically acceptable salt thereof, at a weight percent from about 0.5% to about 4.0%. In embodiments, the composition is free of non-bonded serine, or a pharmaceutically acceptable salt thereof, at a weight percent from about 0.5% to about 4.0%. In embodiments, the composition is free of non-bonded threonine, or a pharmaceutically acceptable salt thereof, at a weight percent from about 0.5% to about 4.0%. In embodiments, the composition is free of non-bonded leucine, or a pharmaceutically acceptable salt thereof, at a weight percent from about 0.5% to about 4.0%. In embodiments, the composition is free of non-bonded isoleucine, or a pharmaceutically acceptable salt thereof, at a weight percent from about 0.5% to about 4.0%. In embodiments, the composition is free of non-bonded citrulline, or a pharmaceutically acceptable salt thereof, at a weight percent from about 0.5% to about 4.0%. In embodiments, the composition is free of non-bonded alanine, or a pharmaceutically acceptable salt thereof, at a weight percent from about 0.5% to about 4.0%. In embodiments, the composition is free of non-bonded asparagine, or a pharmaceutically acceptable salt thereof, at a weight percent from about 0.5% to about 4.0%. In embodiments, the composition is free of non-bonded glycine, or a pharmaceutically acceptable salt thereof, at a weight percent from about 0.5% to about 4.0%. In embodiments, the composition is free of non-bonded taurine, or a pharmaceutically acceptable salt thereof, at a weight percent from about 0.5% to about 4.0%. In embodiments, the composition is free of non-bonded tryptophan, or a pharmaceutically acceptable salt thereof, at a weight percent from about 0.5% to about 4.0%. In embodiments, the composition is free of non-bonded cystathione, or a pharmaceutically acceptable salt thereof, at a weight percent from about 0.5% to about 4.0%. In embodiments, the composition is free of non-bonded 1-methylhistidine, or a pharmaceutically acceptable salt thereof, at a weight percent from about 0.5% to about 4.0%. In embodiments, the composition is free of non-bonded 2 aminobutyric acid, or a pharmaceutically acceptable salt thereof, at a weight percent from about 0.5% to about 4.0%. In embodiments, the composition is free of non-bonded glutamine, or a pharmaceutically acceptable salt thereof, at a weight percent from about 0.5% to about 4.0%. In embodiments, the composition is free of non-bonded histidine, or a pharmaceutically acceptable salt thereof, at a weight percent from about 0.5% to about 4.0%. In embodiments, the composition is free of non-bonded ornithine, or a pharmaceutically acceptable salt thereof, at a weight percent from about 0.5% to about 4.0%. In embodiments, the composition is free of non-bonded lysine, or a pharmaceutically acceptable salt thereof, at a weight percent from about 0.5% to about 4.0%.

In embodiments, the composition is free of one or more of: non-bonded alanine or salt thereof, non-bonded arginine or a salt thereof, non-bonded asparagine or a salt thereof, non-bonded citrulline or a salt thereof, non-bonded glycine or a salt thereof, non-bonded isoleucine or a salt thereof, non-bonded leucine or a salt thereof, non-bonded lysine or a salt thereof, non-bonded methionine or a salt thereof, non-bonded 3-methylhistidine or a salt thereof, non-bonded phenylalanine or a salt thereof, non-bonded ornithine or a salt thereof, non-bonded proline or a salt thereof, non-bonded serine or a salt thereof, non-bonded taurine or a salt thereof, non-bonded threonine or a salt thereof, non-bonded tryptophan or a salt thereof, and non-bonded valine or a salt thereof.

In one aspect, the disclosure provides a pharmaceutical composition comprising the composition described herein and a pharmaceutically acceptable carrier. In embodiments, the pharmaceutical composition of Embodiment N50, wherein the pharmaceutically acceptable carrier is sterile saline.

Combination Therapies

In embodiments, the disclosure provides a compound or salt thereof in a pharmaceutical composition, wherein the pharmaceutical composition further comprises another active agent besides the compound or salt of Formula (I) or (II). In embodiments, the other active agent is an antibiotic or an antifungal agent.

Examples of macrolide antibiotics that may be used in combination with a compound or salt of Formula (I) or (II) include, but are not limited to, inter alia: tacrolimus, cyclosporine, sirolimus, everolimus, ascomycin, erythromycin, azithromycin, clarithromycin, clindamycin, lincomycin, dirithromycin, josamycin, spiramycin, diacetyl-midecamycin, tylosin, roxithromycin, ABT-773, telithromycin, leucomycins, and lincosamide. Other antibiotics include, but are not limited to, aminoglycosides (e.g., streptomycin, amikacin, gentamicin, tobramycin), cephalosporins (e.g., beta lactams including penicillin), tetracyclines, acyclorvir, amantadine, polymyxin B, amphtotericin B, amoxicillin, ampicillin, atovaquone, azithromycin, azithromycin, bacitracin, cefazolin, cefepime, cefotaxime, cefotetan, cefpodoxime, ceftazidime, ceftizoxime, ceftriaxone, cefuroxime, cephalexin, chloramphenicol, clotimazole, ciprofloxacin, clarithromycin, clindamycin, dapsone, dicloxacillin, fluconazole, foscamet, ganciclovir, gatifloxacin, griseofulvin, isoniazid, itraconazole, ketoconazole, metronidazole, nafcillin, neomycin, nitrofurantoin, nystatin, pentamidine, rifampin, rifamycin, valacyclovir, vancomycin, etc. The indications, effective doses, formulations, contraindications, vendors, etc. of these antibiotics are known to one skilled in the art.

In embodiments, the antibiotic is a cephalosporin. Examples of cephalosporins include, but are not limited to, Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef and Ceftolozane. In one embodiment the cephalosporin is Ceftolozane or Ceftazidime.

In one embodiment, the antibiotic is a carbapenen. Examples of carbapenem antibiotics include, but are not limited to, Imipenem, Imipenem/Cilastatin, Biapenem, Doripenem, Meropenem, Ertapenem and Panipenem. In one embodiment the Carbapenem is Imipenem/Cilastatin or Meropenem. In one embodiment, the antibiotic is a monobactam. Examples of monobactam antibiotics include, but are not limited to Aztreonam, Tigemonam, Carumonam, BAL30072 and Nocardicin A. In one embodiment, the antibiotic is a penem. In one embodiment, the antibiotic is a penicillin. Examples of penicillin antibiotics include, but are not limited to Amoxicillin, Ampicillin, Azlocillin, Mezlocillin, Apalcillin, Hetacillin, Becampicillin, Carbenicillin, Sulbenicillin, Ticarcillin, Piperacillin, Azlocillin, Mecillinam, Pivmecillinam, Methicillin, Ciclacillin, Talampicillin, Aspoxicillin, Oxacillin, Cloxacillin, Dicloxacillin, Flucloxacillin, Nafcillin and Pivampicillin. In one embodiment the cephalosporin is Ceftolozane, Ceftazidime, Aztreonam or Meropenem, or more preferably, Ceftolozane or Ceftazidime.

In embodiments, the other active agent or pharmaceutically acceptable salt thereof is an antifungal agent. For example, in embodiments, the antifungal agent is a polyene (for instance, amphotericin B), an azole (for instance, fluconazole), an echinocandin (for instance, caspofungin), a nucleoside analog (for instance, 5-fluorocytosine), an allylamine (for instance, naftifine, terbinafine, or butenafine), or other antifungal agents (for instance, ciclopirox). Examples of polyenes include, e.g., nystatin, amphotericin B, and leukotriene, or pharmaceutically acceptable salts thereof. Examples of azoles include miconazole, clotrimazole, ketoconazole, oxiconazole, eberconazole, econazole, sulconazole, sertaconazle, bifonazole, butoconazole, fenticonazole, isoconazole, omoconazole and tioconazole, or pharmaceutically acceptable salts thereof. Examples of echinocandins include caspofungin, pneumocandins, echinocandin B, ciliofungin, micafungin, and anidulafungin, or pharmaceutically acceptable salts thereof. Examples of nucleoside analogs include 5-fluorocytosine, or pharmaceutically acceptable salts thereof. Examples of allylamines include naftifine, terbinafine, and amorolfin, and butenafine, or pharmaceutically acceptable salts thereof. Exemplary other antifungals include ciclopirox, or selenium sulfide. Additional antifungals include agents that block NA synthesis including, e.g., flucytosine, and those that disrupt microtubule function including, e.g., griseofulvin. Suitable antifungals can include one of candicidin, filipin, hamycin, natamycin, and rimocidin. Triazoles, including albaconazole, fluconazole, isavuconazole, itraconazole, posaconazole, ravuconazole, terconazole, and voriconazole are also suitable antifungal active agents. Also suitable are, thiazoles including, e.g., abafungin. Suitable antifungal agents include, e.g., of amorolfin, butenafine, naftifine, and terbinafine. In addition, echinocandins, including anidulafungin, caspofungin, and micafungin, are suitable antifungals. Also suitable are griseofulvin, benzoic acid, ciclopirox, haloprogin, polygodial, tolnaftate, undecylenic acid, and Crystal violet Suitable antifungal agents include, but are not limited to, natifine, butenafine, terbinafine, and amorolfine, as well as any pharmaceutically acceptable salts thereof. Suitable salts of antifungal agents include but are not limited to hydrochloride salts. In embodiments, certain antifungal agents or pharmaceutically acceptable salts thereof are believed to act by interfering with squalene 2,3-epoxidase, which results in decreased amounts of the principal membrane sterols, especially ergosterol.

Naftifine and pharmaceutically acceptable salts thereof have fungicidal activity against organisms, including but not limited to, dermatophytes, including for example, *Trichophyton rubrum, Trichophyton interdigitale, Trichophyton verrucosum, Trichophyton mentagrophytes, Trichophyton megninii, Trichophyton tonsurans, Trichophyton schoenleinii, Trichophyton soudanense, Trichophyton violaceum, Epidermophyton floccosum, Microsporum audouini, Microsporum canis, Microsporum distortum, Microsporum gypseum*; nondermatophyte molds including, for example, *Scopulariopsis brevicaulis, Fusarium* spp., *Aspergillus* spp., *Alternaria, Acremonium, Scytalidinum dimidiatum*, and *Scytalidinium hyalinum*; and *Candida* spp. including, for example, *Candida albicans*, and *Candida parapsilosis*.

Butenafine and pharmaceutically acceptable salts thereof, for example, butenafine hydrochloride, have fungicidal activity against organisms, including but not limited to, dermatophytes, including for example, *Trichophyton rubrum, Trichophyton mentagrophytes, Trichophyton tonsurans, Epidermophyton floccosum, Microsporum canis*; nondermatophyte molds including, for example, *Aspergillus* spp.; *Candida* spp. including, for example, *Candida albicans* and *Candida parapsilosis; Malassezia furfur*; and *Cryptococcus*.

Terbinafine and pharmaceutically acceptable salts thereof, for example, terbinafine hydrochloride, is active against many fungi, including dermatophytes (*Trichophyton, Microsporum, Epidermophyton*), filamentous (e.g. *Aspergillus*), dimorphic (e.g., *Blastomyces*), and dematiaceous fungi and yeasts. Terbinifine has an antifungal spectrum of activity similar to that of naftifine. More specifically, Terbinafine and pharmaceutically acceptable salts thereof, for example, butenafine hydrochloride, have fungicidal activity against organisms, including but not limited to, dermatophytes, including for example, *Trichophyton rubrum, Trichophyton mentagrophytes, Trichophyton tonsurans, Trichophyton violaceum, Epidermophyton floccosum, Microsporum audouini, Microsporum canis*; nondermatophyte molds including, for example, *Aspergillus* spp. and *Scopulariopsis brevicaulis; Candida* spp. including, for example, *Candida albicans* and *Candida parapsilosis; Blastomyces*; and *Histoplasma*. Amorolfine and pharmaceutically acceptable salts thereof, for example, amorolfine hydrochloride, is active against many fungi, including dermatophytes (*Trichophyton, Microsporum, Epidermophyton*), filamentous (e.g. *Aspergillus*), dimorphic (e.g., *Blastomyces* and *Sporothrix schenckii*), dematiaceous fungi and yeasts, and *Sporothrix schenckii*. Amorolfine and pharmaceutically acceptable salts thereof, for example, amorolfin hydrochloride, have fungicidal activity against organisms, including but not limited to, dermatophytes including, for example, *Trichophyton rubrum, Trichophyton mentagrophytes, Epidermophyton floccosum*; nondermatophyte molds including, for example, *Scopulariopsis* spp. including *Scopulariopsis brevicaulis, Fusarium* spp. including *Fusarium solani, Aspergillus* spp. including *Aspergillus flavus*, and *Acremonium* spp.; *Candida* spp. including, for example, *Candida albicans* and *Candida parapsilosis*; and *Malassezia* spp. including *Malassezia furfur*. In embodiments, an antifungal agent is selected from the group consisting of naftifine, butenafine, terbinafine, and amorolfine. In embodiments, the antifungal agent is butenafine. In embodiments, the antifungal agent is terbinafine. In embodiments, the antifungal agent is amorolfine.

Methods for making the presently described antifungal agents and pharmaceutically acceptable salts thereof are disclosed in U.S. Pat. Nos. 4,755,534; 4,680,291; and 4,282,251, each of which is incorporated by reference herein in its entirety.

Methods of Treatment

The disclosure provides compounds, salts thereof and compositions for treating a bacterial infection or a fungal infection. In embodiments, the methods provided herein can be used to treat bacterial infections or fungal infections by inhibiting the formation of bacterial biofilm or fungal biofilm. In embodiments, the methods provided herein can be used to treat bacterial infections or fungal infections by disrupting the formation of bacterial biofilm or fungal biofilm.

In embodiments, the disclosure provides a method of treating bacterial or fungal infection, the method comprising administering a composition comprising a compound of formula (I) or (II):

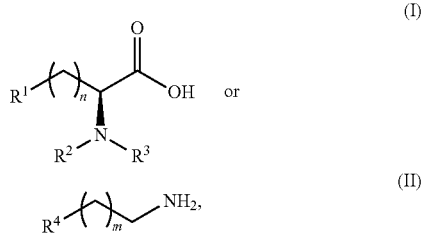

or a salt thereof wherein: $R^1$ is selected from —$SR^5$, —C(O)$R^5$, —OC(O)$R^5$, —C(O)O$R^5$, —C(O)N($R^5$)$_2$, —N$R^5$C(O), and —OP(=O)(O$R^5$)$_2$; $R^2$ and $R^3$ is hydrogen or, at least one of $R^2$ and $R^3$ is hydrogen and the other of $R^2$ and $R^3$ with $R^1$ is taken together with the atoms to which they are attached to form a heterocycle substituted with one or more $R^6$; $R^4$ is selected from —O$R^5$, —N($R^5$)$_2$, —C(O)O$R^5$, —OC(O)$R^5$, C(O)N($R^5$)$_2$, —N$R^5$C(O), and —OP(=O)(O$R^5$)$_2$; $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$; $R^6$ is independently selected at each occurrence from halogen, —NO$_2$, —CN, —O$R^5$, —S$R^5$, —N($R^5$)$_2$, —C(O)$R^5$, —C(O)O$R^5$, —OC(O)$R^5$, —OC(O)O$R^5$, —OC(O)N($R^5$)$_2$, —N$R^5$C(O)$R^5$, —C(O)N($R^5$)$_2$, =O, =S, =N($R^5$), $C_{1-10}$ alkyl, $C_{2-10}$ alkenyl, and $C_{2-10}$ alkynyl, each of which is independently optionally substituted at each occurrence with one or more substituents selected from halogen, —CN, —NO$_2$, —OH, —NH$_2$, —COOH, and —OCH$_3$; and n and m are independently selected from 0, 1, 2, 3, 4, or 5.

In embodiments, the disclosure provides composition comprising a compound of formula (I) or (II):

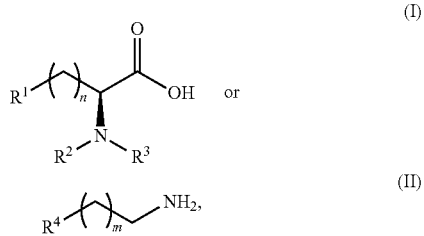

or a salt thereof wherein: $R^1$ is selected from —$SR^5$, —C(O)$R^5$, —OC(O)$R^5$, —C(O)O$R^5$, —C(O)N($R^5$)$_2$, —N$R^5$C(O), and —OP(=O)(O$R^5$)$_2$; $R^2$ and $R^3$ is hydrogen or, at least one of $R^2$ and $R^3$ is hydrogen and the other of $R^2$ and $R^3$ with $R^1$ is taken together with the atoms to which they are attached to form a heterocycle substituted with one or more $R^6$; $R^4$ is selected from —O$R^5$, —N($R^5$)$_2$, —C(O)O$R^5$, —OC(O)$R^5$, C(O)N($R^5$)$_2$, —N$R^5$C(O), and —OP(=O)(O$R^5$)$_2$; $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$; $R^6$ is independently selected at each occurrence from halogen, —NO$_2$, —CN, —O$R^5$, —S$R^5$, —N($R^5$)$_2$, —C(O)$R^5$, —C(O)O$R^5$, —OC(O)$R^5$, —OC(O)O$R^5$, —OC(O)N($R^5$)$_2$, —N$R^5$C(O)$R^5$, —C(O)N($R^5$)$_2$, =O, =S, =N($R^5$), $C_{1-10}$ alkyl, $C_{2-10}$ alkenyl, and $C_{2-10}$ alkynyl, each of which is independently optionally substituted at each occurrence with one or more substituents selected from halogen, —CN, —NO$_2$, —OH, —NH$_2$, —COOH, and —OCH$_3$; and n and m are independently selected from 0, 1, 2, 3, 4, or 5, for use in the treatment of a bacterial or fungal infection.

In embodiments, the disclosure provides a composition comprising a compound of formula (I) or (II):

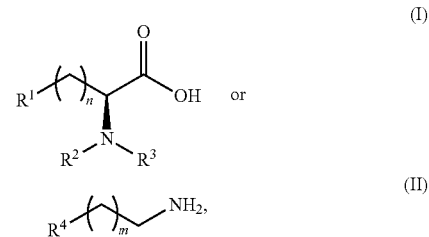

or a salt thereof wherein: $R^1$ is selected from —$SR^5$, —C(O)$R^5$, —OC(O)$R^5$, —C(O)O$R^5$, —C(O)N($R^5$)$_2$, —N$R^5$C(O), and —OP(=O)(O$R^5$)$_2$; $R^2$ and $R^3$ is hydrogen or, at least one of $R^2$ and $R^3$ is hydrogen and the other of $R^2$ and $R^3$ with $R^1$ is taken together with the atoms to which they are attached to form a heterocycle substituted with one or more $R^6$; $R^4$ is selected from —O$R^5$, —N($R^5$)$_2$, —C(O)O$R^5$, —OC(O)$R^5$, C(O)N($R^5$)$_2$, —N$R^5$C(O), and —OP(=O)(O$R^5$)$_2$; $R^5$ is independently selected at each occurrence from hydrogen; and $C_{1-6}$ alkyl, $C_{2-6}$ alkenyl, $C_{2-6}$ alkynyl, $C_{3-12}$ carbocycle and 3- to 12-membered heterocycle, each of which is independently optionally substituted at each occurrence by halogen, —CN, —NO$_2$, —OH, —NH$_2$, —COOH, and —OCH$_3$; $R^6$ is independently selected at each occurrence from halogen, —NO$_2$, —CN, —O$R^5$, —S$R^5$, —N($R^5$)$_2$, —C(O)$R^5$, —C(O)O$R^5$, —OC(O)$R^5$, —OC(O)O$R^5$, —OC(O)N($R^5$)$_2$, —N$R^5$C(O)$R^5$, —C(O)N($R^5$)$_2$, =O, =S, =N($R^5$), $C_{1-10}$ alkyl, $C_{2-10}$ alkenyl, and $C_{2-10}$ alkynyl, each of which is independently optionally substituted at each occurrence with one or more substituents selected from halogen, —CN, —NO$_2$, —OH, —NH$_2$, —COOH, and —OCH$_3$; and n and m are independently selected from 0, 1, 2, 3, 4, or 5 for use in the manufacture of a medicament for the treatment of a bacterial or fungal infection.

In embodiments of the methods described herein, the fungal infection is infection with a *Candida* species fungus, e.g., *C. albicans*. In embodiments, the bacterial infection is a bacterial infection caused by antibiotic-resistant bacteria. In embodiments, the infection is a fungus which produces a biofilm. In embodiments, the infection is a bacterium which produces a biofilm. In embodiments, the bacterial cells that induce infection are one or a plurality of bacterial cells derived from or chosen from one or a plurality: *Streptococ-*

*cus pneumoniae, Streptococcus mutans, Bacillus* spp, *Listeria monocytogenes, Staphylococcus* spp, and lactic acid bacteria, including *Lactobacillus plantarum* and *Lactococcus lactis*.

The pharmaceutical composition comprising a compound or salt of formula (I) or (II) may be used to treat a bacterial infection and/or a fungal infection of any organ or tissue or wound in the body of a subject caused by antibiotic-resistant bacteria and/or fungal cells, including, antibiotic-resistant Gram-negative beta-lactam resistant bacteria. These organs or tissue include, without limitation, skeletal muscle, skin, mucous membrane, bloodstream, kidneys, heart, lung, bone, and nervous system. For example, a pharmaceutical composition comprising a compound or salt of formula (I) or (II) in conjunction with an antibiotic, may be administered to a subject to treat, without limitation, skin and soft tissue infections (e.g., complex skin infections), bacteremia, intra-abdominal infections and urinary tract infections (e.g., cUTI). In addition, a composition comprising a compound or salt of formula (I) or (II) may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *Pseudomonas aeruginosa*. At least one composition comprising a compound or salt of formula (I) or (II) in conjunction with an antibiotic, may be administered to a subject to treat mixed infections that comprise different types of Gram-negative bacteria, or which comprise both Gram-positive and Gram-negative bacteria. These types of infections include intra-abdominal infections and obstetrical/gynecological infections. At least one composition comprising a compound or salt of formula (I) or (II) optionally in conjunction with an antibiotic, may also be administered to a subject to treat an infection including, without limitation, endocarditis, nephritis, septic arthritis, intra-abdominal sepsis, bone and joint infections, sinusitis, osteomyelitis, and nervous system infection. At least one composition comprising a compound or salt of formula (I) or (II) optionally in conjunction with an antibiotic, or pharmaceutical composition comprising a compound or salt of formula (I) or (II) may also be directly injected or administered into an abscess, ventricle or joint. Pharmaceutical compositions comprising a compound or salt of formula (I) or (II) in conjunction with an antibiotic, may be administered as an aerosol for the treatment of pneumonia or other lung-based infections. In one embodiment, the aerosol delivery vehicle is an anhydrous, liquid or dry powder inhaler.

In embodiments, viral bacteriophages make it possible to reduce or eliminate colonization and/or infection of humans and animals by pathogenic bacteria, including antibiotic resistant bacteria. Compared to antibiotics, in embodiments, phages go deeper into the infected area. Antibiotics, on the other hand and in embodiments, have concentration properties that quickly decrease as they go below the surface of the infection. The replication of phages is concentrated on the infected area where they are needed the most, while antibiotics are metabolized and removed from the body. In addition, secondary resistance does not happen among phages, but happens quite often among antibiotics. Secondary resistance is acquired and occurs when there are not enough blood drug levels. Phages, in embodiments, provide a good choice for the treatment of drug-resistant bacteria.

In embodiments, the viral bacteriophages are chosen from phages belonging to a family chosen from ampullaviridae, bicaudaviridae, clavaviridae, corticoviridae, cystoviridae, fuselloviridae, globuloviridae, guttaviridae, inoviridae, leviviridae, microviridae, plasmaviridae, tectiviridae. In embodiments, the viral bacteriophages are used as a single phage or in combination (including any other phage belonging to a family chosen from ampullaviridae, bicaudaviridae, clavaviridae, corticoviridae, cystoviridae, fuselloviridae, globuloviridae, guttaviridae, inoviridae, leviviridae, microviridae, plasmaviridae, tectiviridae, and/or others.

In embodiments, the antihistamines are chosen from azelastine, hydroxyzine, desloratadine, emadastine, levocabastine, azelastine, carbinoxamine, and levocetirizine. In embodiments, the antihistamines are chosen from fexofenadine, diphenhydramine, dimetane, loratadine, clemastine, chlorpheniramine, and certirizine. In some embodiment, the antihistamines are chosen from brompheniramine, chlorpheniramine, dimenhydrinate, and doxylamine. In embodiments, the nasal decongestants are chosen from oxymetazoline, phenylephrine, and pseudoephedrine.

In embodiments, the active ingredients are chosen from spermicidal agents, prostaglandins, and hormones.

In embodiments, the composition is used to treat a patient suffering from, or susceptible to, bacterial infection or fungal infection. In embodiments, the composition is used to treat a patient suffering from, or susceptible to, bacterial infection or fungal infection comprising a biofilm of either or both of one or plurality of bacterial cells in the form of a biofilm or fungal cells in the form of a biofilm.

In embodiments, the disclosure relates to methods of preventing bacterial biofilm formation and/or fungal biofilm formation by administration of any of the pharmaceutical compositions disclosed herein, individually or in combination, to a subject in need thereof in a prophylactically effective amount. In embodiments, the disclosure relates to methods of simultaneously preventing bacterial biofilm formation and fungal biofilm formation by administration of any of the pharmaceutical compositions disclosed herein, individually or in combination, to a subject in need thereof in a prophylactically effective amount. In embodiments, the disclosure relates to methods of treating bacterial infection caused by or comprising a bacterial biofilm and/or treating fungal infection caused by or comprising a fungal biofilm by administration of a compound or salt of formula (I) or (II) or a pharmaceutical composition comprising a compound or salt of formula (I) or (II), individually or in combination, to a subject in need thereof in a therapeutically effective amount. In embodiments, the disclosure relates to methods of simultaneously treating bacterial biofilm infections and fungal biofilm infections by administration of a compound or salt of formula (I) or (II) or a pharmaceutical composition comprising a compound or salt of formula (I) or (II) in a therapeutically effective amount, individually or in combination (sequentially or simultaneously), to a subject in need thereof.

The disclosure relates to the treatment and/or prevention of fungal infections in a subject caused by fungal cell biofilm formation. In embodiments, the fungal cells comprise one or a plurality of cells derived from: *Candida albicans, Candida guilliermondii, Candida parapsilosis, Candida glabrata, Candida tropicalis* and/or *Candida dubliniensis*.

The disclosure relates to the treatment and/or prevention of bacterial infections in a subject caused by bacterial biofilm formation. In embodiments, methods of the disclosure relate method of treatment and/or prevention of bacterial biofilm formation in a subject by administration of a therapeutically or prophylactically effective amount of a compound or salt of formula (I) or (II) or a pharmaceutical composition comprising a compound or salt of formula (I) or (II). In embodiments, the bacterial cells comprise one or a plurality of cells derived from: *Staphylococcus aureus* (standard wild type and methicillin-resistant strain USA300), *Escherichia coli, Pseudomonas aeruginosa* and/or *Staphylococcus epidermidis*.

In any embodiments of the aforementioned methods, administration may be accomplished by intravenously, topically, irrigation of wounds either as part of a wound dressing or in sterile solution, intradermally, intramucosally, subcutaneously, sublingually, orally, intravaginally, intramuscularly, intracavernously, intarocularly, intranasally, into a sinus, intrarectally, gastrointestinally, intraductally, intathecally, subdurally, extradurally, intraventricular, intrapulmonary, into an abscess, intra articular, into a bursa, subpericardially, intrauterine, into the plural space, swish and swallow treatment of oral candidiasis, transmucosal, or transdermal administration of the prophylactically or therapeutically effective amount of a composition or pharmaceutical composition disclosed herein to a subject in need thereof. In embodiments, the method comprises administration of an antibiotic prior to, simultaneously with, or subsequent to administration of the prophylactically or therapeutically effective amount of a compound or salt of formula (I) or (II) or a pharmaceutical composition comprising a compound or salt of formula (I) or (II) to a subject in need thereof. In any of the above methods, the method may comprise administration of an antibiotic or anti-fungal agent intravenously, topically, irrigation of wound either as part of wound dressing or in sterile solution, intradermally, submucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articular, into a bursa, subpericardially, intrauterine, into the plural space, into the peritoneal cavity, swish and swallow treatment of oral candidiasis, for transmucosal, or for transdermal administration.

If, for instance, the pharmaceutical compositions are administered intracavernously, the pharmaceutical compositions comprise, in embodiments, a pharmaceutically effective amount of one of the compositions disclosed herein and a pharmaceutically acceptable carrier which may be in solution form and contacted with a wound or in a solution or solid form as part of a wound dressing. The wound dressing may be physically applied in contact to a wound or the skin. In embodiments, the pharmaceutical compositions are administered as a mouth wash or rinse that is designed not to be ingested but rather swished and spit out.

The pharmaceutical compositions of the disclosure may be topically administered in any formulation, including a gel or liquid solution. A sufficient amount of the topical preparation the compound or salt of Formula (I) or (II) has be gently rubbed onto the affected area and surrounding skin, for example, in an amount sufficient to cover an affected area plus a margin of healthy skin or tissue surrounding the affected area, for example, a margin of about 0.5 inches. The compositions may be applied to any surface of the body, including for example, skin, scalp, face, eyebrows, eyelashes, bearded areas, nail surface, nail bed, nail matrix, and nail fold, as well as to the mouth, vagina, eye, nose, or other mucous membranes.

In some superficial fungal infections of the skin, the composition may be applied in a single application four times a day to once a month or, once a week, once a bi-week, once a month, or from one to four times daily, for a period of time sufficient to alleviate signs and/or symptoms or clear the fungal infection. For example, for a period of time of one week, from 1 to 12 weeks or more, from 1 to 10 weeks, from 1 to 8 weeks, from 2 to 12 weeks, from 2 to 10 weeks, from 2 to 8 weeks, from 2 to 6 weeks, from 2 to 4 weeks, from 4 to 12 weeks, from 4 to 10 weeks, from 4 to 8 weeks, from 4 to 6 weeks. The present compositions may be administered, for example, at a frequency of once per day or twice per day. The presently described compositions may be topically administered once per day for a period of time from 1 week to 8 weeks, from 1 week to 4 weeks, for 1 week, for 2 weeks, for 3 weeks, for 4 weeks, for 5 weeks, for 6 weeks, for 7 weeks, or for 8 weeks.

The presently described compositions may be applied in a therapeutically effective amount, for example, an amount sufficient to cover an affected area plus a margin of healthy skin or tissue surrounding the affected area, for example, a margin of about 0.5 inches. Suitable amounts, for example, per application per affected area or cumulative daily dosage per affected area (for example two applications in a 24-hour period), may include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

For example, generally for *Tinea corporis, Tinea cruris* or *Tinea faciei*, the present composition may be applied, for example once or twice daily, for example, morning and evening, for about 2-4 weeks. Generally for *Tinea pedis* application the present composition may be applied once daily, for 2 weeks or longer.

For example, the presently described compositions may be topically applied in an amount sufficient to cover an affected area plus a margin of healthy skin or tissue surrounding the affected area, for example, a margin of about 0.5 inches, at a frequency, for example, of once a day, for a time period, for example of about two weeks.

If desired, other therapeutic agents may be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

In embodiments, for onychomycosis infections, the compositions are applied at a frequency of from one to four times daily, for a period of six weeks for infections of the fingernails or twelve weeks for infection of the toenails. This treatment may be repeated including for example, once daily, twice daily, three times daily, or four times daily, one a daily or weekly basis, or on a monthly or every other month schedule, for a period of time sufficient to alleviate symptoms or clear the fungal infection, for example, for a period of time from 1 to 52 weeks, from 1 to 26 weeks, from 26 to 52 weeks, from 13 to 39 weeks, from 20 to 40 weeks, from 20 to 48 weeks, from 5 to 50 weeks, from 10 to 45 weeks, from 15 to 40 weeks, from 20 to 35 weeks, from 25 to 30 weeks, for about 30 weeks; from 28 weeks to 50 weeks, from 30 week to 48 weeks, from 32 to 46 weeks, from 34 to 44 weeks, from 36 to 42 weeks, from 38 to 40 weeks, from 2 to 24 weeks, from 2 to 22 weeks, from 2 to 20 weeks, from 2 to 18 weeks, from 2 to 16 weeks, from 2 to 14 weeks, from 2 to 12 weeks, from 2 to 10 weeks, from 2 to 8 weeks, from 2 to 6 weeks, from 2 to 4 weeks, from 10 to 48 weeks, from 12 to 48 weeks, from 14 to 48 weeks, from 16 to 48 weeks, from 18 to 48 weeks, from 20 to 48 weeks, from 22 weeks to 48 weeks, from 24 week to 48 weeks, from 26 to 48 weeks, from 28 to 48 weeks, from 30 to 48 weeks, from 32 to 48 weeks, from 34 to 48 weeks, from 34 to 48 weeks, from 36 to 48 weeks, from 38 to 48 weeks, from 40 to 48 weeks, from 42 to 48 weeks, from 44 to 48 weeks, from 46 to 48 weeks, for 1 weeks, for 2 weeks, for 4 weeks, for 6 weeks, for 8 weeks, for 10 weeks, for 12 weeks, for 24 weeks, for 26 weeks, for 28 weeks, for 30 weeks, for 32 weeks, for 34 weeks, for 36 weeks, for 38 weeks, for 40 weeks, for 42 weeks, for 44 weeks, for 46 weeks, for 48 weeks, for 50 weeks, for 50 weeks, or for 52 weeks. For example, the present compositions may be topically administered, at a frequency of once per day for a period of time from 1 week to 52 weeks, for example for about from 24 weeks to 48 weeks.

In embodiments, for onychomycosis infections the compositions are applied in a therapeutically effective amount, for example, an amount sufficient to cover an affected area plus a margin of healthy skin and/or nail surrounding the affected area, for example, a margin of about 0.1 to about 0.5 inches. Suitable amounts per application per affected area or cumulative daily dosage per affected area is applied.

In certain onychomycosis cases a maximum per application, per affected area, dose of 8 grams of a compound or salt of Formula (I) or (II) or a pharmaceutical composition comprising a compound or salt of Formula (I) or (II) is applied to an affected area (all nails), for example, once or twice daily. In embodiments, the present composition is applied, for example once or twice daily, for example, morning and/or evening, for about 1-52 weeks. For example, in embodiments, the presently described compositions are topically applied in an amount sufficient to cover an affected area plus a margin of healthy skin and/or nail surrounding the affected area, for example, a margin of about 0.1 to about 0.5 inches, at a frequency, for example, of once a day, for a time period, for example of about 24 to about 48 weeks.

In embodiments, the pharmaceutical composition is free of glucose. In embodiments, the pharmaceutical composition is free of glucose at about 5% weight to volume in liquid formulation.

In embodiments, a compound or salt of formula (I) or (II) or a pharmaceutical composition comprising a compound or salt of formula (I) or (II) is used topically used on humans and also used for sterilizing surgical equipment in solid or liquid surfaces that need be kept free of biofilm producing bacteria and fungi, (one or more nails and, for example, one or two applications in a 24-hour period), may include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

In embodiments, the compound or salt of formula (I) or (II) or the pharmaceutical composition comprising a compound or salt of formula (I) or (II) are given in a single or multiple doses per time period, for example, daily, weekly, bi-weekly, or monthly. For example, in embodiments, the compound or salt of formula (I) or (II) or pharmaceutical composition comprising a compound or salt of formula (I) or (II) are given from one to four times per period.

In embodiments, for superficial fungal infections of the skin, the present compositions are given once per week, for a period of from one to six weeks.

In one aspect, the present disclosure provides a method of disrupting a fungal biofilm, a bacterial biofilm, or a fungal biofilm and a bacterial biofilm, the method comprising contacting the biofilm with the composition described herein or the pharmaceutical composition described herein.

In one aspect, the present disclosure provides a method of treating and/or preventing a fungal infection and/or formation of a fungal biofilm in a subject in need, the method comprising administering to the subject the composition described herein or the pharmaceutical composition described herein.

In one aspect, the present disclosure provides a method of treating and/or preventing a bacterial infection and/or formation of a bacterial biofilm in a subject in need thereof, the method comprising administering to the subject the composition described herein or the pharmaceutical composition described herein.

In embodiments, the method comprises administering the composition or pharmaceutical composition intravenously, topically, via wound irrigation (for example wound dressing or sterile solution), intradermally, intramucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, swish and swallow treatment, transmucosally, or transdermally.

In embodiments, the infection comprises *Candida albicans, Candida guilliermondii, Candida parapsilosis, Candida glabrata, Candida tropicalis, Candida dubliniensis, Staphylococcus aureus, Escherichia coli, Pseudomonas aeruginosa, Staphylococcus epidermidis*, or a combination of two or more thereof. In embodiments, the infection comprises *Candida albicans, Candida guilliermondii, Candida parapsilosis, Candida glabrata, Candida tropicalis, Candida dubliniensis*, or a combination of two or more thereof.

In embodiments, the method comprises topically administering the composition or pharmaceutical composition by irrigation. In embodiments, disrupting comprises contacting the composition or pharmaceutical composition with a biofilm in or on a catheter or in fluid communication with an animal or prior to attachment of the catheter for fluid communication in an animal.

Methods of Use

In one aspect, the disclosure provides compounds, salts thereof and compositions for disrupting bacterial or fungal biofilm. In one aspect, the disclosure provides compounds, salts thereof and composition for inhibiting the formation of bacterial or fungal biofilm.

In embodiments, the disclosure provides a method of inhibiting or disrupting biofilm, the method comprising contacting a surface with a composition, wherein the composition comprises a compound of formula (I) or (II).

In embodiments, a compound or salt of formula (I) or (II) or a pharmaceutical composition comprising a compound or salt of formula (I) or (II) are used to disrupt a biofilm or biofilms comprising one or a plurality of bacterial cells on the surfaces of a subject or a surface of an inanimate object, such as a laboratory bench, table top, implant (before or after implantation into a subject), or a catheter (before or after fluid communication with a subject is achieved). In embodiments, a compound or salt of formula (I) or (II) or a pharmaceutical composition comprising a compound or salt of formula (I) or (II) are used to disrupt a biofilm or biofilms comprising one or a plurality of fungal cells. In embodiments, a compound or salt of formula (I) or (II) or a pharmaceutical composition comprising a compound or salt of formula (I) or (II) are used to disrupt a biofilm or biofilms comprising one or a plurality of bacterial cells and/or one or a plurality of fungal cells. In embodiments, the disclosure relates to methods of treating or disputing biofilms derived from bacterial cells and fungal cells.

In embodiments, the surface is an indwelling medical device. In embodiments, the indwelling medical device is selected from the group consisting of a central venous catheter, a prosthetic heart valve, a urinary catheter, an artificial hip prosthesis, an artificial voice prosthesis, and an intrauterine device.

TABLE 1

Examples of indwelling medical devices and select organisms commonly found in these devices

| Indwelling Medical Device | Organisms |
|---|---|
| Central Venous Catheter | Coagulase-negative staphylocci, *Staphylococcus aureus*, *Enterococcus faecalis*, *Klebsiella pneumonia*, *Pseudomonas aeruginosa*, *Candida albicans* |
| Prosthetic Heart Valve | Viridans Streptococci, coagulase-negative staphylococci, enterococci, *Staphylococcus aureus* |
| Urinary Catheter | *Staphylococcus epidermidis*, *Escherichia coli*, *Klebsiella pneumoniae*, *Enterococcus faecalis*, *Proteus mirabilis* |
| Artificial Hip Prosthesis | Coagulase-negative staphylocci, β-hemolytic streptococci, enterococci, *Proteus mirabilis*, *Bacteriodes* species, *Staphylococcus aureus*, viridans *Streptococcus*, *Escherichia coli*, *Pseudomonas aeruginosa* |
| Artificial Voice Prosthesis | *Candida albicans*, *Streptococcus mitis*, *Streptococcus salivarius*, *Rothia dentrocariosa*, *Candida tropicalis*, *Streptococcus sobrinuss*, *Staphylococcus epidermidis*, *Stomatococcus mucilaginous* |
| Intrauterine Device | *Staphylococcus epidermidis*, *Corynebacterium* species, *Staphylococcus aureus*, *Micrococcus* species, *Lactobacillus plantarum*, group B streptococci, *Enterococcus* species, *Candida albicans* |

In embodiments, the disclosure provides compositions, pharmaceutical compositions or formulations disclosed herein for use in the prevention of bacterial and/or fungal biofilm formation. Also provided herein are the compositions, pharmaceutical compositions or formulations described herein for use in the treatment of a fungal infection or bacterial infection, and/or in the manufacture of a medicament for the treatment of a fungal infection and/or a bacterial infection. In embodiments, the composition comprises non-bonded beta-alanine, or a pharmaceutically acceptable salt thereof, at a weight to volume percent from about 0.1% to about 5.0%; non-bonded 2-aminoadipic acid, or a pharmaceutically acceptable salt thereof, at a weight to volume percent from about 0.1% to about 5.0%; non-bonded aspartic acid, or a pharmaceutically acceptable salt thereof, at a weight to volume percent from about 0.1% to about 5.0%; non-bonded cystathionine (0.2%), or a pharmaceutically acceptable salt thereof, at a weight to volume percent from about 0.1% to about 5.0%; non-bonded cysteine, or a pharmaceutically acceptable salt thereof, at a weight to volume percent from about 0.1% to about 5.0%; non-bonded ethanolamine, or a pharmaceutically acceptable salt thereof, at a weight to volume percent from about 0.1% to about 5.0%; non-bonded glutamic acid, or a pharmaceutically acceptable salt thereof, at a weight to volume percent from about 0.1% to about 5.0%, non-bonded homocysteine, or a pharmaceutically acceptable salt thereof, at a weight to volume percent from about 0.1% to about 5.0%; non-bonded hydroxyproline, or a pharmaceutically acceptable salt thereof, at a weight to volume percent from about 0.1% to about 5.0%; non-bonded phosphoethanolamine, or a pharmaceutically acceptable salt thereof, at a weight to volume percent from about 0.1% to about 5.0%; non-bonded phosphoserine, or a pharmaceutically acceptable salt thereof, at a weight to volume percent from about 0.1% to about 5.0%.

The disclosure also relates to the compositions, pharmaceutical compositions or formulations disclosed herein for use in treatment of a surface for disinfecting purposes. In embodiments, the surface is a surface of an implantable device or a catheter or drain tube.

The pharmaceutical compositions disclosed herein may also be used to decontaminate a surface, such as the surface of a biomedical device or an implant.

The pharmaceutical compositions disclosed herein may also further comprise or be administered with one or more active ingredients are chosen from anti-inflammatory agents, antimicrobial active agents, viral bacteriophages, antihistamines, anti-infectives, and nasal decongestants.

In embodiments, the anti-inflammatory agents are chosen from steroids and non-steroidal anti-inflammatories (NSAIDS). In embodiments, the steroids are chosen from prednisone, dexamethasone, and hydrocortisone. In embodiments, the steroids are corticosteroids chosen from prednisolone, prednisone, medrol, beclomethasone, budesonide, flunisolide, fluticasone and triamcinolone. In embodiments, the anti-inflammatory agents are corticosteroids chosen from dexamethasone, mometasone, and triamcinolone. In embodiments, the steroids are corticosteroids chosen from dexamethasone, mometasone, and triamcinolone. In embodiments, the NSAIDS are chosen from celecoxib, diclofenac, diflunisal, etodolac, fenoprofen, flurbirofen, ibuprofen, indomethacin, ketoprofen, ketorolac, mefenamic acid, meloxicam, nabumetone, naproxen, oxaprozin, piroxicam, sulindac, tolmetin, acetaminophen, or a newly designed NSAIDS.

In embodiments, the antimicrobial active agents are chosen from antibiotics, antifungals, and anti-virals. In embodiments, the antibiotics are chosen from penicillins, cephalosporins, quinolones, aminoglycosides, amphotericin B, etc.). In embodiments, the antibiotics such as penicillins, cephalosporins, macrolides, sulfonamides, quinolones, aminoglycosides, betalactam antibiotics, linezolid, vancomycin; aminoglycosides (including amikacin, gentamicin, kanamycin, neomycin, netilmicin, streptomycin, tobramycin, cephalosporins (including cefadroxil, cefazolin, cefalotin, cefalexin, cefaclor, cefoxitin, cefuroxime, cefixime, cefdinir, cefoperazone, cefotaxime, cefpodoxime, ceftazidime, ceftibuten, ceftriaxone, cefepime, loracarbef, ceftaroline cefobiprole) macrolides (including azithromycin, clarithromycin, erythromycin); penicillins (including amoxicillin, ampicillin, carbenicillin, cloxacillin, dicloxacillin, methicillin, mezlocillin, oxacillin, penicillin, piperacillin, ticarcillin); polypeptides (including bacitracin, colistin, polymyxin b), quinolones ciprofloxacin, levofloxacin, moxifloxacin, norfloxacin, ofloxacin, gatifloxacin, delafloxacin). sulfonamides (including sulfacetamide, sulfadiazine, sulfasalazine, sulfisoxazole, trimethoprim, trimethoprim-sulfamethoxazole); tetracyclines (including demeclocycline, doxycycline, minocycline, oxytetracycline, tetracycline, tigecycline) and others (including chloramphenicol, clindamycin, lincomycin, ethambutol, isoniazid, linezolid, metronidazole, mupirocin, nitrofurantoin, rifampicin, dapsone, imipenem/cilastatin), vancomycin, aztreonam), and all the above antibiotics in combination with efficacy enhancers such as avibactam, tazobactam and clavulanate.

In embodiments, the antibiotic is chosen from penicillins, cephalosporins, monobactams, carbapenems, macrolides, lincosamides, streptogramins, aminoglycosides, quinolones (fluoroquinolones), sulfonamides, and tetracyclines.

In embodiments, the penicillins are chosen from amoxicillin, ampicillin, bacampicillin, carbenicillin, cloxacillin, dicloxacillin-flucloxacillin, mezlocillin, nafcillin, oxacillin, penicillin G, penicillin V, piperacillin, pivampicillin, pivmecillinam, ticarcillin, and ticar.

In embodiments, the cephalosporins are chosen from cefacetrile (cephacetrile), cefadroxil (cefadroxyl), cefalexin (cephalexin), cefaloglycin (cephaloglycin), cefalonium (cephalonium), cefaloridine (cephaloradine), cefalotin (cephalothin), cefapirin (cephapirin), cefatrizine, cefazaflur, cefazedone, cefazolin (cephazolin), cefradine (cephradine), cefroxadine, and ceftezole. In embodiments, the cephalosporins are chosen from cefaclor, cefamandole, cefmetazole, cefonicid, cefotetan, cefoxitin, cefprozil (cefproxil), cefuroxime, and cefuzonam. In embodiments, the cephalosporins are chosen from cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, and ceftazidime. In embodiments, the cephalosporins are chosen from cefclidine, cefepime, cefluprenam, cefoselis, cefozopran, cefpirome, and cefquinome. In embodiments, the cephalosporins are chosen from ceftobiprole and ceftaroline. In embodiments, the cephalosporins are chosen from cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, cefuracetime, and ceftioxide. In embodiments, the monobactam is aztreonam.

In embodiments, the carbapenems are chosen from imipenem, imipenem/cilastatin, doripenem, meropenem, and ertapenem. In embodiments, the marcolides are chosen from azithromycin, erythromycin, clarithromycin, dirithromycin, roxithromycin, surlid, and telithromycin. In embodiments, the lincosamides are chosen from clindamycin and lincomycin. In embodiments, the streptogramins are chosen from pristinamycin and quinupristin/dalfopristin. In embodiments, the aminoglycosides are chosen from amikacin, gentamicin, kanamycin, neomycin, netilmicin, paromomycin, streptomycin, and tobramycin.

In embodiments, the quinolones are chosen from flumequine, nalidixic acid, oxolinic acid, piromidic acid, pipemidic acid, and rosoxacin. In embodiments, the quinolones are chosen from ciprofloxacin, enoxacin, lomefloxacin, nadifloxacin, norfloxacin, ofloxacin, pefloxacin, and rufloxacin. In embodiments, the quinolones are chosen from balofloxacin, gatifloxacin, grepafloxacin, levofloxacin, moxifloxacin, pazufloxacin, sparfloxacin, temafloxacin, and tosufloxacin. In embodiments, the quinolones are chosen from besifloxacin, clinafloxacin, gemifloxacin, sitafloxacin, trovafloxacin, and prulifloxacin.

In embodiments, the sulfonamides are chosen from sulfamethizole, sulfamethoxazole, sulfisoxazole, and trimethoprim-sulfamethoxazole. In embodiments, the tetracyclines are chosen from demeclocycline, doxycycline, minocycline, oxytetracycline, tetracycline, and tigecycline. In embodiments, the composition further comprises and efficacy enhancer and an antibiotic. In embodiments, the efficacy enhancer is chosen from avibactam, tazobactam and clavulanate.

In embodiments, the antifungals are chosen from imidazoles (such as miconazole, ketoconazole, clotrimazole, econazole, bifonazole, butoconazole, fenticonazole, isoconazole, oxiconazole, sertaconazole, sulconazole, tioconazole, and griseofulvin); triazoles (such as fluconazole, itraconazole, isavuconazole, ravuconazole, posaconazole, voriconazole, and terconazole); thiazoles (such as abafungin); allylamines (such as terbinafine, amorolfine, naftifine, and butenafine); echinocandins (such as echinocandins, anidulafungin, caspofungin, and micafungin); amphotericin B, and azole antifungals. In embodiments, the antifungal is amphotericin B or nystatin. In embodiments, the antifungal is terbinafine, aorolfine, or flucytosine. In embodiments, the antifungal is miconazole or ketoconazole. In embodiments, the antifungal is chosen from fluconazole, itraconazole, voriconazole, posaconazole, and ravuconazole. In embodiments, the antifungal is chosen from micafungin, caspofungin, and anidulafungin. In embodiments, the antifungal is griseofulvin.

In embodiments, the antivirals are chosen from anti-herpetic (antiherpesvirus) agents and anti-influenza agents. In embodiments, the anti-herpetic agents are chosen from acyclovir, brivudine, docosanol, famciclovir, idoxuridine, penciclovir, trifluridine, and valacyclovir. In embodiments, the anti-influenza agents are chosen from amantadine, rimantadine, oseltamivir, and zanamivir. In embodiments, the antivirals are chosen from acyclovir, famciclovir, penciclovir, valacyclovir, amantadine, rimantadine, oseltamivir, and zanamivir.

In one aspect, the disclosure provides a method of sterilizing an implant or biomedical device, optionally in fluid communication with a subject's circulatory system, the method comprising contacting a surface of the implant or a surface of the biomedical device with an effective amount of the composition described herein or the pharmaceutical composition described herein.

In embodiments, the biomedical device is a catheter or tube in fluid communication with the subject a subject's circulatory system. In one aspect, the disclosure provides a method of preventing formation of a biofilm and/or disrupting an existing biofilm on a surface, the method comprising contacting the surface with an effective amount of the composition described herein or the pharmaceutical composition described herein.

In embodiments, the composition further comprises glycerin at a weight to volume percentage of from about 0.1% to about 5.0%.

Drug-Containing Devices

In embodiments, the pharmaceutical composition comprising a compound or salt of Formula (I) or (II) is contained on within or embedded within a mucoadhesive polymer. Such polymers are chosen from protein based polymers, polysaccharides, polyesters, polyanhydrides, polyamides, phosphorous based polymers, acrylic polymers, vinylpyrrolidone polymers, celluloses, and silicones.

In embodiments, the mucoadhesive polymers have a mass average molecular weight above about 75,000 Da to about 20,000,000 Da. In embodiments, the average molecular weight ranges from about 100,000 to about 20,000,000 Da or from about 200,000 to about 1,000,000 Da or from about 400,000 to about 700,000 Da.

In embodiments, the mucoadhesive polymers include in general hydrophilic polymers and hydrogels. In the large classes of hydrophilic polymers, those containing carboxylic group exhibit mucoadhesive properties; these include polyvinyl pyrrolidone (PVP), methyl cellulose (MC), sodium carboxy-methylcellulose (SCMC) hydroxy-propyl cellulose (HPC) and other cellulose derivative. Hydrogels are the class of polymeric biomaterials that exhibit the basic characteristics of swelling by absorbing water, and then they interact with the mucus that covers epithelium by means of adhesion. Polymers with anionic groups include: carbopol, polyacrylates and their cross-linked modifications, polymers with cationic groups include chitosan and its derivatives and aminoethyl methacrylate or acrylate polymers.

One or more of the following basic properties of a polymer indicate a good mucoadhesive profile: high molecular weight, chain flexibility, high viscosity, optimal cross-linked density of polymer, charge and degree of ionization of polymer (anion>cation>unionized), medium pH, hydration of the polymer, high applied strength and duration of its application and high initial contact time. In addition to the above factors, some physiological factors, like mucin turnover and disease status also affect the mucoadhesion. The mucin turnover is expected to limit the residence time of the mucoadhesive agents on the mucus layer. This could detach mucoadhesives from the surface no matter how high the mucoadhesive strength may be.

In embodiments, the mucoadhesive system should possess an acceptable active ingredient loading capacity, good mucoadhesion, no irritancy, good feel in the place of administration, sustained drug delivery and an erodible formulation has the added advantage of not requiring retrieval after delivery of the dose. Therefore, hydrophilic polymers with good ability to stick to mucosal membranes are a good chose. They normally possess charged groups or nonionic functional groups capable of forming hydrogen bonds with mucosal surfaces. To accomplish these properties, structural characteristics such as strong hydrogen bonding groups (e.g. carboxyl, hydroxyl, amino- and sulfate groups), strong anionic or cationic charges, high molecular weight, chain flexibility, and surface energy properties favoring spreading onto mucus are sought.

In embodiments, anionic polymers have demonstrated mucoadhesive properties related to the ability of carboxylic groups to form hydrogen-bonds with oligosaccharide chains of mucins. In embodiments, weakly anionic carboxyl-containing polymers such as poly(acrylic acid), poly(methacrylic acid), sodium alginate, carboxymethylcellulose and poly(maleic acid)-co-(vinyl methyl ether) are used. In embodiments, chitosan and some synthetic polymethacrylates are cationic polymers that have mucoadhesiveness. This property has been related to their ability to interact with negatively charged mucins via electrostatic attraction and hydrophobic effects may also play a certain role. In embodiments, chitosan derivatives relevant to pharmaceutical applications include trimethyl chitosan, glycol chitosan, carboxymethyl chitosan and half-acetylated chitosan. In embodiments, solid micro/nanoparticulate systems based on chitosan and derivatives have been the focus of several studies.

In embodiments, compared to the charged, non-ionic polymers generally show lesser mucoadhesiveness. The specific interactions between mucin and these kind of polymers are usually very weak. In embodiments, amphoteric polymers such as gelatin and carboxymethyl chitosan, have been explored as mucoadhesive materials for pharmaceutical systems. In embodiments, their nature of and self-neutralization of cationic and anionic charges within their structure contribute to relatively lesser mucoadhesiveness, similar to non-ionic polymers. In embodiments, aminated derivative of gelatin has shown a considerable gastric mucoadhesion both in vitro and in vivo in rats.

In embodiments, polyampholyte polymers displayed particular characteristics that have to be taken into consideration with regarding to their mucoadhesive and penetration-enhancing properties. In embodiments, they exist positively charged, neutral and negatively charged, depending on dispersion pH and their specific isoelectric point. In embodiments, the viscosity in the dispersion is minimal and increases when pH is higher or smaller that isoelectric point.

In embodiments, the presence of inorganic salts affects the viscosity of the dispersion. In embodiments, the mucoadhesive and penetration enhancing properties of polyampholyte-based formulations are affected by pH-induced structural and physicochemical transformations.

In embodiments, there is another specific class of polymers called tiomers. They are characterized by containing side chains with thiol-bearing functional groups and are obtained by conjugating conventional mucoadhesive polymers with molecules carrying thiol functionality. The presence of this kind of functional groups enables the formation of disulfide bridges (covalent bonds) with cysteine rich sub-domains of mucus glycoproteins either via thiol/disulfide exchange reactions or through a simple oxidation of free thiol groups, exhibiting significantly enhanced mucoadhesive properties in comparison with conventional mucoadhesives. In embodiments, poly(acrylic acid)/cysteine, chitosan/N-acetylcysteine, alginate/cysteine, chitosan/thioglycolic acid and chitosan/thioethylamidine are typical polymeric thiomers. The development of novel derivatization approaches to thiolate non-ionic polymers may offer a way to improve their poor mucoadhesive performance. In embodiments, the polymers have acrylate end groups. They are a class of mucoadhesive polymers capable of forming covalent bonds with mucins similar to polymeric thiomers.

In embodiments, dendrimers have displayed usefulness as mucoadhesives due to their properties and unique structure. In embodiments, poly(amidoamine) (PAMAM) dendrimers carrying various functional groups (amino, carboxylate and hydroxyl surface groups, COOH) are chosen for mucoadhesiveness. In embodiments, boronic acid copolymers are chosen for mucoadhesiveness. In embodiments, copolymers of N-acryloyl-m-aminophenylboronic acid with N,N-dimethylacrylamide (e.g., up to 15 mol-% N-acryloyl-m-aminophenylboronic acid to ensure their solubility in aqueous environment) display interactions with stomach mucin and may facilitate the retention of poly(vinyl alcohol)/borax gels in mucosal lumens, mainly at pH 7.0-9.0, where their complexation with mucins is pronounced.

In embodiments, polymers containing sugar moieties as pendant groups (synthetic glycopolymers) possess hybrid properties. With this type of material it is possible to easily manipulate the architecture and physicochemical properties, which can be performed through homo- and copolymerization with monomers of different nature.

For example, glycopolymers have been obtained by free-radical copolymerization of N-(2-hydroxypropyl) methacrylamide with various sugar-containing monomers such as N-methacryloylglycylglycylglycylgalactosamine, N-methacryloylglycylglycylfucosylamine, N-methacryloylglycylglycylglucosamine, and N-methacryloylglycylglycylmannosamine. In embodiments, fucosylamine with copolymers are chosen, e.g., to adhere selectively to the colon in vitro, and stronger adhesion was observed for copolymers containing larger quantities of sugar moieties. The inventors hypothesized that this adhesion is related to the binding of sugar-moieties of the copolymers to specific receptors present in the colonic epithelium. The adhesion of these glycopolymers to the small intestinal mucosa was less pronounced and less sensitive to fucosamine in the copolymers.

In embodiments, considering the great number of polymers used for developing such systems, one is derived from polyacrylic acid, such as polycarbophil and carbomers; polymers derived from cellulose, such as hydroxyethylcellulose and carboxymethylcellulose; alginates, chitosan and derivatives, lectins and their derivatives are chosen.

In embodiments, the protein based polymers are chosen from collagens, albumins, and gelatins. In embodiments, the albumin is conjugated to poly-(ethylene glycol).

In embodiments, the polysaccharides are chosen from alginates, cyclodextrines, chitosans, dextrans, agarose, hyaluronic acid, starch, and cellulose. In embodiments, the polyesters are chosen from poly lactic acid (PLA), polyglycolic acid (PGA), poly lactide-co-glycolide (PLGA), polyhydroxybutyrate (PHB), poly(e-caprolactone), polydioxanone. In embodiments, the celluloses are chosen from carboxymethyl cellulose (CMC), methyl cellulose (MC), hydroxyethylcellulose (HEC), hydroxypropyl methyl cellulose (HPMC), hydroxylpropyl cellulose (HFC), ethyl hydroxy ethyl cellulose (EHEC), and methyl hydroxy ethyl cellulose (MHEC). In embodiments, the mucoadhesive polymer has one or more strong hydrogen bonding groups chosen from —OH and —COOH.

In embodiments, the mucoadhesive polymer is chosen from high molecular weight homo- and copolymers of acrylic acid crosslinked with a polyalkenyl polyether. In embodiments, the mucoadhesive polymer is chosen from crosslinked acrylic or methacrylic acid based polymers. For example, in embodiments, the mucoadhesive polymer is chosen from Carbopol or Carbomer brand polymers. For example, in embodiments, the mucoadhesive polymer is chosen from Carbopol® 934 Polymer, Carbopol® 940 Polymer, Carbopol® 941 Polymer, Carbopol® 980 Polymer, Carbopol® 981 Polymer, Carbopol® 1342 Polymer (Acrylates/C10-30 Alkyl Acrylate Crosspolymer), Carbopol® 1382 Polymer (Acrylates/C10-30 Alkyl Acrylate Crosspolymer), Carbopol® 2984 Polymer, Carbopol® 5984 Polymer, Carbopol® SC-200 Polymer (Acrylates/C10-30 Alkyl Acrylate Crosspolymer, and Carbopol® Silk 100 Polymer. In embodiments, the mucoadhesive polymer is Carbopol® 940 Polymer.

In embodiments, the mucoadhesive polymer is chosen from hydroxy propyl cellulose (HPC) or hydroxy propyl methyl cellulose (HPMC). In embodiments, the mucoadhesive polymer has an anionic charge.

Another strategy to adjust mucoadhesive properties of the system is to optimize their mechanical characteristics and modulate their swelling behavior or to improve their biocompatibility to use the polymer blends. New mucoadhesive blends may be obtained by mixture of pharmaceutical polymers in solid state or in solution. When two of these mucoadhesive materials are blended, their mucoadhesive properties are dependent on the strength of specific interactions occurring between both components upon hydration. When there is not the formation of insoluble polycomplexes, the specific interactions between the polymers are not very strong and the mucoadhesiveness of a system will often be intermediate between the adhesiveness of each individual component. Interpolymer complexes such as poly (carboxylic acids) and non-ionic polymers in solutions via hydrogen bonding results in formation of novel polymeric materials-interpolymer complexes. These materials can potentially be used for design of novel mucoadhesive dosage forms.

Methods for Preparing Compositions

The process steps in combining the various components of the compositions of the disclosure may be done so as to prevent degradation of individual ingredients and/or interactions between ingredients. Thus, after appropriately selecting the levels of amino acids to be employed in the formulation in order to avoid inherently incompatible flavors, highly pure forms of the amino acids are used. Recrystallizations of individual amino acids are carried out if necessary to ensure the absence of undesirable trace contaminants. After proper selection is made and adequate purity is obtained, close control of the process conditions is used to assure ultimate palatability.

In general, certain amino acids are not very water soluble. When such relatively insoluble members are used in the form of the hydrochloride salts and/or esters thereof, this may degrade their elemental forms. In order to promote the dissolution of the various amino acids in water, the water may be maintained at a temperature of about 90° C. to 100° C. However, in embodiments, some amino acids of the formulation are highly susceptible to thermal degradation so that to permit inclusion into the aqueous solution at such temperatures would reduce the efficacy of the liquid dosage form. In embodiments, the amino acid is glutamine. Particular carbohydrates from the group of monosaccharides, disaccharides, starches and dextrins, which may be suitably employed have various degrees of water solubility, and good solubility is desirable in formulating the dosage form.

The amino acid, aspartic acid, may have difficulty with solubility in water even at temperatures in the range of about 90° C. to 100° C. However, aspartic acid may be dissolved in alkaline water having a pH between about 8 and 14. Thus, the dissolution is facilitated by separately dissolving the aspartic acid in alkaline water having a pH of about 8 or above and then adding this pre-solution to the main solution. In some dosage forms, the pH of a liquid dosage form is from about a pH of 8 to about a pH of 10, but the aspartic acid or salt thereof is stored in alkaline conditions before addition to the solution.

Interactions fairly readily occur at elevated temperature between aldehyde or ketone groups present in the carbohydrate component, such as in glucose. In embodiments, the solution comprises glucose, (or potential aldehyde groups of a glucose-containing polymer subject to hydrolysis) and a compound of Formula (I) or (II), particularly lysine. Such interaction results in the formation of condensation products which are brown in color and which have a flavor resembling caramel. In embodiments methods of making the liquid dosage forms comprise steps taken to minimize the extent of the time-temperature integral over which amino acids and such carbohydrates are both present in the solution in order to thereby minimize the extent of caramelization that may occur. This result is achieved most expeditiously by adding the carbohydrate sufficiently rapidly while agitating the solution to enhance its dissolution. In this respect, the addition of the carbohydrate components, such as glucose, should be sufficiently rapid to drop the temperature to about 40° C. within ten minutes time from the initial addition. It should also be understood that not only does rapid dissolution avoid unpalatability resulting from the interaction between amino acids and the aldehyde or ketone groups of the carbohydrate, but it reduces the time at which the methionine is exposed to the relatively high temperatures. Generally, not all of the carbohydrate is added at this time, although it all could be added at this time if one would so desired, and the remainder is dissolved subsequently in the process.

Although it is considered that the stated formulation has advantages from a cost standpoint and from case of formulation, various minerals may be provided as part of the dosage form in a percentage or trace levels within the solution. Magnesium, for instance, might be provided in the form of acetate, citrate or chloride in embodiments. Similarly, potassium might be provided in the form of bicarbonate or sorbate. Likewise, iron might be provided in the form of chloride, gluconate, acetate or citrate. Calcium may be supplied as acetate, citrate or bicarbonate. Iodine may be provided as the iodide of sodium, magnesium or manganese. Manganese might be provided as manganous chloride, and zinc could be provided as the acetate. Still other suitable forms may also be used.

In embodiments, addition to the foregoing minerals, if it is intended to employ the oral or topical dosage form for extended periods of time, metabolizable and nontoxic salts of cobalt and molybdenum are also included. Examples of such suitable salts include sodium, potassium, and ammonium molybdate and cobaltous acetate-$4H_2O$.

The order of addition of these minerals is important in order to avoid potential interactions which might result in precipitates that will adversely affect the solution. Magnesium oxide, which is utilized as the source of magnesium, is readily incorporated into the main solution of essential and non-essential amino acids plus carbohydrate by first being dissolved in an aqueous solution of potassium hydroxide and glucono-delta-lactone to form a pre-solution. The pre-solution in which the magnesium oxide is completely dissolved is slowly added to the main solution.

In embodiments, hydrated sodium glycerophosphate is added to the solution, as is hydrated ferrous ammonium sulfate. The sodium chloride may also be conveniently added at this time. Following the dissolution of the glycerophosphate and the ferrous compounds, the remainder of the carbohydrate is dissolved in the solution, using constant stirring. The temperature of the solution may be raised slightly in order to expedite the solution of the carbohydrate but the temperature should not exceed 35° C.

At this point which is approaching the end of the dissolution process, the water-soluble vitamins are added, one after another, insuring that each is dissolved before the following one is added. Adding the vitamins earlier and/or while the temperature is higher, is avoided because of the thermal susceptibility of these vitamins, particularly thiamine, for example.

The hydrated calcium chloride is added after the dissolution of the remainder of the carbohydrate. It is extremely important that all of the glycerophosphate compound be completely in solution before the addition of the calcium chloride, and moreover, the addition of the calcium should not immediately follow addition of the glycerophosphate compound because of the potential formation of a refractory precipitate of calcium glycerophosphate. It has been found that such formation of a refractory precipitate is completely avoided if the remainder of the carbohydrate, and preferably also the vitamins, are dissolved in the solution between the initial addition of the glycerophosphate compound and the subsequent dissolution of the soluble calcium compound. It is believed that the glycerophosphate is complexed in some manner by the other ions after a sufficient residence in solution.

In embodiments, the composition comprising a compound or salt of Formula (I) or (II) comprises trace amounts of minerals, which can be dissolved in water, and these solutions combined to form one pre-solution. In some methods of making the compositions in solution format, this pre-solution includes the manganous salt, the cupric salt, the zinc salt and the iodide salt, plus the molybdenum and the cobalt salts if such are employed. At this point in the process, the temperature of the main solution is maintained at about 30° C. or below while the pre-solution of the trace minerals is slowly added. Particularly important is the handling of the manganous salt. It has been found that the manganous salt should not be added to the solution prior to the complete dissolution of the water-soluble iron compound, for it appears that a stable solution is not obtained if these two salts are added in the reverse order to a solution containing the amino acids and carbohydrates. It is believed that addition in the reverse order may cause oxidation of the manganous ion to manganese dioxide accompanied by the formation of undesirable precipitates. It is thought that the other ingredients in the solution may well form stable complexes with the ferrous iron if it is added sufficiently prior to the addition of 'the manganous iron, and accordingly the ferrous ion should preferably be dissolved in the solution prior to the second addition of carbohydrate.

Another consideration in making a composition of this type is that the growth of microorganisms, such as bacteria should be prevented. In embodiments, the solution or liquid dosage form comprises an antibiotic. In embodiments, the hypertonicity of the solution is controlled such that from the time the temperature is lowered by the first dissolution of the carbohydrate, the amount of water present in the solution, relative to the amount of carbohydrate and solutes, is regulated so that the solution is hypertonic. For purposes of embodiments, hypertonic solution is defined as having an osmotic pressure higher than that within microorganisms so that undesirable microorganisms, for example, *Escherichia coli*, cannot grow in the solution. The amounts of water added subsequently throughout the process are similarly balanced with the amounts of additional solute so that the hypertonicity of the solution is maintained, at least up to and through the addition of all the water-soluble ingredients.

In embodiments, the compound or salt of Formula (I) or (II) comprise a modification on their side chain or N or C terminus. Modification such as a thiol modification, for instance, can be performed by a reaction of introducing a protected or non-protected thiol group at the β carbon atom of the amino acid derivative is not particularly limited as long as it is a reaction that introduces a protected or non-protected thiol group at the β carbon atom of the amino acid derivative. Introduction may also be carried out after introducing a leaving group at the β carbon atom of the amino acid derivative as an exchange reaction with the leaving group.

For example, this reaction can be carried out by reacting the amino acid derivative with a thiol compound. In terms of introducing a protected thiol group, it is preferred to employ a thiol compound having a protecting group and a hydrogen atom bound to the sulfur atom. Thiol compounds can include benzyl mercaptans or tritylthiols that may possess any number of substituents such as a halogen atom such as fluorine, chlorine, bromine, and iodine, an lower alkyl group having 1-4 carbons such as a methyl group and an ethyl group, an alkoxy group having 1-4 carbons such as a methoxy group and an ethoxy group, and a nitro group at any position on the phenyl ring, alkanethiols such as methanethiol, ethanethiol, and t-butanethiol, acyl thiols that can be easily converted into an acetamidomethyl group, a trityl group, and a disulfide group, and the like.

The amount of the thiol compound used may be 1-100 equivalents, preferably 2-20 equivalents, and further preferably 3-10 equivalents to 1 equivalent of the amino acid derivative to be the raw material. Examples of the solvent used can include THF, DCM, DMSO, DMF, and the like, and among these DMF is preferred. The reaction can be carried out in a reaction condition of e.g. at 1-100° C., preferably 10-80° C., and further preferably 15-35° C., for example 30 minutes-24 hours or 3.5 hours-5 hours.

The raw material compound of this reaction may be a compound or salt of Formula (I) or (II) that can have a thiol group introduced at the β-position. In other words, the raw material compound may be a compound or salt of Formula (I) or (II) having the amino group, carboxyl group, side chain substituent, and the like of the amino acid protected or substituted by a substituent. In one aspect, in terms of efficiently carrying out the reaction, it is preferably an amino acid derivative possessing a leaving group at the β-position, and more preferably an amino acid derivative possessing a halogen atom at the β-position. Moreover, in one aspect, in terms of preventing side reactions to increase the yield, it is preferably an amino acid derivative having the amino group and carboxyl group of the amino acid protected.

The reaction of converting the amino group or carboxyl group bound to the α carbon atom of an amino acid derivative into a substituent to be the substrate for a hydrolase selective for D- or L-amino acids is not particularly limited as long as it is a reaction that yields an amino acid derivative having a substituent to be the substrate for a hydrolase selective for D- or L-amino acids bound to the α carbon atom after the reaction. "The amino group or carboxyl group bound to the α carbon atom of an amino acid derivative" in the starting material of the reaction may be a protected or non-protected amino group or carboxyl group. In other words, it may be an unprotected free amino group or carboxyl group, or it may be an amino group or carboxyl group protected by a protecting group. In one aspect, when carrying out this reaction after introducing a thiol group at the β-position of the amino acid derivative, if an amino acid derivative having a thiol group introduced at the β-position is used as the raw material and the amino group and carboxyl group are protected for thiolation, the reaction can be carried out using an amino acid derivative having these protected as the raw material.

A group that can be generally employed as the protecting group of the amino group can be employed as the protecting group of the amino group, and e.g. a lipophilic protecting group described below etc. can be employed. For example, in one aspect, examples can include a protecting group such as a 9-fluorenylmethoxycarbonyl (Fmoc) group or a t-butyloxycarbonyl (Boc) group, a carbonate-containing group such as an allyloxy carbonate (Alloc) group, an acyl group such as an acetyl (Ac) group, an aryl group, a benzyl group, and the like. In order to introduce a protecting group, e.g. when introducing a Boc group, this can be carried out by e.g. a method of adding a THF solution of Boc2O to the reaction system. The introduction of the protecting group of the amino group can be carried out with the above method as well as well-known methods according to the protecting group. Moreover, the deprotection of the protecting group of the amino group can be carried out by treatment with an acid or a base. For example, when the protecting group is a Boc group, an acid such as trifluoroacetic acid (TFA) can be used. In doing so, this is preferably carried out in the presence of a solvent, examples of which can include DCM, THF, acetonitrile, and the like. The deprotection of the protecting group of the amino group can be carried out with the above method as well as ordinary methods.

A group that can be generally employed as the protecting group of the carboxyl group can be employed as the protecting group of the carboxyl group, for example a lipophilic protecting group described below etc. can be employed. For example, in one aspect, examples include protection as an ester by an alkyl group such as a methyl group, an ethyl group, and a tert-butyl group, or an arylalkyl group such as a benzyl group. When the protecting group of the carboxyl group is a methyl group, methyl esterification can be carried out e.g. by a method of adding thionyl chloride and methanol. The introduction of the protecting group of the carboxyl group can be carried out depending on the protecting group. Moreover, the deprotection of the protecting group of the carboxyl group can be carried out by treatment with an acid or a base. For example, when the protecting group is a methyl group, a base such as sodium hydroxide can be used.

In doing so, this is preferably carried out in the presence of a solvent, examples of which can include THF, dioxane, acetonitrile, and the like. The deprotection of the protecting group of the carboxyl group can be carried out with the above method as well as ordinary methods.

EXAMPLES

Example 1

The Effect of Nutritious Compositions Comprising Amino Acids on Biofilm

Three intravenous solutions were tested for their effect on biofilm formation. These solutions are supplements provided to patients in hospitals, and are a mixture of amino acids, ranging from 3% to 10%, in sterile water (Table 2). In Table 2, all amino acids are the L-isomer, and the concentration listed indicates the concentration of amino acid in the undiluted IV Solution.

TABLE 2

Composition of three IV solutions used in study

| | Procalamine ® (3%)* | Aminosyn II ® (10%)* | FreAmine III ® (10%)* |
|---|---|---|---|
| | 100 ml | 100 ml | 100 ml |
| Isoleucine | 0.21 g | 0.66 g | 0.69 g |
| Leucine | 0.27 g | 1.0 g | 0.91 g |
| Lysine | 0.22 g | 1.05 g | 0.73 g |
| Methionine | 0.16 g | 0.172 g | 0.53 g |
| Phenylalanine | 0.17 g | 0.298 g | 0.56 g |
| Threonine | 0.12 | 0.4 g | 0.40 g |
| Tryptophan | 0.046 | 0.2 g | 0.15 g |
| Valine | 0.2 | 0.5 g | 0.66 g |
| Alanine | 0.21 g | 0.993 g | 0.71 g |
| Glycine | 0.42 | 0.5 g | 1.40 g |
| Arginine | 0.29 | 1.018 g | 0.95 g |
| Histidine | 0.085 | 0.30 g | 0.28 g |
| Proline | 0.34 g | 0.722 g | 1.12 g |
| Serine | 0.18 g | 0.53 g | 0.59 g |
| Cysteine | <0.014 g | | <0.016 g |
| L-Aspartic Acid | | 0.7 g | |
| L-Glutamic Acid | | 0.738 g | |
| N-Acetyl-L-Tyrosine | | 0.27 g | |
| Sodium Acetate | 0.20 g | | |
| Magnesium Acetate | 0.054 g | | |
| Calcium Acetate | 0.026 g | | |
| Socium Chloride USP | 0.12 g | | |
| Potassium Chloride USP | 0.15 g | | 0.12 g |
| Phosphoric Acid NF | 0.041 g | | |
| Potassium Metabisulfite NF | <0.05 g | | |
| Sodium Bisulfite | | | <0.10 g |

In vitro biofilm formation was tested using two assays, sustained inhibition and disruption. Both assays assess biofilm formed on polystyrene plates. The first, tests the effects of amino acid solution on a developing biofilm, while the latter tests the effects of the solution on a pre-formed mature biofilm, both compared to media without supplemented amino acids. Results showed that all three solutions reduced biofilm formation in *C. albicans* and MRSA, by varying degrees (Table 3A and Table 3B).

TABLE 3A

Effects of intravenous solutions on *C. albicans* and *S. aureus* biofilms using in vitro sustained inhibition assays

| | Biofilm sustained inhibition | | | |
|---|---|---|---|---|
| | *C. albicans* | | *S. aureus* | |
| | Normalized | p-value | Normalized | p-value |
| Media | 1 ± 0.062 | | 1 ± 0.067 | |
| 1% Procalamine | 0.94 ± 0.044 | 0.01 | 0.51 ± 0.035 | 7.86E−04 |
| 1% Aminosyn | 0.99 ± 0.076 | 0.39 | 0.66 ± 0.029 | 2.56E−04 |
| 1% FreAmine | 0.92 ± 0.082 | 0.01 | 0.57 ± 0.036 | 2.15E−05 |
| 3% Aminosyn | 0.80 ± 0.041 | 2.44E−07 | 1.20 ± 0.081 | 4.30E−06 |
| 3% FreAmine | 0.72 ± 0.062 | 4.95E−10 | 0.59 ± 0.057 | 5.21E−05 |

TABLE 3B

Effects of intravenous solutions on *C. albicans* and *S. aureus* biofilms using in vitro sustained disruption assays

| | Biofilm Disruption | | | |
|---|---|---|---|---|
| | *C. albicans* | | *S. aureus* | |
| | Normalized | p-value | Normalized | p-value |
| Media | 1 ± 0.074 | | 1 ± 0.068 | |
| 1% Procalamine | 0.79 ± 0.072 | 8.44E−07 | 0.64 ± 0.032 | 1.88E−04 |
| 1% Aminosyn | 0.88 ± 0.047 | 0.02 | 0.78 ± 0.034 | 4.80E−04 |
| 1% FreAmine | 0.75 ± 0.042 | 6.00E−05 | 0.86 ± 0.047 | 2.13E−03 |
| 3% Aminosyn | 0.81 ± 0.057 | 2.49E−04 | 0.95 ± 0.062 | 0.04 |
| 3% FreAmine | 0.75 ± 0.045 | 6.62E−09 | 0.51 ± 0.077 | 2.49E−04 |

FreAmine® decreased biofilm formation in *C. albicans* by almost 30% and Procalamine® resulted in a 50% decrease in MRSA biofilms, both compared with media not supplemented with amino acids. However, in order to test these intravenous solutions in an in vitro assay, the commercially available solutions were diluted in cell culture media and thus test concentrations were 1% and 3% of what is normally administered to patients. While these lower concentrations reduced biofilm formation, further testing of all L-amino acids (individually and in combination) were conducted to determine their individual effect on biofilms.

Example 2

Determining the Inhibition or Disruption of Biofilm Using Compositions Comprising an Amino Acid In animal species other than *Homo sapiens*, amino acids may be present in their blood other than the 34 that were examined. These different amino acids would be examined for effect on bacterial and fungal biofilm, then used in a species specific way and could be used on instruments and surfaces to combat bacterial and fungal organisms that produce biofilm.

Other amino acids in the blood of animals could combat bacterial and fungal biofilm and therefore may be useful in treating these bacterial and fungal infections that would lie on the external surfaces of infected animals such as humans and could also be used to combat these pathogens on instruments and surfaces that need to be treated. Two types of biofilm assays were performed: a sustained inhibition assay and a disruption assay. The sustained inhibition assay assessed the compound's ability to prevent biofilm development throughout all stages of biofilm formation, while the disruption assay assessed the compound's ability to break up an existing mature biofilm.

For fungal biofilm assays, all solutions were prepared in RPMI 1640 medium. All bacterial biofilm solutions were prepared in Tryptic Soy Broth (TSB), supplemented with 1% glucose (henceforth referred to as TSB-G). All subsequent procedures were performed in a manner that maintained sterility. A solution of each amino acid to be tested was prepared in weight to volume concentrations ranging from 0.1-5.0%. Amino acids were also tested in combinations. Compound solutions were homogenized with gentle agitation in the dark (4° C., 24 hours) before use.

Thirty-four amino acids that occur freely in human blood were tested as follows: L-alanine, Beta-alanine, 2-aminoadipic acid, 2-aminobutyric acid, L-arginine, L-asparagine, L-aspartic acid, L-citrulline, L-cysteine, ethanolamine, L-glutamic acid, L-glycine, L-glutamine, L-histidine, 3-methyl-L-histidine, L-homocysteine L-isoleucine, L-leucine, L-lysine, L-methionine, L-omithine, L-phenylalanine, O-phosphoethanolamine, L-proline, Trans-4-hydroxy-L-proline, L-serine, O-phospho-L-serine, L-taurine, L-threonine, L-tryptophan, L-tyrosine, and L-valine. Two amino acids (1-methyl-L-histidine and L-cystathionine) were prepared at a highest concentration of 0.2% due to their limited solubility in the culture media. All biofilm assays were performed using 384-well non-tissue culture treated polystyrene plates. The fungal species tested are as follows: *Candida albicans*, *Candida guilliermondii*, *Candida parapsilosis*, *Candida glabrata*, *Candida tropicalis*, *Candida dubliniensis*, and *Candida auris*. The bacterial species tested are as follows: *Staphylococcus aureus* (standard wild type and methicillin-resistant strain USA300), *Escherichia coli*, *Pseudomonas aeruginosa* and *Staphylococcus epidermidis*.

Fungal strains were streaked on Yeast Peptone Dextrose (YPD) agar plates and incubated at 30° C. for 48 hours. A single colony from each strain to be tested was inoculated into YPD broth and grown for 12 hours, at 30° C., shaking at 225 rpm. For the fungal biofilm inhibition assay, 1 µl of saturated overnight cell culture was added to either 80 µL of RPMI-1640 or RPMI-1640 supplemented with the amino acid compound solution to be tested, in a 384-well plate. The cells were allowed to adhere to the plate for 90 minutes at 37° C. shaking at 350 rpm. Loosely bound cells were washed once with phosphate buffered saline (PBS) and 80 µl of RPMI-1640, or RPMI-1640 supplemented with the amino acid compound solution was added to the plate. The plate was further incubated for 24 hours at 37° C. shaking at 350 rpm. Media was carefully aspirated and the biofilm was measured by optical density at 600 nm. Twelve replicates were performed for each tested condition and the reported values are normalized to the control (RPMI-1640 media only). For the fungal biofilm disruption assays, 80 µL of RPMI-1640 was added to the plate, along with 1 µL of overnight cell culture. The cells were allowed to adhere to the plate for 90 minutes at 37° C. shaking at 350 rpm. Loosely bound cells were washed once with PBS and 80 µL of RPMI-1640 was added to the plate. The plate was further incubated for 24 hours at 37° C. shaking at 350 rpm. Media was carefully aspirated from the mature biofilm and 80 µL of RPMI-1640, or RPMI-1640 supplemented with the amino acid compound solution to be tested, was gently added to the plate. The plate was further incubated for 24 hours at 37° C. shaking at 350 rpm. Media was carefully aspirated and the biofilm was measured by optical density at 600 nm. Twelve replicates were performed for each tested condition and the reported values are normalized to the control (RPMI-1640 media only).

Bacterial strains were streaked on Blood Agar plates (5% sheep blood in Tryptic Soy Agar) and incubated at 37° C. for 24 hours. A single colony from each strain to be tested was inoculated in a TSB broth and grown for 12 hours, at 37° C. shaking at 225 rpm. For the bacterial biofilm inhibition assays, 1 µL of saturated overnight cell culture was added to either 80 µL of TSB-G, or TSB-G supplemented with the amino acid compound solution to be tested, in a 384-well plate. The cells were allowed to adhere to the plate for 60 minutes at 37° C. without shaking. The media was carefully aspirated and 80 µL of TSB-G, or TSB-G supplemented with the amino acid compound solution was added to the plate. The plate was further incubated for 24 hours at 37° C. without shaking. Media was carefully aspirated and the biofilm was measured by optical density at 600 nm. Eight or twelve replicates were performed for each tested condition and the reported values are normalized to the control (TSB-G media only). For the bacterial biofilm disruption assays, 80 µL of TSB-G was added to the plate, along with 1 µL of overnight cell culture. The cells were allowed to adhere to the plate for 60 minutes at 37° C. with no shaking. The media was carefully aspirated and 80 µL of TSB-G was added to the plate. The plate was further incubated for 24 hours at 37° C. with no shaking. Media was carefully aspirated from the mature biofilm and 80 µL of TSB-G, or TSB-G supplemented with the amino acid to be tested, was gently added to the plate. The plate was further incubated for 24 hours at 37° C. without shaking. Media was aspirated and the biofilm was measured by optical density at 600 nm. Twelve replicates were performed for each tested condition and the reported values are normalized to the control (TSB-G media only).

Based on the reduction seen in the presence of intravenous amino acid solution mixture, it was hypothesized that one or a combination of amino acids could be effective in inhibiting and disrupting both *C. albicans* and MRSA biofilms. To determine which amino acids reduce biofilm formation, 34 L-amino acids were selected including 20 L-amino acids and their derivatives commonly found in human blood for further experiments. Each amino acid was tested individually, at differing concentrations (0.2%-5%, based on solubility), for their ability to both inhibit and disrupt *C. albicans* and MRSA biofilms.

Table 4 summarizes the results of the inhibition assay, which assessed each amino acid's ability to prevent biofilm development, promote biofilm growth, and neutral effects on bacteria (*S. aureus*) biofilm formation and fungal (*C. albicans*) biofilm formation at 1% amino acid concentrations (unless specifically noted); $p<0.001$.

TABLE 4

Results of sustained inhibition biofilm assay

| Table 4 | Reduce B Biofilm | Reduce F Biofilm | Promote B Biofilm | Promote F Biofilm | Reduce Both | Promotes Both | Neutral |
|---|---|---|---|---|---|---|---|
| Alanine | | | | | | | ● |
| Beta-Alanine | ● | | | | | | |
| 2 Aminoadipic Acid | ● | | | | | | |
| 2 Aminobutyric Acid | | | | | | | ● |
| Arginine | | | | ● | | | |
| Asparagine | | | | ● | | | |
| Aspartic Acid | ●● | ●● | | | ●● | | |
| Citrulline | | | | ● | | | |
| Cystathionine (0.2%) | | | | | | | ● |
| Cysteine | ●● | ●● | | | ●● | | |
| Ethanolamine | | ● | | | | | |
| Glutamine | | | | | | | ● |
| Glutamic Acid | ●● | ●● | | ● | ●● | | |
| Glycine | | | | ● | | | |
| Histidine | | | | | | | ● |
| Homocysteine (0.4%) | | ● | | | | | |
| Hydroxyproline | ● | | | | | | |
| Isoleucine | | | | | | | ● |
| Leucine | | | | ● | | | |
| Lysine | | | | ● | | | |
| Methionine | | | | ● | | | |
| 1-Methylhistidine | | | | | | | ● |
| 3-Methylhistidine | | | | ● | | | |
| Phenylalanine | | | | ● | | | |
| Ornithine | | | | ● | | | |
| Phosphoethanolamine | ● | | | | | | |
| Phosphoserine | | | | | | | ● |
| Proline | | | | | | | ● |
| Serine | | | | ● | | | |
| Taurine | | | | ● | | | |
| Threonine | | | | ● | | | |
| Tryptophan | | | | | | | ● |
| Tyrosine | | | | | | | ● |
| Valine | | | | ● | | | |

In Table 4, a single dot [i.e. ●] signifies minor effect (from about 10 to about 30% change), two dots [i.e. ●●] signifies major effect (greater than about 30% change). B Biofilm=Bacterial Biofilm. F Biofilm=Fungal Biofilm. Neutral=No effect on the biofilm Table 5 summarizes the results of the disruption assay, which assessed each amino acid's ability to break up (disrupt) an existing mature biofilm, promote biofilm growth, and neutral effects on bacteria (*S. aureus*) biofilm formation and fungal (*C. albicans*) biofilm formation at 1% amino acid concentrations (unless specifically noted); p<0.001.

amino acids promoted *C. albicans* biofilms, compared with media not supplemented with additional amino acids (Tables 4 and 5).

The following additional amino acids (in addition to L-cysteine, L-glutamic acid, and L-aspartic acid) also have anti-biofilm properties against fungal biofilms when administered individually in at least one of the two biofilm assays tested (sustained inhibition and/or disruption), but the effects are minimal (reduction by less than two-fold): Ethanolamine; L-homocysteine; Phosphoserine; L-proline.

TABLE 5

Results of disruption biofilm assay

| Table 5 | Reduce B Biofilm | Reduce F Biofilm | Promote B Biofilm | Promote F Biofilm | Reduce Both | Promotes Both | Neutral |
|---|---|---|---|---|---|---|---|
| Alanine | | | ● | | | | |
| Beta-Alanine | | | | | | | ● |
| 2 Aminoadipic Acid | ● | | | | | | |
| 2 Aminobutyric Acid | | | | | | | ● |
| Arginine | | | ● | | | | |
| Asparagine | | | | | | | ● |
| Aspartic Acid | ●● | ●● | | | ●● | | |
| Citrulline | | | ● | | | | |
| Cystathionine (0.2%) | ● | | | | | | |
| Cysteine | ●● | ●● | | | ●● | | |
| Ethanolamine | | | | | | | ● |
| Glutamine | | | | | | | ● |
| Glutamic Acid | ●● | ●● | ● | | ● | | |
| Glycine | | | ● | | | | |
| Histidine | | | | | | | ● |
| Homocysteine (0.4%) | | ● | | | | | |
| Hydroxyproline | ● | | | | | | |
| Isoleucine | | | ● | | | | |
| Leucine | | | ● | | | | |
| Lysine | | | ● | | | | |
| Methionine | | | | | | | ● |
| 1-Methylhistidine | | | | | | | ● |
| 3-Methylhistidine | ● | | | | | | |
| Phenylalanine | | | ● | | | | |
| Ornithine | | | ● | | | | |
| Phosphoethanolamine | ● | | | | | | |
| Phosphoserine | ● | ● | | | | | |
| Proline | | ● | ● | | | | |
| Serine | | | ● | | | | |
| Taurine | | | ● | | | | |
| Threonine | | | | | | | ● |
| Tryptophan | | | | | | | ● |
| Tyrosine | | | | | | | ● |
| Valine | ● | | | | | | |

In Table 5, a single dot [i.e. ●] signifies minor effect (from about 10 to about 30% change), two dots [i.e. ●●] signifies major effect (greater than about 30% change). B Biofilm=Bacterial Biofilm. F Biofilm=Fungal Biofilm. Neutral=No effect on the biofilm.

Results show that 7 amino acids inhibited MRSA biofilms while 5 amino acids inhibited *C. albicans* biofilms to varying degrees (Table 4). We also found 10 amino acids disrupted MRSA biofilms while 6 amino acids disrupted *C. albicans* biofilms (Table 5). There were 6 amino acids, aminoadipic acid, aspartic acid, cysteine, glutamic acid, hydroxyproline and phosphoethanolamine, that both inhibited and disrupted MRSA biofilms (Tables 4 and 5). In contrast, *C. albicans* biofilms were both inhibited and disrupted by 4 amino acids, aspartic acid, cysteine, glutamic acid and homocysteine (Tables 4 and 5). Only 3 amino acids, cysteine, aspartic acid and glutamic acid both inhibit and disrupt *Candida* and *Staphylococcus* biofilms (Tables 4 and 5).

Additionally, we found 12 amino acids that promoted MRSA biofilms, in inhibition and/or disruption assays and 2

Unlike the optimal combination solution of 0.5% L-cysteine+0.5% L-glutamic acid+0.5% L-aspartic acid solution described below, when Ethanolamine, L-homocysteine, Phosphoserine, and L-proline are tested in combination at concentrations ranging from about 0.1 to about 5.0% weight to volume, there is no increase in effectiveness against biofilms (biofilm reduction remains at less than twofold).

The following additional amino acids (in addition to L-cysteine, L-glutamic acid, and L-aspartic acid) also have anti-biofilm properties against bacterial biofilms when administered individually at concentrations ranging from about 0.1 to about 5.0% weight to volume in at least one of the two biofilm assays tested (sustained inhibition and/or disruption), but the effects are minimal (reduction by less than twofold): Beta-alanine; 2-aminoadipic acid; Hydroxy-L-proline; O-phosphoethanolamine.

It was also discovered that certain amino acids support (improve) biofilm growth and therefore are not recommended to be administered to patients at risk of infection. The amino acids that support (improve) fungal biofilm growth in at least one of the two biofilm assays tested (sustained inhibition and/or disruption) are as follows: 3-methyl-L-histidine; L-valine.

The amino acids that support (improve) bacterial biofilm growth in at least one of the two biofilm assays tested (sustained inhibition and/or disruption) are as follows: L-alanine; L-arginine; L-asparagine; L-citrulline; L-glycine; L-isoleucine; L-leucine; L-lysine; L-methionine, L-phenylalanine; L-omithine; L-proline; L-serine; L-taurine; L-threonine.

The following amino acids are neutral (i.e. they have no effects on bacterial or fungal biofilms) in both assays (sustained inhibition and disruption): 2-aminobutyric acid; L-glutamine; L-histidine; 1-methyl-histidine; L-tyrosine; L-tryptophan.

Example 3

Figure 1B:
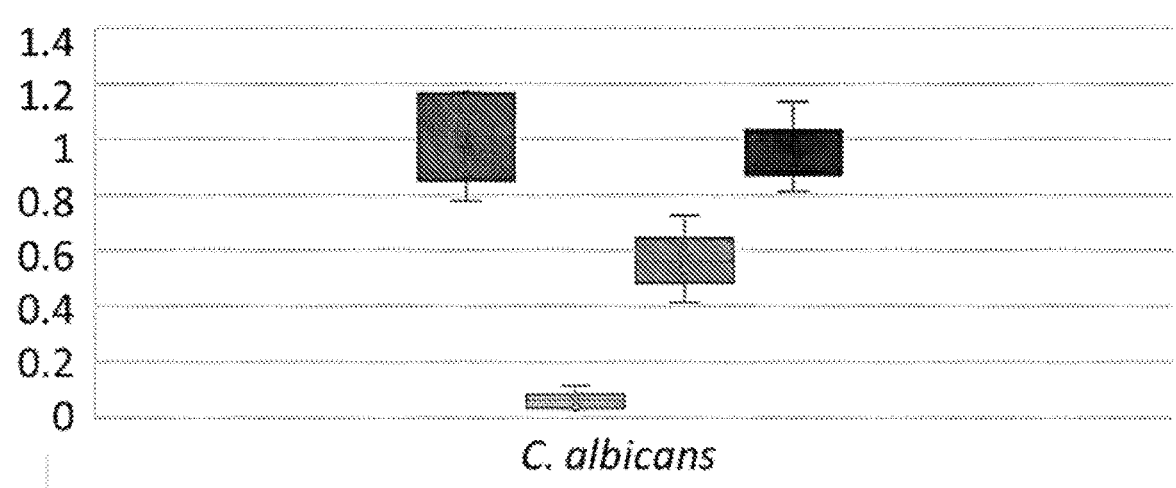

Determining the Inhibition or Disruption of Biofilm Using Compositions Comprising Amino Acids Three amino acids were found to have reduced both *C. albicans* and MRSA biofilms, so a composite solution of the three amino acids, cysteine, aspartic acid and glutamic acid was subjected to further experiments. Different concentrations (0.75-3%) were tested and it was found that a 1.5% solution i.e. 0.5% cysteine+0.5% aspartic acid+0.5% glutamic acid, worked best against both *C. albicans* and MRSA biofilms, using both inhibition and disruption assays, mentioned earlier (FIG. 1A-1D). The combined 1.5% amino acid solution was highly effective, resulting in an 85-90% reduction in biofilms (FIG. 1A-1D). While this solution is most effective at 1.5%, it is also effective (~50% reduction) against *C. albicans* biofilms at 0.75% (0.25% L-cysteine+ 0.25% L-aspartic acid+0.25% L-glutamic acid) and against *S. aureus* biofilms at 0.375% (0.125% L-cysteine+0.125% L-aspartic acid+0.125% L-glutamic acid) (FIGS. 1A and 1B).

Example 4

Compositions of the Disclosure in a Microfluidic Flow Device Biofilm Model

Figure 2:
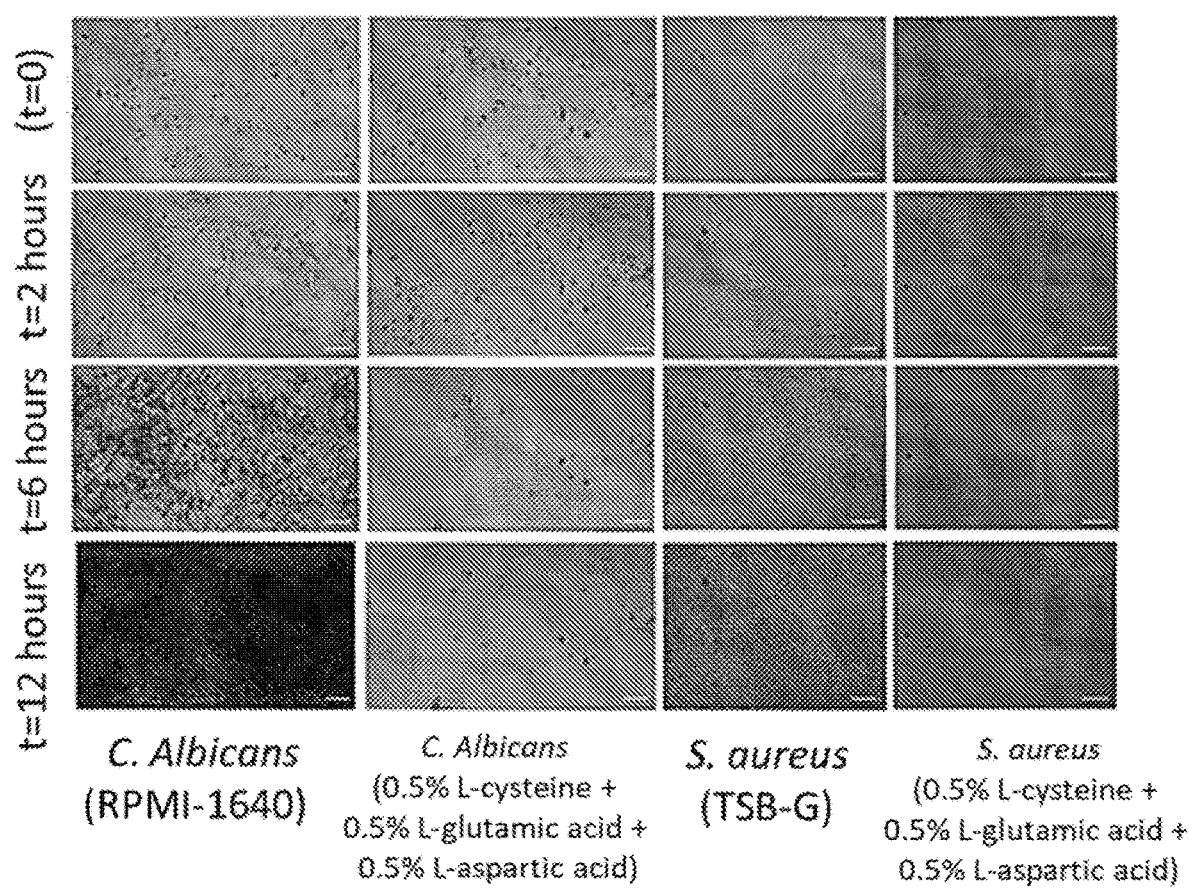
FIG. 2 shows biofilm reduction by compositions of the disclosure as seen in microfluidics device.

The 1.5% amino acid solution was also tested against both *C. albicans* and MRSA biofilms, using a microfluidics assay that allowed visualization of biofilm formation in real time. This assay mimiced the physiological conditions present in catheters, such as temperature and flow rate. Cells were seeded in a chamber, and media was allowed to flow for 24 hours. As the biofilm developed, it was visualized using a microscope and images captured using a camera, allowed capture of real time development of a 12-hour biofilm, in the absence and presence of the 1.5% amino acid solution. The results of the assay are summarized in FIG. 2. Wild-type biofilm formation can be seen in media, not supplemented with 1.5% amino acid solution (0.5% L-cysteine+0.5% L-aspartic acid+0.5% L-glutamic acid), in *C. albicans* and MRSA. In the former, seeded yeast cells strongly adhere to the surface, over time the cells form long intercalating hyphae and as time progresses, a thick biofilm can be seen. In the presence of the 1.5% amino acid solution, the cells do not adhere as strongly, fail to form filaments, and over time the cells flow away with the flow of the media. Formation of a wild-type MRSA biofilm is shown where the bacterial cells adhere to the surface and over time multiply and form several layers, with the biofilm covering the field of vision in 6 hours. The 1.5% amino acid solution has a similar effect on MRSA biofilms, as seen with *C. albicans* biofilm, the bacterial cells do not divide and are washed away by the flow of media. Thus, the 1.5% amino acid solution was highly effective in preventing biofilm formation in both *C. albicans* and MRSA in a catheter like device.

The Microfluidic Assay allows for the visualization of biofilm formation from individually adhered single cells when exposed to a fixed rate linear flow and is a derivate of the protocol Applicant previously described in the manuscript: Gulati et al (2017) Visualization of biofilm formation in *Candida albicans* using an automated microfluidic device. JoVE 130: e56743, which is incorporated by reference in its entirety. This assay uses BioFlux 48-Well low-shear plates (Fluxion Biosciences), a BioFlux 1000Z (Fluxion Biosciences) microfluidic flow device, and a Zeiss AX10 microscope. Media is pre-warmed to the desired temperature (normally 37° C.) to avoid formation of bubbles during the experiment. The temperature controller of the system was set to the desired temperature (normally 37° C.). Condensation was removed from the interphase plate before setting up the experiment by running sterile air through the system at 2 dyne/cm$^2$ for 10 minutes. The 48-well low shear plates (Fluxion Biosciences) were placed in the holder and 600-1, 000 μL of media and/or media and compound to test was added to the inlet wells (volumes larger than 600 μL are needed for assays over 12 hours in length). The interphase plate was positioned over the 48-well low shear plates (Fluxion Biosciences) and locked in place so that the system was airtight. Air was removed from the flow wells by running the media from the inlet to outlet wells for 5 mins at 1 dyne/cm$^2$. Overnight cultures were grown in YPD at 30° C., the density was determined in the morning, and cells were diluted to a final density of OD600=0.5 (or equivalent to 1×10$^7$ cells) in 50 μL per well of the desired medium. The experiment was performed with three replicates per strain or testing condition. Cells were seeded into the flow cell chamber by adding the cell culture to the outlet well of the BioFlux 48-Well plate (Fluxion Biosciences) and running the system with a backward flow (from outlet to inlet) at 2 dyne/cm$^2$ for 4 seconds. The seeded cells were allowed to adhere with no flow for 20 minutes at 37° C. Bright-field and phase contrast pre-wash images were acquired from three different sections of the flow chamber in each well using a Zeiss AX10 microscope. Wells were washed with media flowing from inlet to outlet wells at 1 dyne/cm$^2$ for 5 minutes to remove non-adherent cells. The remaining cells were incubated at 37° C. for 12 hours at 0.5 dyne/cm$^2$. Bright-field and phase contrast images were acquired from three different sections of the flow chamber in each well every 5 minutes using a Zeiss AX10 microscope for the remainder of the experiment. The protocol is described in the following three manuscripts: (1) Gulati et al (2018) In vitro culturing and screening of *Candida albicans* biofilms. Curr Protoc Microbiol 50(1): e60 doi: 10.1002/cpmc.60, (2) Gulati et al, (2017) Visualization of biofilm formation in *Candida albicans* using an automated microfluidic device. JoVE 130: e56743 doi: 10.3791/56743, and (3) Lohse et al, Antimicrob Agents Chemother. 2017 Mar. 13. pii: AAC.02749-16. doi: 10.1128/AAC.02749-16, the disclosure of which are incorporated by reference herein.

Example 5

Reduction of Cell Adherence and Alteration of Cell Shape in *Candida albicans* Biofilms Results from the microfluidics assay suggested that the 1.5% amino acid solution reduces cell adherence. The effect of the solution was tested on cell adherence in *Candida*

Figure 3A:
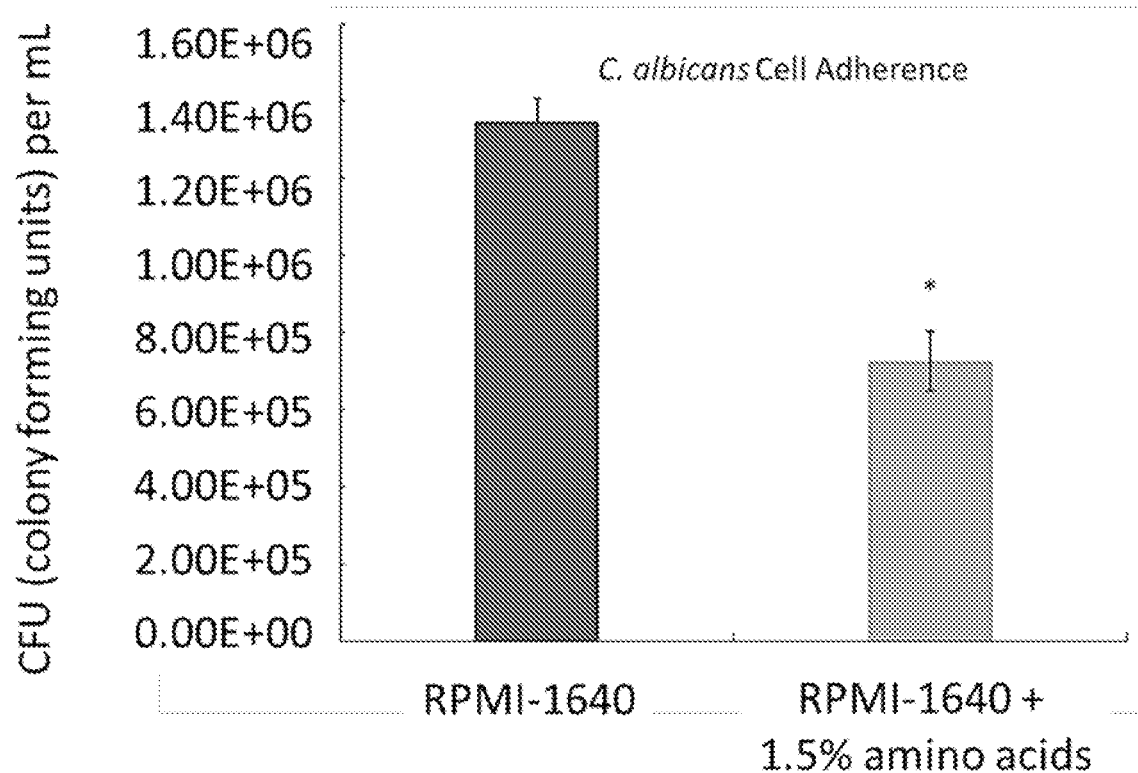
FIGS. 3A-3B show the reduction of cell adherence and inducement of cell death by compositions of the disclosure.

*albicans* using an in vitro assay. *C. albicans* cells were seeded on polystyrene plates, similar to the in vitro biofilm assay, for normal cell adherence. After 90 minutes, loosely adhered cells were washed, and adhered cells were assessed using serial dilutions and counting CFUs (colony forming units). Results showed that the combined 1.5% amino acid solution reduces cell adherence by almost 50% (FIG. 3A).

Figure 3B:
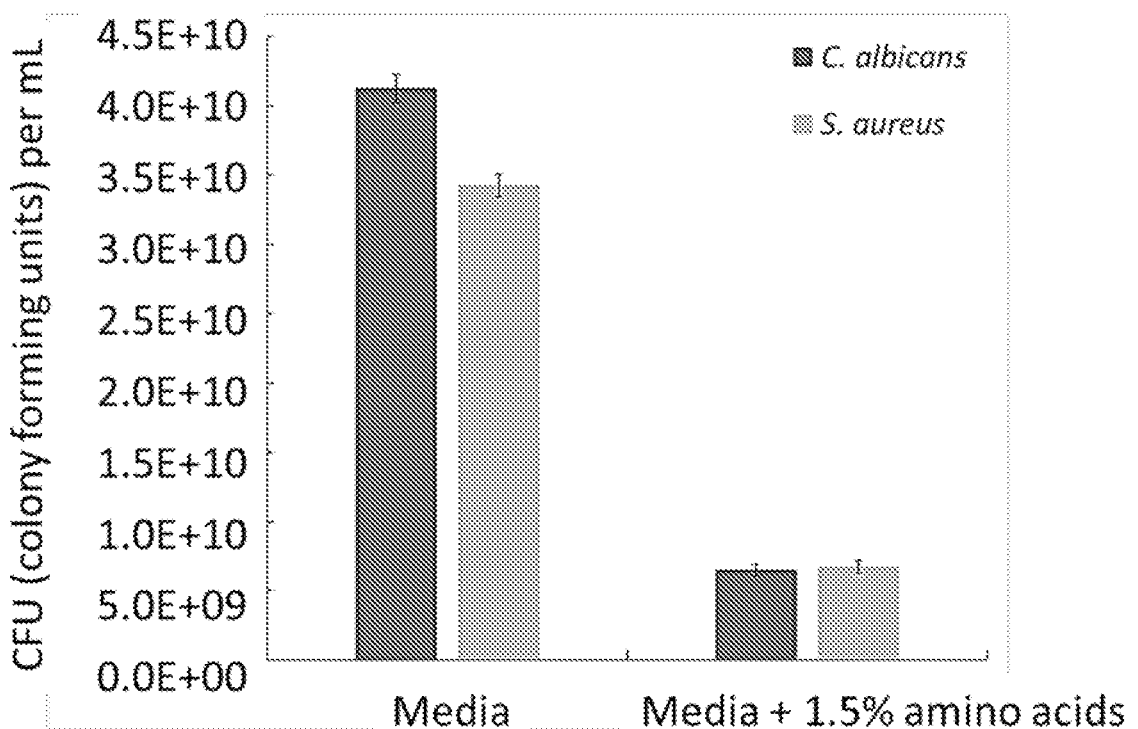

To determine if the amino acid solution induced cell death, the viability of the cells in the biofilms formed in the presence of the 1.5% amino acid solution was tested. For this assay *C. albicans* and MRSA wild-type biofilms were formed on polystyrene plates, in the presence of media without 1.5% amino acid solution. After 24 hours, the mature biofilms were further incubated for 24 hours, in the media with and without 1.5% amino acid solution. The viable cells in the biofilm were measured using CFUs (colony forming units). Results showed that 1.5% amino acid solution reduced cell viability in both *C. albicans* and MRSA biofilms, by 80-85%, compared with media not supplemented with 1.5% amino acids (FIG. 3B). These results suggest that the combined amino acids induce cell death.

Example 6

Alteration of Cell Shape

Figure 4:
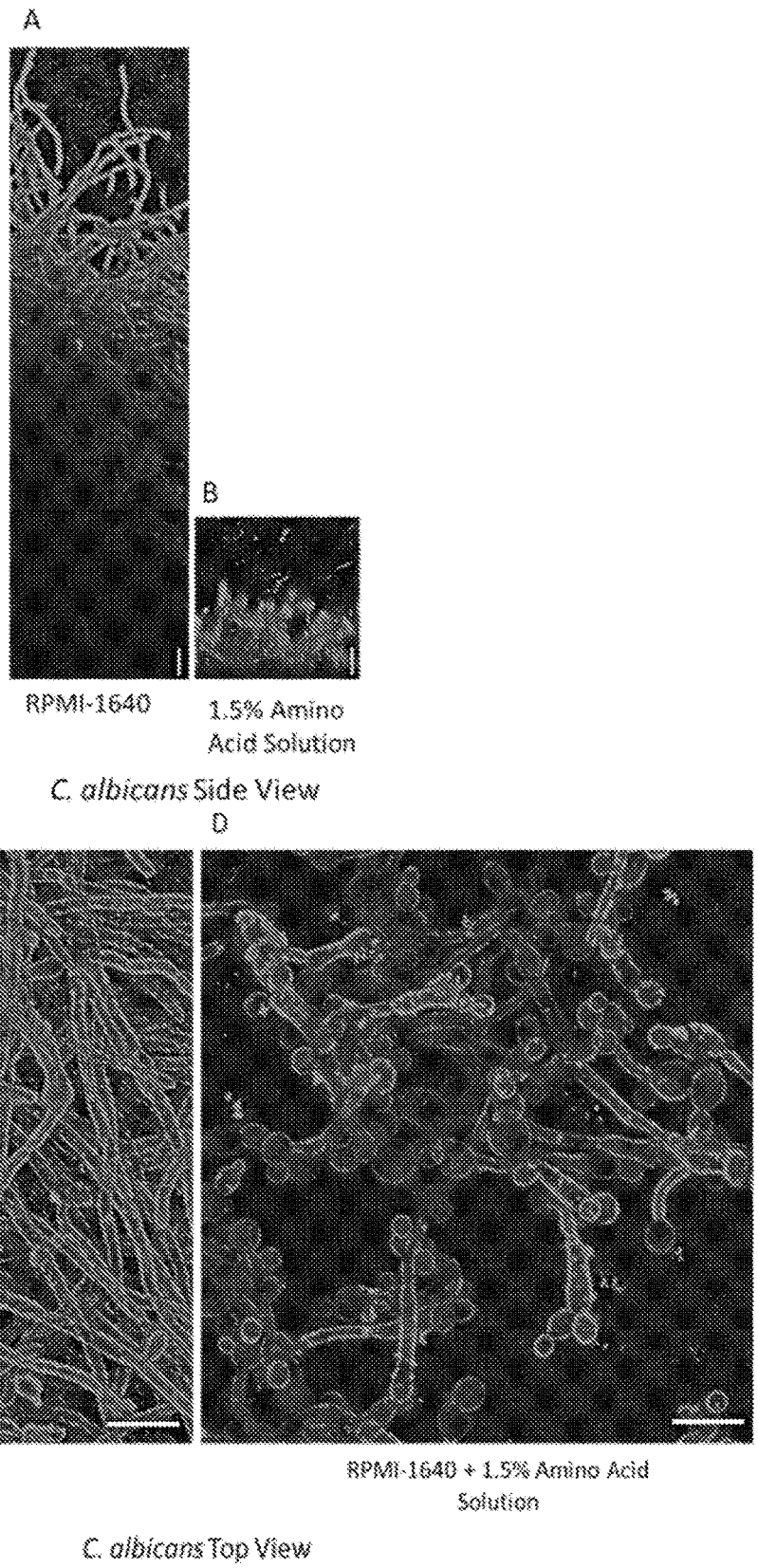
FIG. 4 shows the alteration of cell shape and reduction of biofilm thickness by compositions of the disclosure.

To determine if the reduction in biofilm is due to reduced adherence or due to other factors, confocal imaging was used to visualize altered biofilm structure and thickness. *C. albicans* biofilms have a characteristic 3-dimensional architecture that consists of a basal layer of adhered filamenting yeast cells and several layers of intercalating yeast and hyphal cells, enclosed by a matrix. However, the matrix is not visible in the confocal imaging assay used here, as the dye we used does not bind to the matrix. For this assay, *C. albicans* biofilms were developed for 24 hours, on polystyrene plates, in media with and without 1.5% amino acids. The mature biofilm from both conditions was imaged using an upright confocal microscope. Results showed that the 1.5% amino acid solution severely reduced the thickness of the biofilm, from ~270 μm seen in wild-type biofilms to ~20 μm (FIG. 4). Additionally, the *Candida* cell shape is altered in the 1.5% amino acid solution. The cells look swollen and stressed, compared with the cells seen in media without supplemented amino acids (FIG. 4). This implies that in addition to reduced adherence, the amino acid solution causes cell stress, or reduces cell growth.

Example 7

Effect of Compositions Against Other Bacteria and *Candida* Species

Figure 5A:
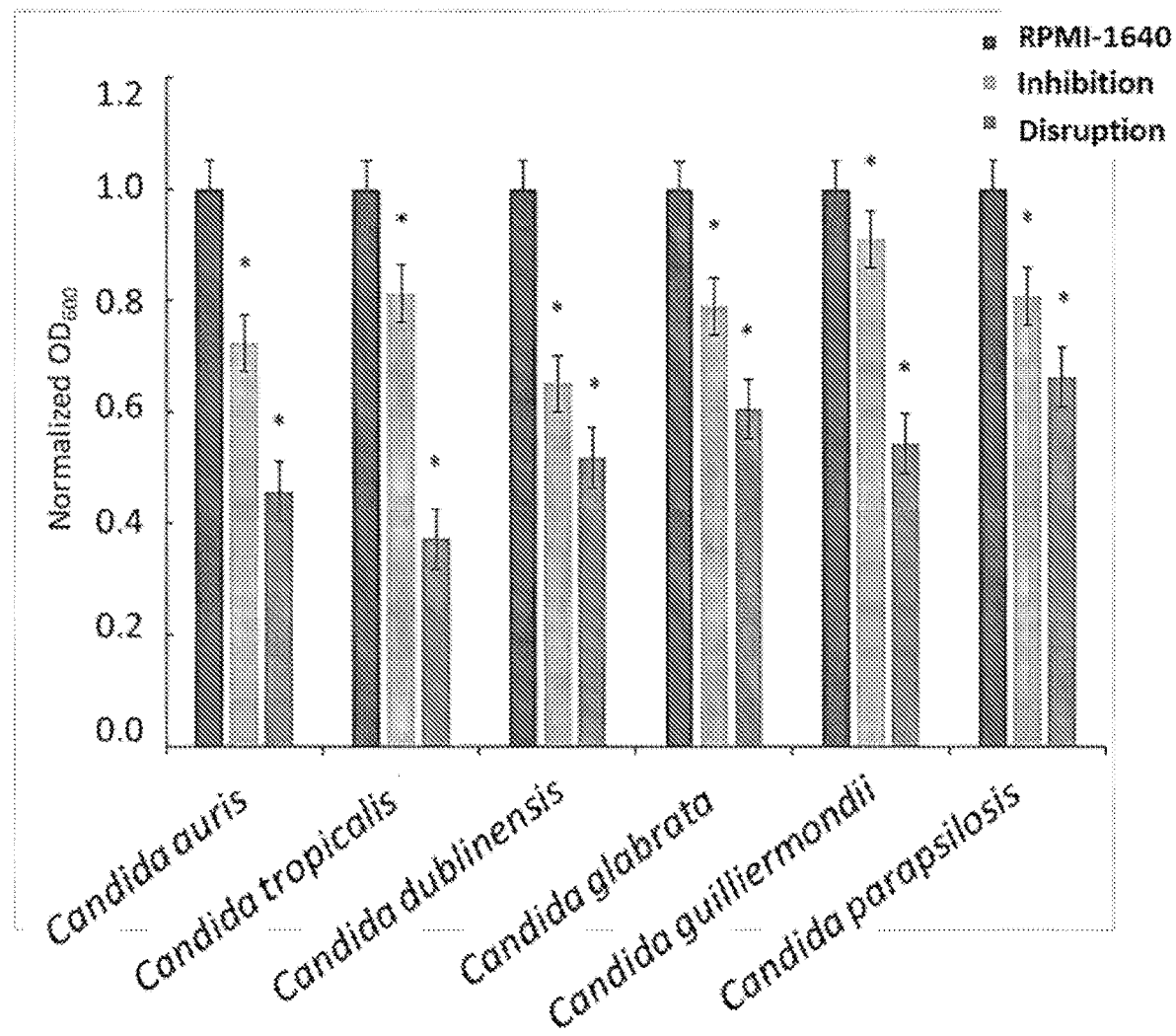
FIGS. 5A-5B show inhibition and disruption of biofilm formation.

Although, *C. albicans* is the most prevalent species implicated in a majority of infections, recent trends show an increased incidence of infections due to non-*albicans Candida* species. Thus, effectiveness of the 1.5% amino acid solution was tested against other *Candida* species commonly seen in healthcare settings. Results showed that the amino acid solution reduced biofilm formation in *C. auris* and *C. tropicalis* by 50%, and by an average of 60% in *C. dubliniensis, C. glabrata, C. guilliermondo* and *C. parapsilosis* (FIG. 5A). Additionally, the 1.5% amino acid solution also inhibited biofilm formation in all *Candida* strains by 20-30% (FIG. 5A).

Figure 5B:
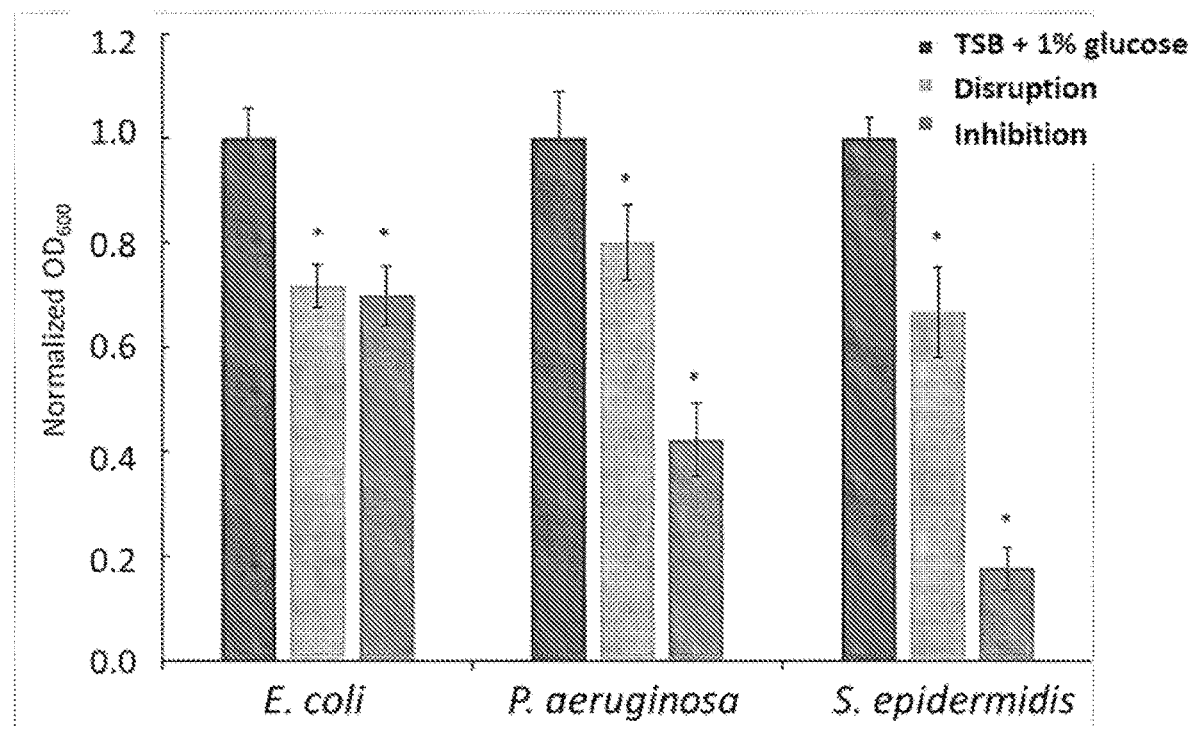

Next, the 1.5% amino acid solution was tested on the biofilms formed by other bacterial species, commonly encountered in catheter or other biofilm-related infections. Results showed that the 1.5% amino acid solution reduced biofilms formed by *E. coli, P. aeruginosa* and *S. epidermidis* (FIG. 5B).

Example 8

Reduction in *C. albicans* and *S. aureus* Biofilms in an In Vivo Model

Figure 6:
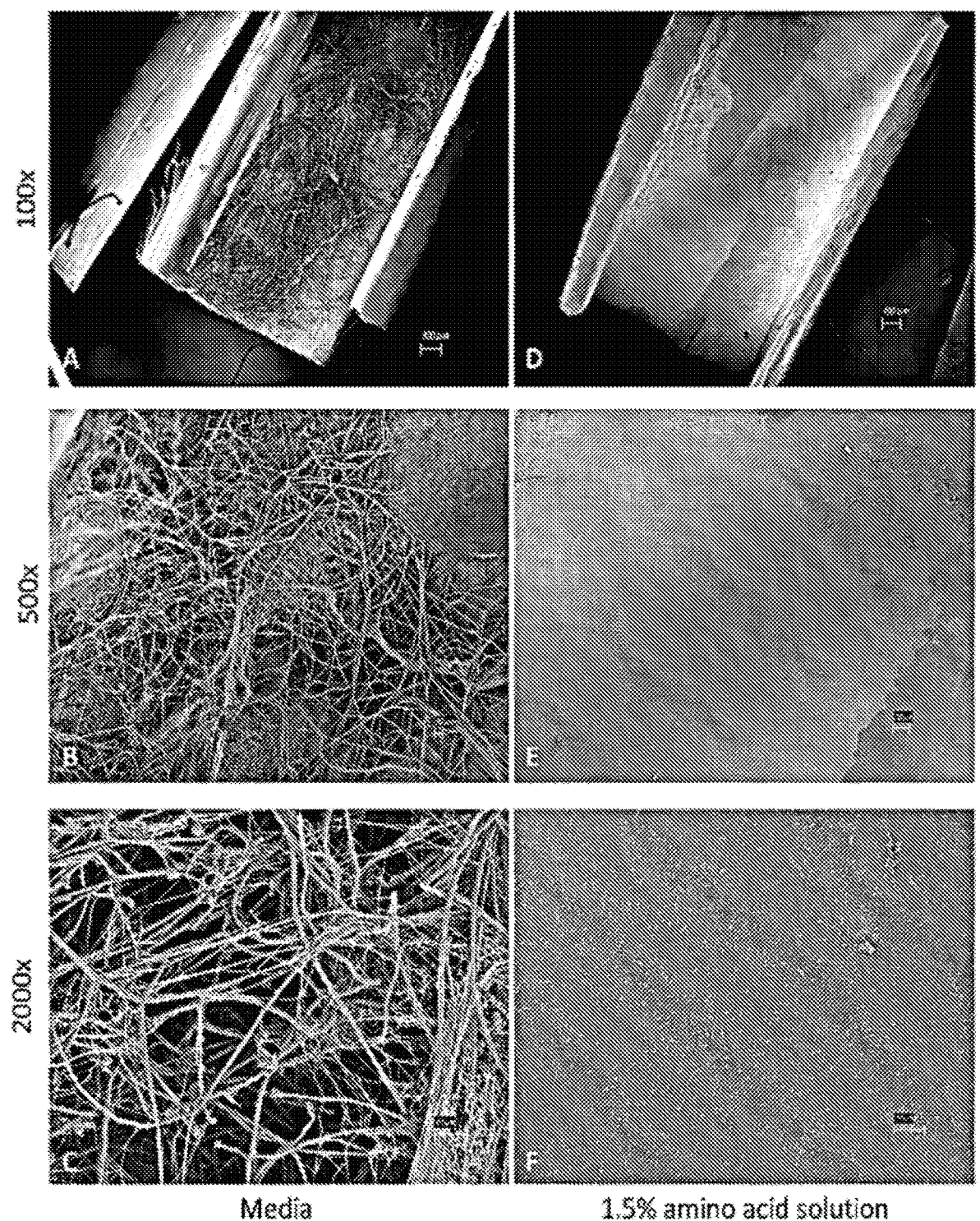
FIG. 6 shows reduction in vivo biofilm formation in *C. albicans* and *S. aureus* by compositions of the disclosure.
Figure 6:
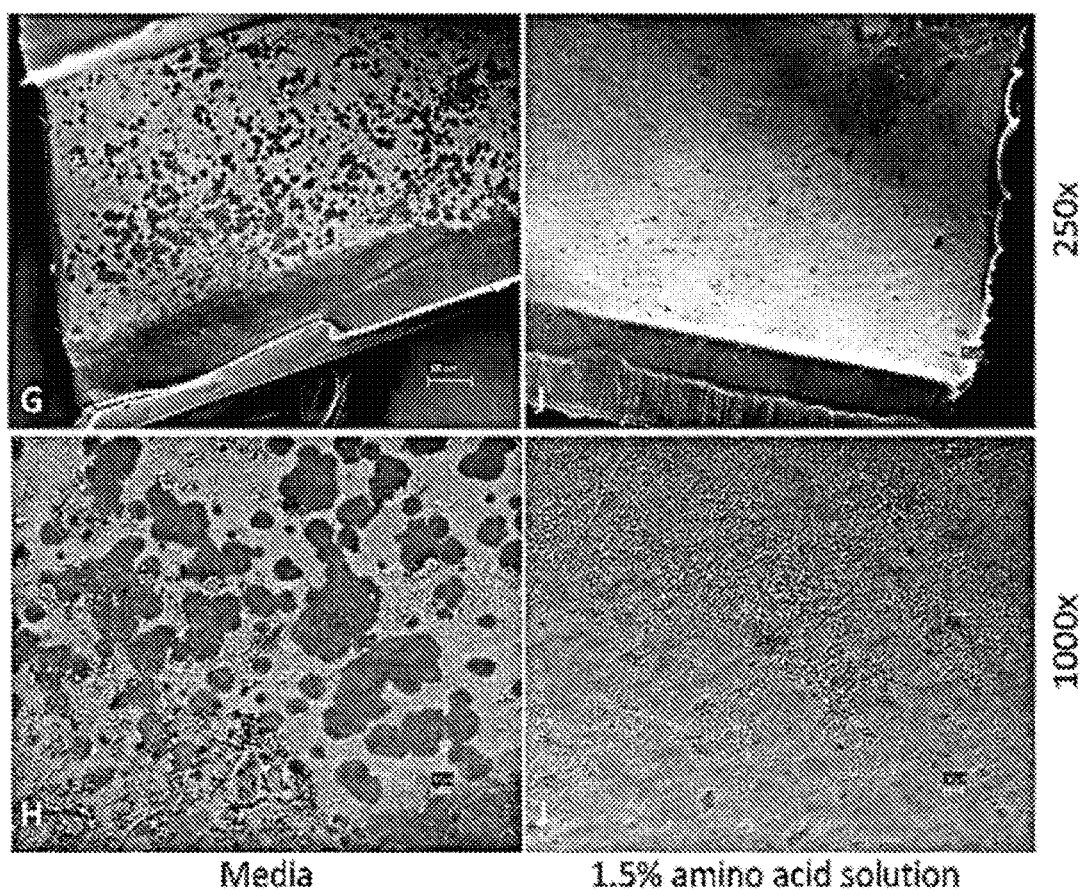
Figure 6:
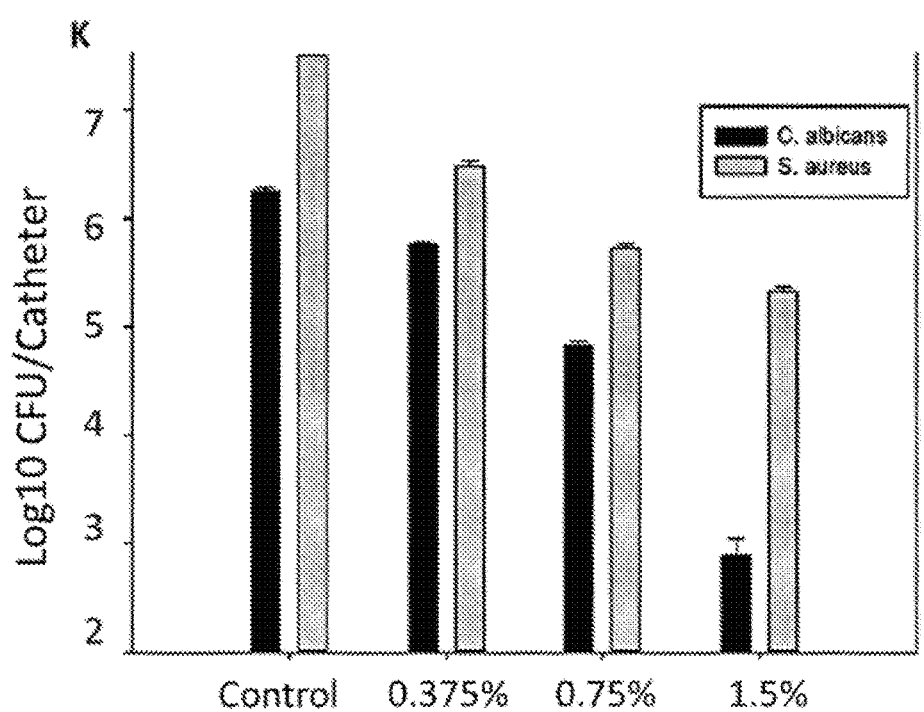

The 1.5% amino acid solution was tested on in vivo *C. albicans* biofilm formation with a rat central venous catheter biofilm model. Catheters were surgically implanted in the jugular vein and infected with *C. albicans* or MRSA, The cells were allowed to adhere for 4 hours and the catheters were flushed with media with and without 1.5% amino acid solution. The biofilm was allowed to develop for 24 hours and the intraluminal catheter surface was imaged using scanning electron microscopy (SEM). Results showed that the solution drastically reduces *C. albicans* biofilm formation in vivo (FIG. 6) compared with wild type biofilm (FIG. 6). The 1.5% solution also reduced *S. aureus* biofilms in vivo (FIG. 6). Also tested were 2× and 4× dilutions of the amino acid solution i.e. 0.75% and 0.375% and quantified the viable cells in the biofilm using CFUs (colony forming units). Results showed that the 1.5% solution induces cell death in in vivo conditions (FIG. 6).

Example 9

Materials and Methods

Strains and Growth Conditions

The following fungal strains were used in this study: *Candida albicans* SC5314, *Candida auris* CAU10, *C. tropicalis, C. dubliniensis, C. glabrata, C. guilliermondo* and *C. parapsilosis*. The following bacterial strains were used in this study: *S. aureus* USA300, *E. coli, P. aeruginosa* and *S. epidermidis*.

Fungal strains were streaked on a Yeast Peptone Dextrose (YPD) (BD, #242720) and incubated at 30° C. for 48 hours. A single colony from each strain to be tested was inoculated in YPD (BD, #242820) broth and grown for 12 hours, at 30° C., shaking at 225 rpm. Bacterial strains were streaked on a Blood Agar plates (5% sheep blood in Tryptic Soy Broth) and incubated at 37° C. for 24 hours. A single colony from each strain to be tested was inoculated in a TSB broth and grown for 12 hours, at 37° C. with shaking (225 rpm).

Preparation of Amino Acid Solutions

For fungal biofrims, all solutions were prepared in RPMI 1640 (Lonza, #04-525F) medium. All bacterial biofilm solutions were prepared in Tryptic Soy Broth (TSB) (BD, #211825) broth, supplemented with 1% glucose (henceforth referred to as TSB-G). All subsequent procedures were performed in a manner that maintained sterility. A solution of each amino acid to be tested was prepared in different concentrations (100 mg in 5 ml for 2% solution, 100 mg in 10 ml for 1% solution, 100 mg in 20 ml for 0.5% solution etc.) and homogenized with gentle agitation in the dark (4° C., 24 hours).

Amino acids so tested are as follows: L-alanine, Beta-alanine, L-arginine, L-asparagine, L-aspartic acid, L-A-aminoadipic acid, L-citrulline, L-cysteine, L-homocysteine, L-glutamic acid, L-glycine, L-histidine, 3-methyl-L-histidine, L-isoleucine, L-leucine, L-lysine, L-methionine, L-ornithine, L-phenylalanine, L-proline, Trans-4-hydroxy-L-proline, L-serine, O-phospho-L-serine, L-threonine, L-tryptophan, Taurine, L-tyrosine, L-valine, Ethanolamine and O-phosphoethanolamine. Two amino acids (1-methyl- L-histidine and L-cystathionine) were prepared in 0.2% solution due to limited solubility (10 mg in 5 ml).

Biofilm Assay

All biofilms were developed on 384-well polystyrene plates (Nunc, #242765). All PBS solutions used in these assays lack calcium and magnesium salts (D-PBS CMF) and are filter sterilized. Sustained inhibition and disruption biofilm assays were performed as previously described (8, 9)

Briefly, for inhibition assay, 1 µl of saturated overnight cell culture was added to either 80 µl of RPMI-1640 or RPMI-1640 supplemented with the amino acid to be tested, in a 384-well plate. The cells were allowed to adhere to the plate for 90 minutes at 37° C. with shaking (350 rpm, ELMI #DTS-4). Loosely bound cells were washed 1× with phosphate buffered saline (PBS) and 80 ul of RPMI-1640, or RPMI-1640 supplemented with amino acid was added to the plate. The plate was further incubated for 24 hours at 37° C. with shaking (350 rpm). Media was carefully aspirated and the biofilm was measured by optical density at 600 nm. Eight replicates were performed for each tested condition and the reported values are normalized to the control (RPMI-1640 media only).

For a disruption assay, 80 µl of RPMI-1640 was added to the plate, along with 1 µl of overnight cell culture. The cells were allowed to adhere to the plate for 90 minutes at 37° C. with shaking (350 rpm). Loosely bound cells were washed 1× with PBS and 80 µl of RPMI-1640 was added to the plate. The plate was further incubated for 24 hours at 37° C. with shaking (350 rpm). Media was carefully aspirated from the mature biofilm and 80 µl of RPMI-1640, or RPMI-1640 supplemented with the amino acid to be tested, was added drop wise to the plate. The plate was further incubated for 24 hours at 37° C. with shaking (350 rpm). Media was carefully aspirated and the biofilm was measured by optical density at 600 nm. Eight replicates were performed for each tested condition and the reported values are normalized to the control (RPMI-1640 media only).

For inhibition assay, 1 µl of overnight cell culture was added to either 80 µl of TSB-G, or TSB-G supplemented with the amino acid to be tested, in a 384-well plate. The cells were allowed to adhere to the plate for 60 minutes at 37° C. with no shaking. The media was carefully aspirated and 80 µl of TSB-G, or TSB-G supplemented with amino acid was added to the plate. The plate was further incubated for 24 hours at 37° C. with no shaking. Media was carefully aspirated and the biofilm was measured by optical density at 600 nm. Eight replicates were performed for each tested condition and the reported values are normalized to the control (TSB-G media only).

For disruption assay, 80 µl of TSB-G was added to the plate, along with 1 µl of overnight cell culture. The cells were allowed to adhere to the plate for 60 minutes at 37° C. with no shaking. The media was carefully aspirated and 80 µl of TSB-G was added to the plate. The plate was further incubated for 24 hours at 37° C. with no shaking. Media was carefully aspirated from the mature biofilm and 80 µl of TSB-G, or TSB-G supplemented with the amino acid to be tested, was added drop wise to the plate. The plate was further incubated for 24 hours at 37° C. with no shaking. Media was carefully aspirated and the biofilm was measured by optical density at 600 nm. Eight replicates were performed for each tested condition and the reported values are normalized to the control (TSB-G media only).

Adherence Assay

Assay was performed as previously described (8, 9). The cells are allowed to adhere under standard biofilm forming conditions (OD600=0.5 (equivalent to 1×107 cells) in 200 µL well volume, 37° C., 250 rpm) for 90 minutes in 96-well flat bottomed, non-tissue culture treated plates (BD Falcon #351172). Following the removal of non-adherent cells, wells were washed twice with 200 µL of PBS. The remaining cells were vigorously resuspended in water, serially diluted and plated on YPD plates. The plates were incubated at 30° C. for 2 days. Cells were quantified based on CFU counts. Data reported represents mean and standard deviation from 12 wells per condition.

Confocal Assay

Confocal assay was performed as previously described (9). The biofilm was developed by seeding cells from an overnight culture, on 6-well flat bottomed plate at a concentration of OD600=0.5 (equivalent to 1×107 cells) in 4000 µL well volume, 37° C., 200 rpm for 90 minutes. Loosely bound cells were washed 1× with phosphate buffered saline (PBS) and 4000 ul of RPMI-1640, or RPMI-1640 supplemented with amino acid was added to the plate. The plate was further incubated for 24 hours at 37° C. with shaking (200 rpm).

Cell Viability Assay

Biofilm cell viability assay was performed as previously described (9). The biofilm was developed, as previously described, on 96-well plates for 24 hours. Media was aspirated and the biofilm wells were carefully washed, without breaking the biofilm, twice with 200 µL of PBS. The biofilm cells were vigorously resuspended in water, serially diluted and plated on YPD plates. The plates were incubated at 30° C. for 2 days. Cells were quantified based on CFU counts. Data reported represents mean and standard deviation from 12 wells per condition.

Example 10

General Methods for Running Catheter Experiments

Preparation of catheters: (1) Cut polyethylene tubing into 50 cm in length. This catheter length is calculated based on placement in the jugular vein 2 cm above the right atrium, subcutaneous tunneling, and extension though an external protective device to the top of the animal cage where it will be secured for access. The volume of this catheter length is approximately 500 µL. With luer stub and stop cock, the total catheter volume is approximately 700 µL. (2) Sterilize catheters by ethylene oxide gas sterilization as autoclaving may destroy them.

Preparation of surgical equipment: (1) Sterilize surgical equipment, including surgical gowns, drapes, tethers, and surgical tools by autoclave. (2) Use prepackaged, sterilized stopcocks with luer stubs, sutures, and surgical gloves.

Catheter placement: (1) Anesthetize animals by intraperitoneal injection of a mixture of ketamine (80 mg/kg) and xylazine (8 mg/kg). This anesthesia protocol should produce anesthesia for approximately 120 min. (2) Prepare the animal for the surgical procedure by removing hair from the midscapular space, anterior chest, and neck with a rodent clipper. Prepare skin area with an antiseptic surgical scrub brush. (3) Create a sterile field under the surgical microscope by placing the rat in the supine position and preparing the surgical area with sterile drapes. Wear sterile gloves, mask, and gown. (4) Make a vertical incision in skin of the anterior neck just right of midline and use blunt surgical dissection to expose the right jugular vein. (5) To subcutaneously tunnel the catheter, create a second incision at the scruff and use blunt surgical dissection toward the initial surgical incision. Next, tunnel the proximal end of the catheter through this subcutaneous space to the midscapular space and externalize the catheter at the site of the second surgical incision. (6) Stabilize the jugular vein and make a longitudinal incision of a few millimeters to the vein wall using the vannas scissors. Instill heparinized saline (100 units/ml) into the catheter and insert the catheter in the vein (superior vena cava) opening. Advance to a site above the right atrium (approximately 2 cm). If the catheter is appropriately placed, blood should be able to be easily withdrawn. Conversely, if the catheter is in the atrium, it may be difficult to withdraw blood. Secure the catheter to the vein with (2-0) silk ties. (7) Secure the catheter to the subscapular skin scruff via a button using surgical staples Close both incisions with surgical staples and apply antibiotic ointment. Position a tether and rodent jacket on the animal to protect the catheter Secure the distal catheter segment and stopcock above the cage to allow easy access to catheter. (8) Surgical placement of a rat jugular venous catheter. (A) The catheter is inserted and secured in the jugular vein of an anesthetized animal. (B) The wire casing and rodent jacket protect the catheter and prevent the animal from disrupting the catheter. (9) Monitor the animal and wrap in a warming pad until it can lift its head and remain sternal. (10) Administer narcotic analgesia with buprenorphine 0.05 mg/kg subcutaneously twice daily for 24 h. (11) Allow the catheter to remain in place for 24 h prior to infection to allow for catheter surface conditioning with host proteins.

Animal and catheter maintenance: (1) Monitor the animals for signs of distress every 8 h through the study. In necessary, consider additional administration of buprenorphine 0.05 mg/kg subcutaneously twice daily for analgesia. (2) The anterior neck incision and the catheter exit site should be examined daily for signs of inflammation or purulence. In our experience with this protocol, superficial infections are uncommon. (3) House animals in an environmentally controlled room with 12-h light-dark cycle and maintain on a standard ad libitum rat diet. Following surgery and for the duration of the experiments, house animals singly in shoe box cages with normal bedding.

Preparation of inoculum: (1) Store fungal strains in 15% (vol/vol) glycerol stock at $-80°$ C. Prior to experiments, maintain strains on YPD medium supplemented with uridine. C. albicans, C. glabrata, and C. parapsilosis have successfully produced biofilms in this model. (2) Grow strains in YPD medium supplemented with uridine at 30° C. on an orbital shaker set to 200 RPM. Harvest during late logarithmic phase (this time period can vary among strains thus should be determined experimentally). Enumerate the cells by means of hemocytometer count. Adjust the final density to $1\times10^6$ cells/mL in YPD supplemented with uridine.

Infection of catheter: (1) Instill 700 µL of fungal inoculum in the catheter using a sterile syringe and the stopcock. This volume should fill the catheter lumen. (2) Allow the inoculum to dwell for 6 h, then withdraw or flush the catheter volume. Lock the catheter with same volume of sterile heparinized saline (heparin 100 units/mL, 0.15M NaCl).

Lock treatment of catheter (optional): (1) Prepare antifungal drugs or other agents to be tested in sterile saline (0.15M NaCl). (2) After 24 h of biofilm growth, withdraw or flush the heparinized saline from the catheter. (3) Instill the drug (700 µL) in the catheter with a sterile syringe and lock in place).

Harvesting the catheter: (1) Sacrifice animals by $CO_2$ asphyxiation. Typical collection times are 24 h after infection or 24 h after treatment administration. (2) Aseptically remove the catheter from the animal. Collect the proximal catheter segment (approximately 8 cm). (3) Gently place the proximal catheter tip (that was inserted in the animal) on sterile gauze. Allow the catheter fluid to drain the length of the catheter by capillary action. (4) Collect the proximal segment of catheter that was inserted in to the animal (approximately 2 cm in length). This segment can be prepared for microbiological enumeration, microscopy, or nucleic acid collection.

For endpoint determination: Microbiological counts (optional): (1) Place the catheter section in 1 mL sterile saline. (2) Sonicate sample for 10 min and vigorously vortex for 30 seconds. (3) To ascertain the extent of disease dissemination, remove the kidneys or other internal organs from the animal. Place in a suitable volume of saline and homogenize. (4) Plate serial dilutions (1:10) of the catheter fluid and organ material on SDA plates and incubate for 24 h at 30° C. (5) Enumerate fungal colony counts as an estimate of fungal viable burden per organ.

Fluorescent or confocal microscopy (optional): (1) Cut the catheter segment perpendicular to the catheter length with an 11-blade scalpel into multiple 2- to 3-mm-long "doughnut" segments. (2) Stain the catheter segments with fluorescent probes (FUN1 50 µM, Concanavalin Alexa Fluor 488 conjugate 200 mM, or calcofluor white (22.5 µg/ml) at 30° C. for 30 min in the dark. (3) Place catheter segments on the coverslip of a glass-bottom petri dish with the cut edge against the coverslip. Image the luminal surface of the catheter by fluorescent or confocal microscopy using the light source and filters appropriate for selected dyes.

Scanning electron microscopy (optional): (1) Cut the catheter segment perpendicular to the catheter length with an 11-blade scalpel into multiple 2- to 3-mm-long "doughnut" segments. (2) Place segments in fixative (1% glutaraldehyde, 4% formaldehyde in PBS) for 16 hours at 4° C. (3) Gently remove fixative and add 1 mL PBS for 10 min to wash samples. (4) Place samples in osmium tetroxide (1% in PBS) for 30 min. Osmium tetroxide is toxic and should only be used in a hood with protective gloves, lab coat, and eye wear. Proper disposal is required. (5) Gently remove osmium tetroxide and add 1 mL PBS for 10 min to wash samples. (6) Dehydrate samples by treating samples to a series of ethanol washes (30% for 10 min, 50% for 10 min, 70% for 10 min, 95% for 10 min, and 100% for 10 min). (7) Use critical point drying according to instruction to accomplish final desiccation. Our protocol uses three 10 minute $CO_2$ soaks prior to achieving critical point. (8) Section catheter segments length wise and mount the specimens on aluminum stubs with the luminal side visible. (9) Coat samples with gold appropriate for scanning electron microscope using a sputter coater. Our protocol coats samples for 2.5 to 3 minutes. (10) Image the luminal surface of catheter samples using scanning electron microscopy Example 11

Compositions of the Disclosure in a Rat Catheter Model

Testing the optimal amino acid mixture solution that is effective against both fungal and bacterial biofilms (0.5% L-cysteine+0.5% L-glutamic acid+0.5% L-aspartic acid) in a rat catheter model of biofilm infection. Methods to perform the assay are as follows:

Animals: Specific-pathogen-free male Sprague-Dawley rats weighing 350 g (Harlan)

Medications: (1) Heparin sodium for injection 1000 USP units/mL (APP Pharmaceuticals); (2) Xylazine (Sigma-Aldrich,); (3) Buprenorphine 0.3 mg/mL (Hospital Pharmacy); (4) Ketamine HCl 500 mg/10 mL (Bedford Laboratories); (5) Double Antibiotic Ointment:Bacitracin Zinc and Polymyxin B Sulfate (Fougera).

Surgical materials: (1) Polyethylene tubing with inner diameter 1.14 mm and outer diameter 1.57 mm. (PE 160, Intramedic, Becton Dickinson); (2) Three way large bore stopcock with rotating male luer lock adapter (Baxter Healthcare Corporation); (3) Rodent jacket, rat 250-350 g (Braintree Scientific, Inc); (4) Tether, 18' sewn (Braintree Scientific, Inc); (5) Scrub Care Surgical Scrub Brush-Sponge/Nail Cleaner (catalog Cardinal Health); (6) Polysulfone Button Tether for rats, 0.090 in lumen, 12 in (30 cm) (sterile) (Instech Solomon); (7) Skin stapler 5.7 mm×3.9 mm (Ethicon Endo-Surgery); (8) Surgical suture, sterile, non-absorbable, Silk black braided 2-0 18" (3.0 metric, 45 cm) (Ethicon Inc); (9) Surgical dissecting microscope (Stereo Zoom Microscope with fiber optic illuminator control (PZ-MIII-BS) World Precision Instruments); (10) Sterile syringes (variety of volumes); (11) Surgical attire: sterile surgical gloves, sterile gown, and surgical mask; (12) Rodent hair clipper (A5 power pro clipper, Oster) 13. Rat dissecting kit (World Precision Instruments,); (13) Far Infrared warming pad 14"×14" (Kent Scientific Corporation)

Fungal Isolates and media: Media 1: YPD medium supplemented with uridine: 1% yeast extract, 2% bacto peptone, 2% glucose, and uridine 80 µg/mL Materials for evaluation of selected endpoints:

Microbiologic counts (optional): (1) Sonicating water bath (FS 14 with 40-kHz transducer, Fisher Scientific); (2) Sabouraud dextrose agar (SDA plates: 4% dextrose, 1% peptone 1.5% agar, pH 5.6; (3) Tissue homogenizer (Polytron 3100, Brinkman Instruments)

Confocal or fluorescent microscopy (optional): (1) Fluorescent probes; (2) Calcofluor white or Fluorescent brightener 28 (Sigma-Aldrich): (3) FUN1 live dead yeast stain (Molecular Probes, Invitrogen); (4) Concavalin A Alexa Fluor 488 (Molecular Probes, Invitrogen); (5) Glass-bottom petri dish (coverslip 1.5, 35-mm disk P325G 1.5-14C, MatTek); (6) Confocal or fluorescent microscope with inverted objective (such as Zeiss Axiovert 200)

Scanning electron microscopy (optional): (1) Glutaraldehyde (25%) (Sigma-Aldrich); (2) Formaldehyde (37%) (Sigma-Aldrich); (3) Phosphate-buffered saline (PBS) (0.15 MNaCl, pH 7.4); (4) Osmium tetroxide (Electron Microscopy Sciences); (5) Critical point drier (Tousimis); (6) Gold sputter coater (Auto Conductavac IV, Seevac Inc.); (7) Ultra smooth carbon adhesive tabs (12 mm, Electron Microscopy Sciences); (8) Aluminum mounts (12.7 mm, Electron Microscopy Sciences); (9) Scanning electron microscope (JSM-6100, JEOL)

Candida biofilm cell nucleic acid collection (optional): (1) AE buffer (50 mM sodium acetate pH 5.2, 10 mM EDTA); (2) Liquid nitrogen; (3) Reagents for hot phenol RNA extraction Example 12

Combination Therapies of the Disclosure

Testing the optimal amino acid mixture solution that is effective against both fungal and bacterial biofilms (0.5% L-cysteine+0.5% L-glutamic acid+0.5% L-aspartic acid) in combination with known antimicrobial agents (antifungals for fungal biofilms and antibiotics for bacterial biofilms) to determine if there are synergistic effects with known antimicrobial therapeutics. Current antifungal and antibiotics are largely ineffective against biofilms.

We will test the experimental composition with one or a plurality of antibiotics and/or antifungals disclosed above to identify whether the antibiotics and/or antifungals will have a synergistic effect on biofilm inhibition and/or disruption in combination with the experimental composition. Known therapeutic doses of antibiotics and/or antifungals will be used in combination with one or plurality of ranges of experimental compositions. A non-limiting experimental protocol is as follows:

Anti-fungal Compositions Tested. (1) Experimental Composition: (0.5% L-cysteine+0.5% L-glutamic acid+0.5% L-aspartic acid); (2) Experimental Composition: (0.5% L-cysteine+0.5% L-glutamic acid+0.5% L-aspartic acid) Plus Ketoconazole; (3) Experimental Composition: (0.5% L-cysteine+0.5% L-glutamic acid+0.5% L-aspartic acid) Plus Fluconazole; (4) Experimental Composition: (0.5% L-cysteine+0.5% L-glutamic acid+0.5% L-aspartic acid) Plus Caspofungin; (5) Experimental Composition: (0.5% L-cysteine+0.5% L-glutamic acid+0.5% L-aspartic acid) Plus Amphotericin-B; (6) Negative Control (not including Experimental Composition)

Anti-bacterial Compositions Tested. (1) Experimental Composition: (0.5% L-cysteine+0.5% L-glutamic acid+0.5% L-aspartic acid); (2) Experimental Composition: (0.5% L-cysteine+0.5% L-glutamic acid+0.5% L-aspartic acid) Plus Ampicillin; (3) Experimental Composition: (0.5% L-cysteine+0.5% L-glutamic acid+0.5% L-aspartic acid) Plus Tetracycline; (4) Experimental Composition: (0.5% L-cysteine+0.5% L-glutamic acid+0.5% L-aspartic acid) Plus Vancomycin; (5) Experimental Composition: (0.5% L-cysteine+0.5% L-glutamic acid+0.5% L-aspartic acid) Plus Cephalosporin; (6) Negative Control (not including Experimental Composition).

Disruption Assay (Treatment):96-well plates will be inoculated with Candida albicans or Staphylococcus aureus at the concentrations disclosed in Example 1, and biofilms will be allowed to form and each composition will be tested for effectively disrupting the biofilm by measuring absorbance at O.D. 600 nm.

Inhibition Assay (Prophylaxis): 96-well plates will be inoculated with Candida albicans or Staphylococcus aureus at the concentrations disclosed in Example 1 in combination with each of the composition listed above, and each composition will be tested for effectively preventing the formation of the biofilm by measuring absorbance at O.D. 600 nm.

It is expected that administration of the experimental composition before, contemporaneously with, or after the one or plurality of antibiotics and/or antifungals will lead to a synergistic effect at disrupting and/or inhibiting bacterial and/or fungal biofilms.

Lohse et al, Antimicrob Agents Chemother. 2017 Mar. 13. pii: AAC.02749-16. doi: 10.1128/AAC.02749-16, which is incorporated by reference in its entirety.

Example 13

Contacting Compositions of the Disclosure with a Surface

Testing the optimal amino acid mixture solution that is effective against both fungal and bacterial biofilms (0.5% L-cysteine+0.5% L-glutamic acid+0.5% L-aspartic acid) as a sterilization agent for implants and other medical devices.

An implant model will be used for determining whether the non-bonded amino acids of the disclosure are useful for sterilizing medical device equipment. A protocol for this assay is as follows:

Squares of silicone (1.5 cm by 1.5 cm) will be cut from silicone sheets (Cardiovascular Instrument Corp.), washed in water, and autoclaved. Prior to inoculation, the squares will be incubated with bovine serum (B-9433; Sigma) overnight and then washed once in phosphate-buffered saline (PBS) immediately before inoculation. Strains will be grown overnight in yeast extract peptone-dextrose at 37° C. and diluted in SD medium plus 50 mM glucose to an optical density at 600 nm (OD600) of 1.0 or in Spider medium to an OD600 of 0.5.

Inoculation will be accomplished by adding 2 ml of this cell suspension to a silicone square in a 12-well plate and incubating at 37° C. for 90 min with gentle agitation (at 150 rpm). After this adherence step, each square will be washed with PBS and 2 ml of fresh medium containing the experimental composition will be added. Biofilms will be grown for 24 hours at 37° C. with gentle agitation in the presence and absence of the composition.

Biofilm growth disruption and/or inhibition will be assessed by confocal scanning laser microscopy as described in Nobile et al, (2012) A recently evolved transcriptional network controls biofilm development in *Candida albicans*. Cell 148: 126-138, which is incorporated by reference in its entirety.

Example 14

In Vitro Toxicity Testing of Compositions Described Herein

Preliminary toxicity assays are performed using FaDu oral epithelial cells. Isolated from a pharyngeal carcinoma, the FaDu cell line is available from the American Type Culture Collection, and is chosen because it represents a predominant cell type that is susceptible to biofilm infections in the human host. The cell lines re exposed to a number of compositions described herein, and are assessed in vitro toxicity using a Seahorse XF96 Flux Analyzer, which measures real-time cellular metabolism (both respiration and glycolysis) in a high throughput microplate format. Use of the Seahorse XF96 Flux Analyzer permits early assessment of "off-target" toxicity. The Seahorse XF96 Flux Analyzer measures the loss of respiratory capacity by readout of mitochondrial function measured through cellular $O_2$ consumption rates (OCRs) on FaDu oral epithelial cells over several time points to allow for early risk assessment of the amino acid mixture. After determining the basal OCR, the proton ionophore carbonyl cyanide p-trifluoromethoxy-phenylhydrazone (FCCP) is injected to uncouple oxygen consumption from ATP production (essentially a cellular "stress test" to measure maximal activity of the electron transport chain). Compositions are assessed at varying concentrations, and those with an FCCP-OCR of less than or equal to 85% of the vehicle control are mitochondrially toxic.

Example 15

Cytochrome P450, hERG Channel, NEK293 Toxicity Testing of Compositions Described Herein Assays are conducted to determine whether compositions described herein inhibit or are a substrate for Cytochrome P450 (looking at 1A2, 2B6, 2C19, 2C9, 2D6, 3A4, and 3A5). These compositions are tested for killing of HEK293 cells using a standard colorimetric assay measuring reduction of 3-(4, 5-dimethylthiazolyl-2)-2, 5-diphenyltetrazolium bromide (MTT) that occurs in metabolically active cells. Inhibition of the hERG channel are also tested.

While embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein may be use. It is intended that the following claims define the scope of the disclosure and that methods within the scope of these claims and their equivalents be covered thereby. All publications, patents, and patent applications mentioned in this specification are herein incorporated by reference to the same extent as if each individual publication, patent, or patent application was specifically and individually indicated to be incorporated by reference.

What is claimed is:

1. A method of inhibiting or disrupting a biofilm on a surface, treating a bacterial infection in a subject in need thereof, or treating a fungal infection in a subject in need thereof, the method comprising contacting the surface with a composition or administering a composition to the subject; wherein the composition comprises:
   (a) a first compound of formula (I) or a salt thereof, wherein
      (i) $R^1$ is —$SR^5$,
      (ii) $R^5$ is hydrogen, $C_{1-6}$ alkyl, $C_{2-6}$ alkenyl, $C_{2-6}$ alkynyl, $C_{3-12}$ carbocycle, or 3 to 12 membered heterocycle; optionally substituted with one or more substituents selected from the group consisting of halogen, —CN, —$NO_2$, —OH, —$NH_2$, —COOH, and —$OCH_3$, and
      (iii) n is 0, 1, 2, 3, 4, or 5;
   (b) a second compound of formula (I) or a salt thereof, wherein
      (i) $R^1$ is —CO(O)$R^5$,
      (ii) $R^5$ is hydrogen, $C_{1-6}$ alkyl, $C_{2-6}$ alkenyl, $C_{2-6}$ alkynyl, $C_{3-12}$ carbocycle, or 3 to 12 membered heterocycle; optionally substituted with one or more substituents selected from the group consisting of halogen, —CN, —$NO_2$, —OH, —$NH_2$, —COOH, and —$OCH_3$, and
      (iii) n is 0, 2, 3, 4, or 5;
   (c) a third compound of formula (I) or a salt thereof, wherein
      (i) $R^1$ is —CO(O)$R^5$,
      (ii) $R^5$ is $C_{1-6}$ alkyl, $C_{2-6}$ alkenyl, $C_{2-6}$ alkynyl, $C_{3-12}$ carbocycle, or 3 to 12 membered heterocycle; optionally substituted with one or more substituents selected from the group consisting of halogen, —CN, —$NO_2$, —OH, —$NH_2$, —COOH, and —$OCH_3$, and
      (iii) n is 0, 1, 3, 4, or 5;
wherein the compound of formula (I) is:

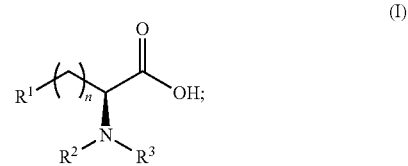

(I)

wherein:
   $R^2$ and $R^3$ are hydrogen; or one of $R^2$ and $R^3$ is hydrogen, and the other of $R^2$ and $R^3$ with $R^1$ is taken together with the atoms to which they are attached to form a heterocycle substituted with one or more $R^6$; and
   each $R^6$ is independently halogen, —$NO_2$, —CN, —$OR^5$, —$SR^5$, —N($R^5$)$_2$, —C(O)$R^5$, —C(O)O$R^5$, —OC(O)$R^5$, —OC(O)O$R^5$, —OC(O)N($R^5$)$_2$, —$NR^5$C(O)$R^5$, —C(O)N($R^5$)$_2$, =O, =S, =N($R^5$), $C_{1-10}$ alkyl, $C_{2-10}$ alkenyl, or $C_{2-10}$ alkynyl; each of which is independently and optionally substituted at each occurrence with one or more substituents selected from the group consisting of halogen, —CN, —NO$_2$, —OH, —NH$_2$, —COOH, and —OCH$_3$.

2. The method of claim 1 comprising inhibiting or disrupting the biofilm on the surface, the method comprising contacting the surface with the composition.

3. The method of claim 2, wherein the biofilm is a fungal biofilm.

4. The method of claim 2, wherein the biofilm is a bacterial biofilm.

5. The method of claim 1 comprising treating the bacterial infection in the subject in need thereof, the method comprising administering to the subject the composition.

6. The method of claim 1 comprising treating the fungal infection in the subject in need thereof, the method comprising administering to the subject the composition.

7. The method of claim 1, wherein the composition comprises:
   (a) about 0.1 w/v % to about 5 w/v % of the first compound of formula (I) or the salt thereof,
   (b) about 0.1 w/v % to about 5 w/v % of the second compound of formula (I) or the salt thereof, and
   (c) about 0.1 w/v % to about 5 w/v % of the third compound of formula (I) or the salt thereof.

8. The method of claim 1, wherein the composition further comprises a pharmaceutically acceptable carrier.

9. The method of claim 1, wherein the composition further comprises saline.

10. The method of claim 1, wherein the composition further comprises glycerin.

11. The method of claim 1, wherein the composition further comprises from about 0.1 w/v % to about 5 w/v % of glycerin.

12. The composition of claim 1, wherein the composition is in the form of an intravenous formulation.

13. The composition of claim 1, wherein the composition is in the form of a solution.

14. The composition of claim 1, wherein the composition is in the form of a douche.

15. The composition of claim 1, wherein the composition does not contain an amino acid selected from the group consisting of alanine, arginine, asparagine, citrulline, glycine, isoleucine, leucine, lysine, methionine, 3-methyl histidine, phenylalanine, ornithine, proline, serine, taurine, threonine, tryptophan, valine, or a combination of two or more thereof.

16. The method of claim 1, wherein the composition does not contain alanine, arginine, asparagine, citrulline, glycine, isoleucine, leucine, lysine, methionine, 3-methyl histidine, phenylalanine, ornithine, proline, serine, taurine, threonine, tryptophan, or valine.

17. The method of claim 1, wherein the fungal infection is *Candida albicans, Candida guilliermondii, Candida parapsilosis, Candida glabrata, Candida tropicalis, Candida dubliniensis, Candida auris, Tinea corporis, Tinea cruris, Tinea faciei, Tinea pedis, Trichophyton rubrum, Trichophyton interdigitale, Trichophyton verrucosum, Trichophyton mentagrophytes, Trichophyton megninii, Trichophyton tonsurans, Trichophyton schoenleinii, Trichophyton soudanense, Trichophyton violaceum, Epidermophyton floccosum, Microsporum audouini, Microsporum canis, Microsporum distortum, Microsporum gypseum; Scopulariopsis brevicaulis*, a *Fusarium* species, an *Aspergillus* species, *Alternaria, Acremonium, Scytalidinum dimidiatum, Scytalidinium hyalinum, Malassezia furfur*, or a *Cryptococcus* species.

18. The method of claim 1, wherein the bacterial infection is *Staphylococcus aureus, Escherichia coli, Pseudomonas aeruginosa, Staphylococcus epidermidis, Streptococcus mutans, Listeria monocytogenes, Lactobacillus plantarum, Lactobacillus lactis, Klebsiella pneumonia, Proteus mirabilis, Streptococcus mitis, Streptococcus salivarius, Streptococcus pneumoniae, Rothia dentocariosa, Streptococcus sobrinus, Stomatococcus mucilaginosus*, a *Corynebacterium* species, a *Micrococcus* species, *Lactobacillus plantarum*, a group *B Streptococcus* species, an *Enterococcus* species, a coagulase-negative *Staphylococcus* species, a β-hemolytic *Streptococcus* species, or *Listeria monocytogenes*.

* * * * *